(12) United States Patent
Giampietro et al.

(10) Patent No.: US 11,297,838 B2
(45) Date of Patent: Apr. 12, 2022

(54) PESTICIDAL COMPOSITIONS AND METHODS

(71) Applicant: CORTEVA AGRISCIENCE LLC, Indianapolis, IN (US)

(72) Inventors: Natalie C. Giampietro, Carmel, IN (US); David Demeter, Fishers, IN (US); Lindsey G. Horty, Indianapolis, IN (US); Gary D. Crouse, Noblesville, IN (US); Thomas C. Sparks, Greenfield, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

(21) Appl. No.: 17/263,924

(22) PCT Filed: Dec. 12, 2019

(86) PCT No.: PCT/US2019/065869
§ 371 (c)(1),
(2) Date: Jan. 28, 2021

(87) PCT Pub. No.: WO2020/139566
PCT Pub. Date: Jul. 2, 2020

(65) Prior Publication Data
US 2021/0282402 A1    Sep. 16, 2021

Related U.S. Application Data

(60) Provisional application No. 62/784,911, filed on Dec. 26, 2018.

(51) Int. Cl.
| | | |
|---|---|---|
| *A01N 47/18* | (2006.01) |
| *A61P 33/14* | (2006.01) |
| *A01N 47/22* | (2006.01) |
| *A61K 31/427* | (2006.01) |
| *C07D 417/12* | (2006.01) |

(52) U.S. Cl.
CPC .......... *A01N 47/18* (2013.01); *A01N 47/22* (2013.01); *A61K 31/427* (2013.01); *A61P 33/14* (2018.01); *C07D 417/12* (2013.01)

(58) Field of Classification Search
CPC ...... A61K 31/427; A01N 47/18; A01N 47/22; C07D 417/12; A61P 33/14
USPC ....................................................... 514/369
See application file for complete search history.

(56) References Cited

U.S. PATENT DOCUMENTS

| | | |
|---|---|---|
| 9,249,133 B2 | 2/2016 | Fischer et al. |
| 2018/0111924 A1 | 4/2018 | Webster et al. |

FOREIGN PATENT DOCUMENTS

| | | |
|---|---|---|
| EP | WO 2014/160031 A1 | 10/2014 |
| EP | WO 2019/113006 A1 | 6/2019 |

*Primary Examiner* — Kahsay Habte

(57) ABSTRACT

This disclosure relates to the field of molecules having pesticidal utility against pests in phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the structure of Formula A.

Formula A

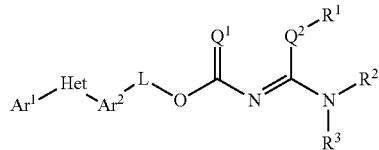

18 Claims, No Drawings

PESTICIDAL COMPOSITIONS AND METHODS

CROSS REFERENCE TO RELATED APPLICATIONS

This application claims the benefit of U.S. Provisional Patent Application Ser. No. 62/784,911 filed Dec. 26, 2018, which is expressly incorporated by reference herein.

FIELD OF THE INVENTION

The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

SUMMARY OF THE INVENTION

In one aspect, provided are molecules having the structure of Formula A:

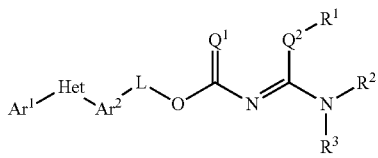

Formula A wherein:
(A) $Ar^1$ is selected from
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
   wherein said substituted furanyl, substituted phenyl, substituted pyridazinyl, substituted pyridyl, substituted pyrimidinyl, and substituted thienyl have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, or $S(=O)_nNR^xR^y$, or (Het-1),
   wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)OC_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, $S(=O)_nNR^xR^y$, or (Het-1);

(B) Het is a 5- or 6-membered, saturated or unsaturated, heterocyclic ring, containing one or more heteroatoms independently selected from nitrogen, sulfur, or oxygen, and where $Ar^1$ and $Ar^2$ are not ortho to each other (but may be meta or para, such as, for a five-membered ring they are 1,3 and for a 6-membered ring they are either 1,3 or 1,4) and where said heterocyclic ring may also be substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, or $S(=O)_nNR^xR^y$, wherein each alkyl, haloalkyl, cycloalkyl, halocycloalkyl, alkoxy, haloalkoxy, alkenyl, cycloalkenyl, haloalkenyl, alkynyl, phenyl, and phenoxy substituent may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, or $S(=O)_nNR^xR^y$;

(C) $Ar^2$ is selected from (1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, $S(=O)_nNR^xR^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, $S(=O)_nNR^xR^y$, or (Het-1);

(D) L is linker selected from (1) a bond, (2) —$CR^4R^5$—$CR^6R^7$—, or (3) —$CR^4$=$CR^6$—, wherein each of $R^4$, $R^5$, $R^6$, and $R^7$ is selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_1$-$C_8$ alkoxy, $C_1$-$C_8$ haloalkoxy, $C_2$-$C_8$ alkenyl, $C_2$-$C_8$ haloalkenyl, $C_2$-$C_8$ alkynyl, $C_2$-$C_8$ haloalkynyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_3$-$C_8$ cycloalkenyl, $C_3$-$C_8$ halocycloalkenyl, $C(=O)(C_1$-$C_6$ alkyl), $C(=O)O(C_1$-$C_6$ alkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(=O)_n(C_1$-$C_6$ alkyl), $C(=O)(C_1$-$C_6$ alkyl)$C(=O)O(C_1$-$C_6$ alkyl), $S(=O)_n(C_1$-$C_8$ alkyl), $S(=O)_n(C_3$-$C_8$ cycloalkyl), $S(=O)_n(C_1$-$C_8$ haloalkyl), $S(=O)_n(C_3$-$C_8$ halocycloalkyl), phenyl, or phenoxy;

(E) $R^4$ and $R^6$ together can optionally form a 3- to 7-membered saturated or unsaturated ring which may contain C=O, C=S, N, S or O, and is optionally substituted with H, OH, F, Cl, Br, I, CN, $NO_2$, $NR_xR_y$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $C_3$-$C_6$ cycloalkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(=O)_n(C_1$-$C_6$ alkyl), $(C_1$-$C_6$ alkyl)$C(=O)O(C_1$-$C_6$ alkyl), phenyl, phenoxy, and Het-1;

(F) $Q^1$ is selected from O or S;

(G) $Q^2$ is selected from O or S;

(H) $R^1$ is selected from (J), H, $C_1$-$C_8$ alkyl, $C_3$-$C_8$ cycloalkyl, $C_2$-$C_8$ alkenyl, $C_2$-$C_8$ alkynyl, $C(=O)(C_1$-$C_8$ alkyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)phenyl, $(C_1$-$C_8$ alkyl)-O-phenyl, $C(=O)$(Het-1), (Het-1), $(C_1$-$C_8$ alkyl)-(Het-1), $(C_1$-$C_8$ alkyl)-$C(=O)$—$(C_1$-$C_8$ alkyl), $(C_1$-$C_8$ alkyl)-$OC(=O)$—$(C_1$-$C_8$ alkyl), $(C_1$-$C_8$ alkyl)-O—$C(=O)O$—$(C_1$-$C_8$ alkyl), $(C_1$-$C_8$ alkyl)-O—$C(=O)NR^xR^y$, $(C_1$-$C_8$ alkyl)-$C(=O)N(R^x)(C_1$-$C_8$ alkyl)-(Het-1), $(C_1$-$C_8$ alkyl)-$C(=O)$(Het-1), $(C_1$-$C_8$ alkyl)-$C(=O)N(R^x)(C_1$-$C_8$ alkyl)$N(R^y)C(=O)OH$, $(C_1$-$C_8$ alkyl)-$C(=O)N(R^x)(C_1$-$C_8$ alkyl)$N(R^y)(R^x)$, $(C_1$-$C_8$ alkyl)-$C(=O)N(R^x)(C_1$-$C_8$ alkyl)$N(R^y)C(=O)O$—$(C_1$-$C_8$ alkyl), $(C_1$-$C_8$ alkyl)-$C(=O)N(R^x)(C_1$-$C_8$ alkyl)$(N(R^y)C(=O)O$—$(C_1$-$C_8$ alkyl)$C(=O)OH$, $(C_1$-$C_8$ alkyl)-$C(=O)$(Het-1)$C(=O)O$—$(C_1$-$C_8$ alkyl), $(C_1$-$C_8$ alkyl)-$OC(=O)O$—$(C_1$-$C_8$ alkyl), $(C_1$-$C_8$ alkyl)-$OC(=O)$—$(C_1$-$C_8$ alkyl), $(C_1$-$C_8$ alkyl)-$OC(=O)$—$(C_3$-$C_8$ cycloalkyl), $(C_1$-$C_8$ alkyl)-$OC(=O)$-(Het-1), $(C_1$-$C_8$ alkyl)-$OC(=O)$—$(C_1$-$C_8$ alkyl)$N(R^x)C(=O)$ O—($C_1$-$C_8$ alkyl), ($C_1$-$C_8$ alkyl)-NR$^x$R$^y$, ($C_1$-$C_8$ alkyl)-S-(Het-1), ($C_1$-$C_8$ alkyl)S(=O)$_n$(Het-1), or ($C_1$-$C_8$ alkyl)-O-(Het-1), wherein each alkyl, cycloalkyl, phenyl, and (Het-1) are optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)OH, C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(I) R$^2$ is selected from (J), H, OH, SH, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynylS(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(=O)NR$^x$R$^y$, ($C_1$-$C_8$ alkyl)-C(=O)N(R$^x$)($C_1$-$C_8$ alkyl)-(Het-1), ($C_1$-$C_8$ alkyl)-C(=O)(Het-1), ($C_1$-$C_8$ alkyl)-C(=O)N(R$^x$)($C_1$-$C_8$ alkyl)N(R$^y$)C(=O)OH, ($C_1$-$C_8$ alkyl)-C(=O)N(R$^x$)($C_1$-$C_8$ alkyl)N(R$^x$)(R$^y$), ($C_1$-$C_8$ alkyl)-C(=O)N(R$^x$)($C_1$-$C_8$ alkyl)N(R$^y$)C(=O)O—($C_1$-$C_8$ alkyl), ($C_1$-$C_8$ alkyl)-C(=O)N(R$^x$)($C_1$-$C_8$ alkyl)(N(R$^y$)C(=O)O—($C_1$-$C_8$ alkyl)C(=O)OH, ($C_1$-$C_8$ alkyl)-C(=O)(Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(=O)-(Het-1), ($C_1$-$C_8$ alkyl)-OC(=O)—($C_1$-$C_8$ alkyl)N(R$^x$)C(=O)O—($C_1$-$C_8$ alkyl), ($C_1$-$C_8$ alkyl)-NR$^x$R$^y$, ($C_1$-$C_8$ alkyl)-S-(Het-1), ($C_1$-$C_8$ alkyl)S(=O)$_n$(Het-1), or ($C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, NO$_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)OH, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, halophenyl, phenoxy, and (Het-1);

(J) R$^1$ and R$^2$ may be a 1- to 4-membered saturated or unsaturated, hydrocarbyl link, which may contain one or more heteroatoms selected from nitrogen, sulfur, and oxygen, and together with (Q$^2$)(C)(N) forms a 4- to 7-membered cyclic structure, wherein said hydrocarbyl link may optionally be substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, substituted phenyl, phenoxy, or (Het-1);

(K) R$^3$ is selected from $C_3$-$C_8$ cycloalkyl, phenyl, ($C_1$-$C_8$ alkyl)phenyl, ($C_1$-$C_8$ alkyl)-O-phenyl, ($C_2$-$C_8$ alkenyl)-O-phenyl, (Het-1), ($C_1$-$C_8$ alkyl)-(Het-1), ($C_1$-$C_8$ alkyl)-O-(Het-1), wherein the $C_3$-$C_8$ cycloalkyl, phenyl, ($C_1$-$C_8$ alkyl)phenyl, ($C_1$-$C_8$ alkyl)-O-phenyl, ($C_2$-$C_8$ alkenyl)-O-phenyl, (Het-1), ($C_1$-$C_8$ alkyl)-(Het-1), or ($C_1$-$C_8$ alkyl)-O-(Het-1) may be optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)O($C_1$-$C_8$ haloalkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, (Het-1), or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n$ ($C_1$-$C_6$ alkyl), $S(=O)_n$($C_1$-$C_6$ haloalkyl), phenyl, and oxo;

(L) $R^x$ and $R^y$ are independently selected from H, OH, SH, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n$ ($C_3$-$C_8$ cycloalkyl), $S(=O)_n$($C_3$-$C_8$ halocycloalkyl), $S(=O)_n$ ($C_1$-$C_8$ alkyl), $S(=O)_n$($C_1$-$C_8$ haloalkyl), $OSO_2$ ($C_1$-$C_8$ alkyl), $OSO_2$($C_1$-$C_8$ haloalkyl), $C(=O)H$, $C(=O)$ ($C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, $(C_1$-$C_8$ alkyl)phenyl, $(C_1$-$C_8$ alkyl)-O-phenyl, $C(=O)$(Het-1), (Het-1), $(C_1$-$C_8$ alkyl)-(Het-1), $(C_1$-$C_8$ alkyl)-$C(=O)$—$(C_1$-$C_8$ alkyl), $(C_1$-$C_8$ alkyl)-$OC(=O)$—$(C_1$-$C_8$ alkyl), $(C_1$-$C_8$ alkyl)-O—$C(=O)O$—$(C_1$-$C_8$ alkyl), $(C_1$-$C_8$ alkyl)-$C(=O)$ (Het-1), $(C_1$-$C_8$ alkyl)-$C(=O)$(Het-1)$C(=O)O$—$(C_1$-$C_8$ alkyl), $(C_1$-$C_8$ alkyl)-$OC(=O)O$—$(C_1$-$C_8$ alkyl), $(C_1$-$C_8$ alkyl)-$OC(=O)$—$(C_1$-$C_8$ alkyl), $(C_1$-$C_8$ alkyl)-$OC(=O)$—($C_3$-$C_8$ cycloalkyl), $(C_1$-$C_8$ alkyl)-$OC(=O)$-(Het-1), $(C_1$-$C_8$ alkyl)-S-(Het-1), $(C_1$-$C_8$ alkyl)$S(=O)_n$(Het-1), or $(C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n$($C_3$-$C_8$ cycloalkyl), $S(=O)_n$($C_3$-$C_8$ halocycloalkyl), $S(=O)_n$($C_1$-$C_8$ alkyl), $S(=O)_n$($C_1$-$C_8$ haloalkyl), $OSO_2$($C_1$-$C_8$ alkyl), $OSO_2$($C_1$-$C_8$ haloalkyl), $C(=O)H$, $C(=O)OH$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, halophenyl, phenoxy, and (Het-1), or $R^x$ and $R^y$ together can optionally form a 5- to 7-membered saturated or unsaturated cyclic group which may contain one or more heteroatoms selected from nitrogen, sulfur, and oxygen, and where said cyclic group may be substituted with H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n$($C_3$-$C_8$ cycloalkyl), $S(=O)_n$($C_3$-$C_8$ halocycloalkyl), $S(=O)_n$($C_1$-$C_8$ alkyl), $S(=O)_n$($C_1$-$C_8$ haloalkyl), $OSO_2$($C_1$-$C_8$ alkyl), $OSO_2$($C_1$-$C_8$ haloalkyl), $C(=O)(C_1$-$C_8$ alkyl), $C(=O)O(C_1$-$C_8$ alkyl), $C(=O)(C_1$-$C_8$ haloalkyl), $C(=O)O$ ($C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n$ ($C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl) $C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, substituted phenyl, phenoxy, and (Het-1);

(M) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n$($C_3$-$C_8$ cycloalkyl), $S(=O)_n$($C_3$-$C_8$ halocycloalkyl), $S(=O)_n$($C_1$-$C_8$ alkyl), $S(=O)_n$($C_1$-$C_8$ haloalkyl), $OSO_2$($C_1$-$C_8$ alkyl), $OSO_2$($C_1$-$C_8$ haloalkyl), $C(=O)NR^xR^y$, $(C_1$-$C_8$ alkyl)$NR^xR^y$, $C(=O)$ ($C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$O(C_1$-$C_8$ haloalkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl) $C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, and phenoxy, wherein each alkyl, cycloalkyl, alkoxy, alkenyl, alkynyl, phenyl, and phenoxy may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n$($C_3$-$C_8$ cycloalkyl), $S(=O)_n$($C_3$-$C_8$ halocycloalkyl), $S(=O)_n$($C_1$-$C_8$ alkyl), $S(=O)_n$($C_1$-$C_8$ haloalkyl), $OSO_2$($C_1$-$C_8$ alkyl), $OSO_2$($C_1$-$C_8$ haloalkyl), $C(=O)H$, $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, and phenoxy; and (N) n is each individually 0, 1, or 2.

In some embodiments, the molecules provided have the structure of Formula One, Formula Two, or Formula Three:

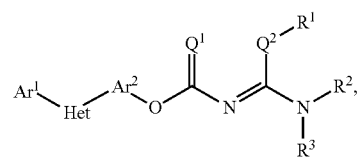

Formula One

-continued

Formula Two

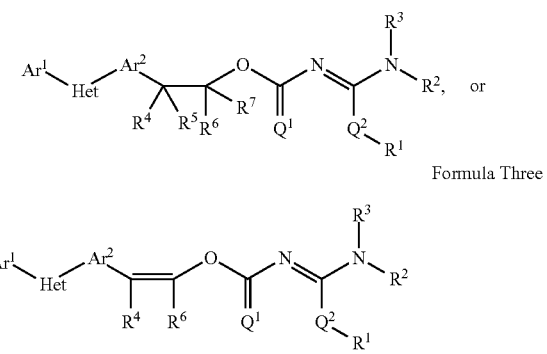

Formula Three wherein:
(A) $Ar^1$ is a phenyl or substituted phenyl having one or more substituents independently selected from $C_1$-$C_6$ alkyl, $C_1$-$C_6$ haloalkyl, $C_1$-$C_6$ alkoxy and $C_1$-$C_6$ haloalkoxy;
(B) Het is triazolyl;
(C) $Ar^2$ is a phenyl or a substituted phenyl having one or more substituents independently selected from H, F, Cl, Br, I, CN, $NO_2$, $NR^xR^y$, OH, $C_1$-$C_6$ alkyl, $C_1$-$C_6$ haloalkyl, $C_1$-$C_6$ alkoxy, and $C_1$-$C_6$ haloalkoxy;
(D1) Each $R^4$ and $R^6$ is selected from (E), H, F, Cl, Br, I, CN, oxo, $C_1$-$C_6$ alkyl, $C_1$-$C_6$ alkoxy, $C_1$-$C_6$ haloalkoxy, $C_2$-$C_6$ alkenyl, $C_2$-$C_6$ haloalkenyl, $C_2$-$C_6$ alkynyl, $C_1$-$C_6$ haloalkyl, $C_3$-$C_6$ cycloalkyl, $C_3$-$C_6$ cycloalkenyl, $C_3$-$C_6$ halocycloalkyl, and phenyl;
(D2) Each $R^5$ and $R^7$ is selected from, H, F, Cl, Br, I, CN, oxo, $C_1$-$C_6$ alkyl, $C_1$-$C_6$ alkoxy, $C_1$-$C_6$ haloalkoxy, $C_2$-$C_6$ alkenyl, $C_2$-$C_6$ haloalkenyl, $C_2$-$C_6$ alkynyl, $C_1$-$C_6$ haloalkyl, $C_3$-$C_6$ cycloalkyl, $C_3$-$C_6$ cycloalkenyl, $C_3$-$C_6$ halocycloalkyl, and phenyl;
(E) $R^4$ and $R^6$ together can optionally form a 3- to 7-membered saturated or unsaturated ring which may contain C=O, C=S, N, S or O, and is optionally substituted with H, OH, F, Cl, Br, I, $C_1$-$C_6$ alkyl, $C_1$-$C_6$ haloalkyl, $C_1$-$C_6$ alkoxy, $C_1$-$C_6$ haloalkoxy, phenyl, phenoxy, and Het-1;
(F) $Q^1$ is O;
(G) $Q^2$ is S;
(H) $R^1$ is selected from (J), H, $C_1$-$C_6$ alkyl or $C_2$-$C_6$ alkenyl, wherein said alkyl or alkenyl is optionally substituted with a $C_3$-$C_6$ cycloalkyl or $C_1$-$C_6$ alkoxy;
(F) $R^2$ is selected from (J), H, OH, $C_1$-$C_6$ alkyl or $C_2$-$C_6$ alkenyl, wherein said alkyl or alkenyl is optionally substituted with a $C_3$-$C_6$ cycloalkyl or $C_1$-$C_6$ alkoxy;
(G) $R^3$ is phenyl or (Het-1), wherein the phenyl or (Het-1) may be optionally substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_2$-$C_6$ alkenyl, $C_2$-$C_6$ haloalkenyl, $C_1$-$C_6$ alkoxy, $C_1$-$C_6$ haloalkoxy, $C_3$-$C_6$ cycloalkyl, $C_3$-$C_6$ halocycloalkyl, $S(=O)_n(C_1$-$C_6$ alkyl), $S(=O)_n(C_1$-$C_6$ haloalkyl), $(C_1$-$C_6$ alkyl)$O(C_1$-$C_6$ alkyl), $(C_1$-$C_6$ alkyl)$O(C_1$-$C_6$ haloalkyl), $(C_1$-$C_6$ alkyl)$S(=O)_n(C_1$-$C_6$ alkyl), phenyl, and oxo or wherein two adjacent substituents form a 5- or 6-membered saturated or unsaturated, hydrocarbyl link, which may contain one or more heteroatoms selected from nitrogen, sulfur, and oxygen, and such ring is optionally substituted with one or more substituents selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo;
(H) $R^x$ and $R^y$ are independently selected from H, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, and phenyl;
(I) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $(C_1$-$C_8$ alkyl)$O(C_1$-$C_8$ alkyl), $(C_1$-$C_8$ alkyl)$O(C_1$-$C_8$ haloalkyl), $S(=O)_n(C_1$-$C_6$ alkyl), $S(=O)_n(C_1$-$C_6$ haloalkyl), phenyl, and oxo; and
(J) $R^1$ and $R^2$ may be a 1- to 4-membered saturated or unsaturated, hydrocarbyl link, which may contain one or more heteroatoms selected from nitrogen, sulfur, and oxygen, and together with $(Q^2)(C)(N)$ forms a 4- to 7-membered cyclic structure, wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo.

In one embodiment, $Ar^1$ is substituted phenyl having one or more substituents independently selected from $OCF_3$, $OCF_2CF_3$, and $CF_3$. In another embodiment, Het is 1,2,4-triazolyl. In another embodiment, $Ar^2$ is phenyl.

In another embodiment, $R^1$ and $R^2$ together form a 5-membered saturated or unsaturated ring containing one or two C=O, and such ring is optionally substituted with H, OH, F, Cl, Br, I, CN, $C_1$-$C_6$ alkyl, $C_1$-$C_6$ haloalkyl, $C_1$-$C_6$ alkoxy, $C_1$-$C_6$ haloalkoxy, phenyl or phenoxy. In another embodiment, $R^3$ is substituted phenyl with one or more substituents independently selected from H, OH, F, Cl, Br, I, $C_1$-$C_6$ alkyl, $C_1$-$C_6$ haloalkyl, $C_2$-$C_6$ alkenyl, $C_2$-$C_6$ haloalkenyl, $(C_1$-$C_6$ alkyl)$O(C_1$-$C_6$ alkyl), $(C_1$-$C_6$ alkyl)$O(C_1$-$C_6$ haloalkyl), $(C_1$-$C_6$ alkyl)$S(=O)_n(C_1$-$C_6$ alkyl), $C_3$-$C_6$ cycloalkyl, $C_3$-$C_6$ halocycloalkyl, $C_1$-$C_6$ alkoxy, $C_1$-$C_6$ haloalkoxy. In another embodiment, $R^3$ is substituted phenyl wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo.

In another aspect, provided is a process to apply a molecule provided herein. The process comprises applying a molecule provided herein, to an area to control a pest, in an amount sufficient to control such pest. In one embodiment, the pest is beet armyworm (BAW), cabbage looper (CL), or green peach aphid (GPA).

In another aspect, provided is a molecule that is a pesticidally acceptable acid addition salt, a salt derivative, a solvate, or an ester derivative, of a molecule provided herein. In another aspect, provided is a molecule provided herein wherein at least one H is $^2H$ or at least one C is $^{14}C$. In another aspect, provided is a composition comprising a molecule provided herein and at least one other compound having insecticidal, herbicidal, acaricidal, nematicidal, or fungicidal activity. In another aspect, provided is a composition comprising a molecule provided herein and a seed.

In another aspect, provided is a process comprising applying a molecule provided herein to a genetically modified plant or a genetically-modified seed, which has been genetically modified to express one or more specialized traits. In another aspect, provided is a process comprising: orally administering or topically applying a molecule provided herein, to a non-human animal, to control endoparasites, ectoparasites, or both.

DETAILED DESCRIPTION OF THE INVENTION

The examples given for the substituents are (except for halo) non-exhaustive and must not be construed as limiting the invention disclosed in this document.

Definitions

"Alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"Alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"Alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"Alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"Alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"Alkynyloxy" means an alkynyl further consisting of a carbon-oxygen single bond, for example, pentynyloxy, hexynyloxy, heptynyloxy, octynyloxy, nonynyloxy, and decynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2] octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"Halo" means fluoro, chloro, bromo, and iodo.

"Haloalkyl" means an alkyl further consisting of, from one to the maximum possible number of, identical or different, halos, for example, fluoromethyl, difluoromethyl, trifluoromethyl, 1-fluoroethyl, 2-fluoroethyl, 2,2,2-trifluoroethyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3, 4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

Compounds

The compounds of this invention have the structure of Formula A:

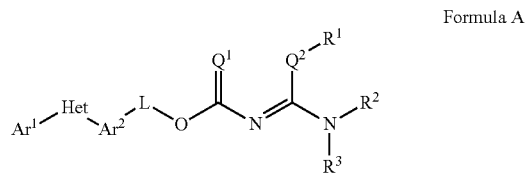

Formula A wherein:
(A) $Ar^1$ is selected from
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, or $S(=O)_nNR^xR^y$, or (Het-1),
wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)NR$^x$R$^y$, (C$_1$-C$_8$ alkyl)NR$^x$R$^y$, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)OC$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, phenoxy, Si(C$_1$-C$_8$ alkyl)$_3$, S(=O)$_n$NR$^x$R$^y$, or (Het-1);

(B) Het is a 5- or 6-membered, saturated or unsaturated, heterocyclic ring, containing one or more heteroatoms independently selected from nitrogen, sulfur, or oxygen, and where Ar$^1$ and Ar$^2$ are not ortho to each other (but may be meta or para, such as, for a five-membered ring they are 1,3 and for a 6-membered ring they are either 1,3 or 1,4) and where said heterocyclic ring may also be substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)NR$^x$R$^y$, (C$_1$-C$_8$ alkyl)NR$^x$R$^y$, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, phenoxy, Si(C$_1$-C$_8$ alkyl)$_3$, or S(=O)$_n$NR$^x$R$^y$, wherein each alkyl, haloalkyl, cycloalkyl, halocycloalkyl, alkoxy, haloalkoxy, alkenyl, cycloalkenyl, haloalkenyl, alkynyl, phenyl, and phenoxy substituent may be optionally substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)NR$^x$R$^y$, (C$_1$-C$_8$ alkyl)NR$^x$R$^y$, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, phenoxy, Si(C$_1$-C$_8$ alkyl)$_3$, or S(=O)$_n$NR$^x$R$^y$;

(C) Ar$^2$ is selected from (1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)NR$^x$R$^y$, (C$_1$-C$_8$ alkyl)NR$^x$R$^y$, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, phenoxy, Si(C$_1$-C$_8$ alkyl)$_3$, S(=O)$_n$NR$^x$R$^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)NR$^x$R$^y$, (C$_1$-C$_8$ alkyl)NR$^x$R$^y$, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, phenoxy, Si(C$_1$-C$_8$ alkyl)$_3$, S(=O)$_n$NR$^x$R$^y$, or (Het-1);

(D) L is linker selected from (1) a bond, (2) —CR$^4$R$^5$—CR$^6$R$^7$—, or (3) —CR$^4$=CR$^6$—, wherein each of R$^4$, R$^5$, R$^6$, and R$^7$ is selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_1$-C$_8$ alkoxy, C$_1$-C$_8$ haloalkoxy, $C_2$-$C_8$ alkenyl, $C_2$-$C_8$ haloalkenyl, $C_2$-$C_8$ alkynyl, $C_2$-$C_8$ haloalkynyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_3$-$C_8$ cycloalkenyl, $C_3$-$C_8$ halocycloalkenyl, C(=O)($C_1$-$C_6$ alkyl), C(=O)O($C_1$-$C_6$ alkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S(=O)$_n$($C_1$-$C_6$ alkyl), C(=O)($C_1$-$C_6$ alkyl)C(=O)O($C_1$-$C_6$ alkyl), S(=O)$_n$($C_1$-$C_8$ alkyl), S(=O)$_n$($C_3$-$C_8$ cycloalkyl), S(=O)$_n$($C_1$-$C_8$ haloalkyl), S(=O)$_n$($C_3$-$C_8$ halocycloalkyl), phenyl, or phenoxy;

(E) $R^4$ and $R^6$ together can optionally form a 3- to 7-membered ring which may contain C=O, C=S, N, S or O, and is optionally substituted with OH, F, Cl, Br, I, CN, NO$_2$, NR$^x$R$^y$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $C_3$-$C_6$ cycloalkynyl, S(=O)$_n$($C_1$-$C_6$ alkyl), S(=O)$_n$($C_1$-$C_6$ haloalkyl), OSO$_2$($C_1$-$C_6$ alkyl), OSO$_2$($C_1$-$C_6$ haloalkyl), C(=O)H, C(=O)OH, C(=O)NR$^x$R$^y$, ($C_1$-$C_6$ alkyl)NR$^x$R$^y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S(=O)$_n$($C_1$-$C_6$ alkyl), C(=O)($C_1$-$C_6$ alkyl)C(=O)O($C_1$-$C_6$ alkyl), phenyl, phenoxy, and Het-1;

(F) $Q^1$ is selected from O or S;

(G) $Q^2$ is selected from O or S;

(H) $R^1$ is selected from (J), H, $C_1$-$C_8$ alkyl, $C_3$-$C_8$ cycloalkyl, $C_2$-$C_8$ alkenyl, $C_2$-$C_8$ alkynyl, C(=O)($C_1$-$C_8$ alkyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(=O)NR$^x$R$^y$, ($C_1$-$C_8$ alkyl)-C(=O)N(R$^x$)($C_1$-$C_8$ alkyl)-(Het-1), ($C_1$-$C_8$ alkyl)-C(=O)(Het-1), ($C_1$-$C_8$ alkyl)-C(=O)N(R$^x$)($C_1$-$C_8$ alkyl)N(R$^y$)C(=O)OH, ($C_1$-$C_8$ alkyl)-C(=O)N(R$^x$)($C_1$-$C_8$ alkyl)N(R$^x$)(R$^y$), ($C_1$-$C_8$ alkyl)-C(=O)N(R$^x$)($C_1$-$C_8$ alkyl)N(R$^y$)C(=O)O—($C_1$-$C_8$ alkyl), ($C_1$-$C_8$ alkyl)-C(=O)N(R$^x$)($C_1$-$C_8$ alkyl)(N(R$^y$)C(=O)O—($C_1$-$C_8$ alkyl)C(=O)OH, ($C_1$-$C_8$ alkyl)-C(=O)(Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(=O)-(Het-1), ($C_1$-$C_8$ alkyl)-OC(=O)—($C_1$-$C_8$ alkyl)N(R$^x$)C(=O)O—($C_1$-$C_8$ alkyl), ($C_1$-$C_8$ alkyl)-NR$^x$R$^y$, ($C_1$-$C_8$ alkyl)-S-(Het-1), ($C_1$-$C_8$ alkyl)S(=O)$_n$(Het-1), or ($C_1$-$C_8$ alkyl)-O-(Het-1), wherein each alkyl, cycloalkyl, phenyl, and (Het-1) are optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)OH, C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(I) $R^2$ is selected from (J), H, OH, SH, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(=O)NR$^x$R$^y$, ($C_1$-$C_8$ alkyl)-C(=O)N(R$^x$)($C_1$-$C_8$ alkyl)-(Het-1), ($C_1$-$C_8$ alkyl)-C(=O)(Het-1), ($C_1$-$C_8$ alkyl)-C(=O)N(R$^x$)($C_1$-$C_8$ alkyl)N(R$^y$)C(=O)OH, ($C_1$-$C_8$ alkyl)-C(=O)N(R$^x$)($C_1$-$C_8$ alkyl)N(R$^x$)(R$^y$), ($C_1$-$C_8$ alkyl)-C(=O)N(R$^x$)($C_1$-$C_8$ alkyl)N(R$^y$)C(=O)O—($C_1$-$C_8$ alkyl), ($C_1$-$C_8$ alkyl)-C(=O)N(R$^x$)($C_1$-$C_8$ alkyl)(N(R$^y$)C(=O)O—($C_1$-$C_8$ alkyl)C(=O)OH, ($C_1$-$C_8$ alkyl)-C(=O)(Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(=O)-(Het-1), ($C_1$-$C_8$ alkyl)-OC(=O)—($C_1$-$C_8$ alkyl)N(R$^x$)C(=O)O—($C_1$-$C_8$ alkyl), ($C_1$-$C_8$ alkyl)-NR$^x$R$^y$, ($C_1$-$C_8$ alkyl)-S-(Het-1), ($C_1$-$C_8$ alkyl)S(=O)$_n$(Het-1), or ($C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, NO$_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)OH, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, halophenyl, phenoxy, and (Het-1);

(J) $R^1$ and $R^2$ may be a 1- to 4-membered saturated or unsaturated, hydrocarbyl link, which may contain one or more heteroatoms selected from nitrogen, sulfur, and oxygen, and together with ($Q^2$)(C)(N) forms a 4- to 7-membered cyclic structure, wherein said hydrocarbyl link may optionally be substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)H$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, substituted phenyl, phenoxy, or (Het-1);

(K) $R^3$ is selected from $C_3$-$C_8$ cycloalkyl, phenyl, $(C_1$-$C_8$ alkyl)phenyl, $(C_1$-$C_8$ alkyl)-O-phenyl, $(C_2$-$C_8$ alkenyl)-O-phenyl, (Het-1), $(C_1$-$C_8$ alkyl)-(Het-1), $(C_1$-$C_8$ alkyl)-O-(Het-1), wherein the $C_3$-$C_8$ cycloalkyl, phenyl, $(C_1$-$C_8$ alkyl)phenyl, $(C_1$-$C_8$ alkyl)-O-phenyl, $(C_2$-$C_8$ alkenyl)-O-phenyl, (Het-1), $(C_1$-$C_8$ alkyl)-(Het-1), or $(C_1$-$C_8$ alkyl)-O-(Het-1) may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$O(C_1$-$C_8$ haloalkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, $S(=O)_nNR^xR^y$, or (Het-1) or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo;

(L) $R^x$ and $R^y$ are independently selected from H, OH, SH, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)H$, $C(=O)(C_1$-$C_8$ alkyl), $C(=O)O(C_1$-$C_8$ alkyl), $C(=O)(C_1$-$C_8$ haloal-kyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, $(C_1$-$C_8$ alkyl)phenyl, $(C_1$-$C_8$ alkyl)-O-phenyl, $C(=O)(Het-1)$, (Het-1), $(C_1$-$C_8$ alkyl)-(Het-1), $(C_1$-$C_8$ alkyl)-C(=O)—(C_1$-$C_8$ alkyl), $(C_1$-$C_8$ alkyl)-OC(=O)—(C_1$-$C_8$ alkyl), $(C_1$-$C_8$ alkyl)-O—C(=O)O—(C_1$-$C_8$ alkyl), $(C_1$-$C_8$ alkyl)-C(=O)(Het-1), $(C_1$-$C_8$ alkyl)-C(=O)(Het-1)C(=O)O—(C_1$-$C_8$ alkyl), $(C_1$-$C_8$ alkyl)-OC(=O)O—(C_1$-$C_8$ alkyl), $(C_1$-$C_8$ alkyl)-OC(=O)—(C_1$-$C_8$ alkyl), $(C_1$-$C_8$ alkyl)-OC(=O)—(C_3$-$C_8$ cycloalkyl), $(C_1$-$C_8$ alkyl)-OC(=O)-(Het-1), $(C_1$-$C_8$ alkyl)-S-(Het-1), $(C_1$-$C_8$ alkyl)$S(=O)_n(Het-1), or $(C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)H$, $C(=O)OH$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, halophenyl, phenoxy, and (Het-1), or $R^x$ and $R^y$ together can optionally form a 5- to 7-membered saturated or unsaturated cyclic group which may contain one or more heteroatoms selected from nitrogen, sulfur, and oxygen, and where said cyclic group may be substituted with H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, substituted phenyl, phenoxy, and (Het-1);

(M) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)$NR^xR^y$, ($C_1$-$C_8$ alkyl)$NR^xR^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)O($C_1$-$C_8$ haloalkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, and phenoxy, wherein each alkyl, cycloalkyl, alkoxy, alkenyl, alkynyl, phenyl, and phenoxy may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)H, C(=O)$NR^xR^y$, ($C_1$-$C_8$ alkyl)$NR^xR^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, and phenoxy; and (N) n is each individually 0, 1, or 2.

In one embodiment, $Ar^1$ is phenyl or substituted phenyl having one or more substituents independently selected from $C_1$-$C_6$ alkyl, $C_1$-$C_6$ haloalkyl, and $C_1$-$C_6$ haloalkoxy.

In another embodiment, Het is a triazolyl, imidazolyl, pyrrolyl, or pyrazolyl.

In another embodiment, $Ar^2$ is phenyl or a substituted phenyl having one or more substituents independently selected from $C_1$-$C_6$ alkyl, $C_1$-$C_6$ haloalkyl, and $C_1$-$C_6$ haloalkoxy.

In another embodiment, $R^1$ and $R^2$ are independently selected from H, $C_1$-$C_6$ alkyl, $C_1$-$C_6$ alkoxy, $C_1$-$C_6$ haloalkyl, $C_1$-$C_6$ haloalkoxy, phenyl, or phenoxy;

wherein $R^1$ and $R^2$ together can optionally form a 5- to 7-membered ring and is optionally substituted with OH, F, Cl, Br, I, CN, $NO_2$, $C_1$-$C_6$ alkyl, $C_1$-$C_6$ alkoxy, $C_1$-$C_6$ haloalkyl, $C_1$-$C_6$ haloalkoxy, phenyl, phenoxy, or (Het-1), wherein (Het-1) is a 5- or 6-membered, saturated or unsaturated, heterocyclic ring, containing one or more heteroatoms independently selected from nitrogen, sulfur and oxygen.

In another embodiment, $R^1$ and $R^2$ together form a 5- to 7-membered ring containing one or more C=O, C=S, N, S or O, and such ring is optionally substituted with H, OH, F, Cl, Br, I, $C_1$-$C_6$ alkyl, $C_1$-$C_6$ haloalkyl, $C_1$-$C_6$ alkoxy, $C_1$-$C_6$ haloalkoxy, phenyl, or phenoxy, wherein said phenyl or phenoxy is optionally substituted with one or more H, OH, F, Cl, Br, I, $C_1$-$C_6$ alkyl, $C_1$-$C_6$ haloalkyl, $C_1$-$C_6$ alkoxy, $C_1$-$C_6$ haloalkoxy, or phenyl.

In another embodiment, $R^1$ and $R^2$ together form a 5- to 7-membered ring which contains one or more C=O, C=S, N, S or O.

In another embodiment, $R^3$ is phenyl optionally substituted with one or more substituents independently selected from H, OH, F, Cl, Br, I, $C_1$-$C_6$ alkyl, $C_1$-$C_6$ haloalkyl, $C_1$-$C_6$ alkoxy, $C_1$-$C_6$ haloalkoxy, $C_1$-$C_6$ alkyl, $C_1$-$C_6$ haloalkyl, $C_1$-$C_6$ alkenyl, $C_1$-$C_6$ haloalkenyl, $C_3$-$C_6$ cycloalkyl, $C_3$-$C_6$ halocycloalkyl, $NR^xR^y$, ($C_1$-$C_8$ alkyl)O($C_1$-$C_8$ alkyl), ($C_1$-$C_8$ alkyl)O($C_1$-$C_8$ haloalkyl), ($C_1$-$C_8$ alkyl)S(=O)$_n$($C_1$-$C_8$ alkyl), phenyl, or phenoxy. In another embodiment, $R^3$ is phenyl optionally substituted wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, S(=O)$_n$($C_1$-$C_6$ alkyl), S(=O)$_n$($C_1$-$C_6$ haloalkyl), phenyl, and oxo.

In another embodiment, $Ar^1$ is substituted phenyl having one or more substituents independently selected from $OCF_3$, $OCF_2CF_3$, and $CF_3$.

In another embodiment, Het is substituted pyrazolyl wherein said substituted pyrazolyl has one or more substituents independently selected from H, C(=O)O($C_1$-$C_6$ alkyl), or C(=O)$NR^xR^y$.

In another embodiment, Het is 1,2,4-triazolyl.

In another embodiment, $Ar^2$ is phenyl.

In another embodiment, $Ar^2$ is substituted phenyl having one or more substituents independently selected from H, F, Cl, Br, I, CN, $C_1$-$C_6$ alkyl, and $C_1$-$C_6$ alkoxy.

In another embodiment, $R^1$ is H or $C_1$-$C_6$ alkyl.

In another embodiment, $R^2$ is H or $C_1$-$C_6$ alkyl.

In another embodiment, each $R^4$, $R^5$, $R^6$, or $R^7$ is independently H, F, Cl, or $C_1$-$C_6$ alkyl.

In another embodiment, each $R^4$, $R^5$, $R^6$, or $R^7$ is independently H or a $C_1$-$C_6$ alkyl.

In another embodiment, each $R^4$, $R^5$, $R^6$, or $R^7$ is independently H, F or Cl.

In another embodiment, each of $R^1$ and $R^2$ is independently H or a $C_1$-$C_6$ alkyl.

In another embodiment, $R^1$ and $R^2$ together form a 5-membered saturated or unsaturated ring containing one or two C=O, and such ring is optionally substituted with H, OH, F, Cl, Br, I, CN, $C_1$-$C_6$ alkyl, $C_1$-$C_6$ haloalkyl, $C_1$-$C_6$ alkoxy, $C_1$-$C_6$ haloalkoxy, phenyl or phenoxy.

In another embodiment, $R^3$ is substituted phenyl with one or more OH, F, Cl, Br, I, $C_1$-$C_6$ alkyl, $C_1$-$C_6$ haloalkyl, $C_1$-$C_6$ alkenyl, $C_1$-$C_6$ haloalkenyl, $C_3$-$C_6$ cycloalkyl, $C_3$-$C_6$ halocycloalkyl, $NR^xR^y$, ($C_1$-$C_8$ alkyl)O($C_1$-$C_8$ alkyl), ($C_1$-$C_8$ alkyl)O($C_1$-$C_8$ haloalkyl), $C_1$-$C_6$ alkoxy, or $C_1$-$C_6$ haloalkoxy.

In another embodiment, the molecule has a structure selected from compounds listed in Table 1 below:

TABLE 1

Structures for Compounds

A1

A2

A3

A4

A5

A6

TABLE 1-continued
Structures for Compounds
A7 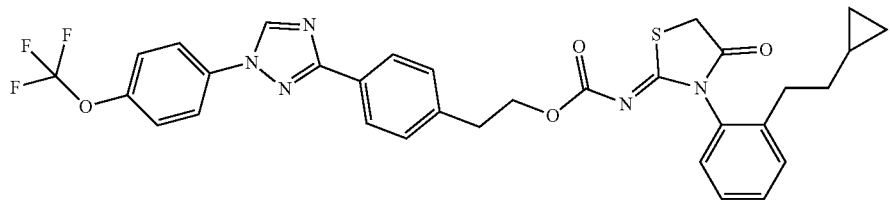 [SMILES: O=C(/N=C1\SCC(=O)N1c1ccccc1CCC1CC1)OCCc1ccc(-c2ncn(-c3ccc(OC(F)(F)F)cc3)n2)cc1]
A8 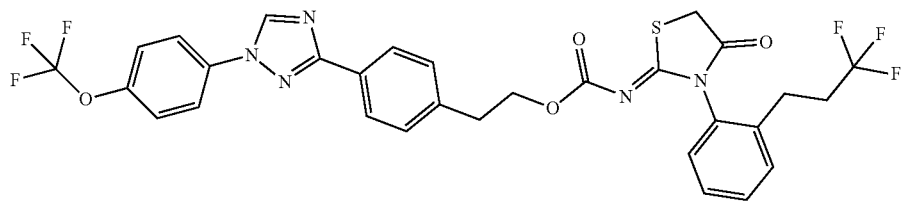 [SMILES: O=C(/N=C1\SCC(=O)N1c1ccccc1CCC(F)(F)F)OCCc1ccc(-c2ncn(-c3ccc(OC(F)(F)F)cc3)n2)cc1]
A9 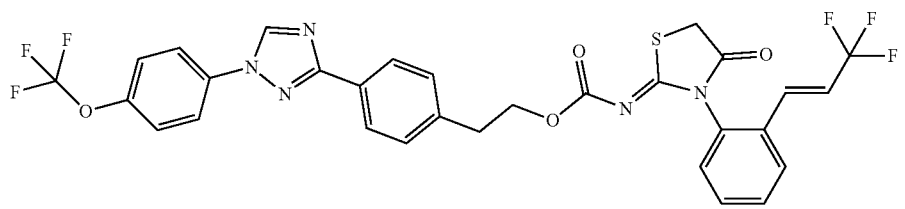 [SMILES: O=C(/N=C1\SCC(=O)N1c1ccccc1/C=C/C(F)(F)F)OCCc1ccc(-c2ncn(-c3ccc(OC(F)(F)F)cc3)n2)cc1]
A10 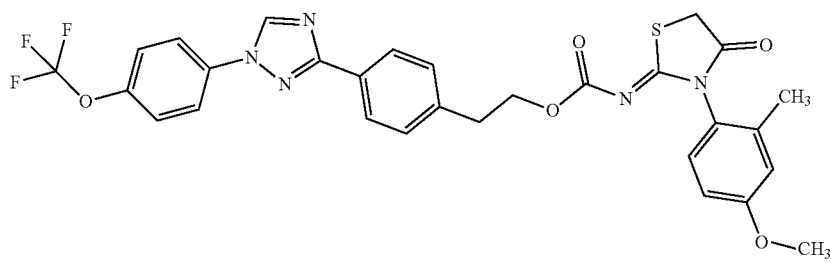 [SMILES: COc1ccc(N2C(=O)CS/C2=N\C(=O)OCCc2ccc(-c3ncn(-c4ccc(OC(F)(F)F)cc4)n3)cc2)c(C)c1]
A11 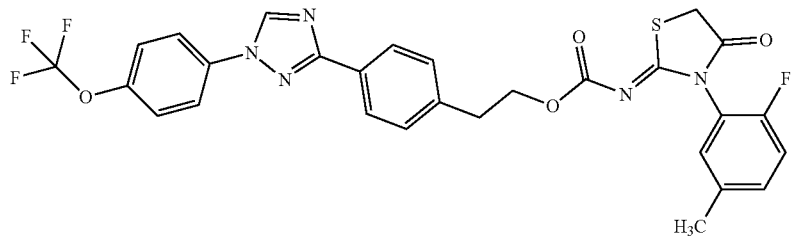 [SMILES: Cc1ccc(F)c(N2C(=O)CS/C2=N\C(=O)OCCc2ccc(-c3ncn(-c4ccc(OC(F)(F)F)cc4)n3)cc2)c1]
A12 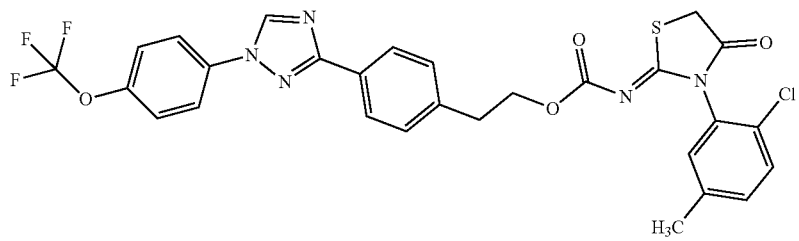 [SMILES: Cc1ccc(Cl)c(N2C(=O)CS/C2=N\C(=O)OCCc2ccc(-c3ncn(-c4ccc(OC(F)(F)F)cc4)n3)cc2)c1]

TABLE 1-continued
Structures for Compounds
A13 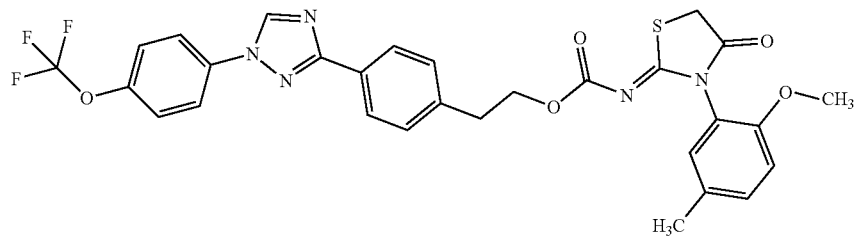 [SMILES: COc1ccc(C)cc1N1C(=O)CS/C1=N\C(=O)OCCc1ccc(-c2ncn(-c3ccc(OC(F)(F)F)cc3)n2)cc1]
A14 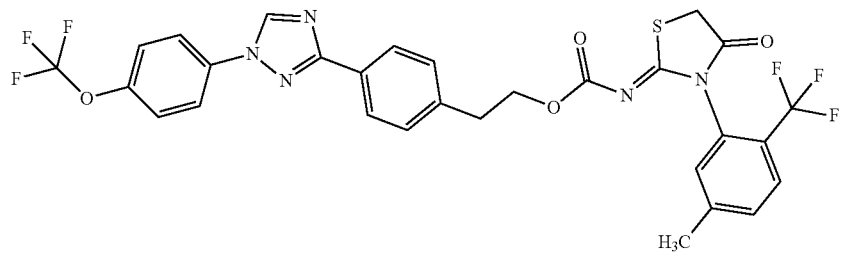 [SMILES: Cc1ccc(C(F)(F)F)c(N2C(=O)CS/C2=N\C(=O)OCCc2ccc(-c3ncn(-c4ccc(OC(F)(F)F)cc4)n3)cc2)c1]
A15 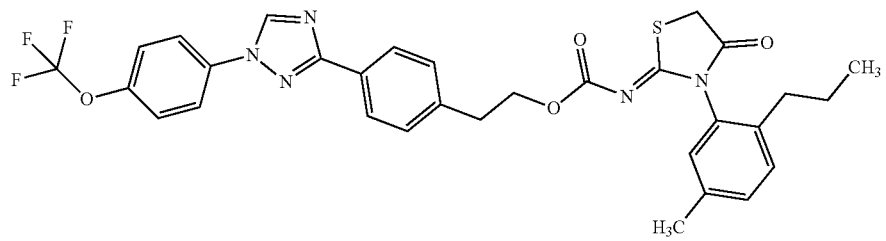
A16 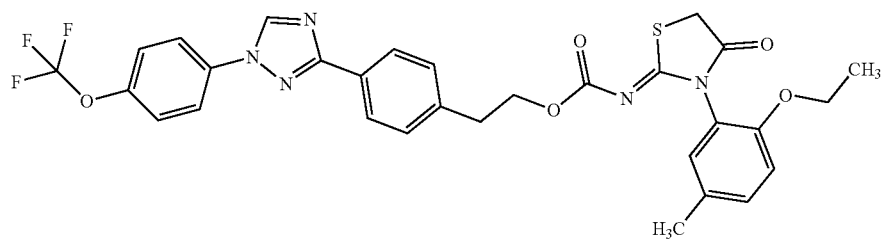
A17 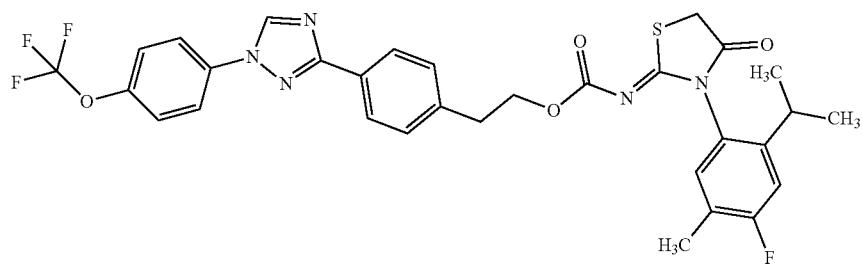 [SMILES: Cc1cc(N2C(=O)CS/C2=N\C(=O)OCCc2ccc(-c3ncn(-c4ccc(OC(F)(F)F)cc4)n3)cc2)c(C(C)C)cc1F]
A18 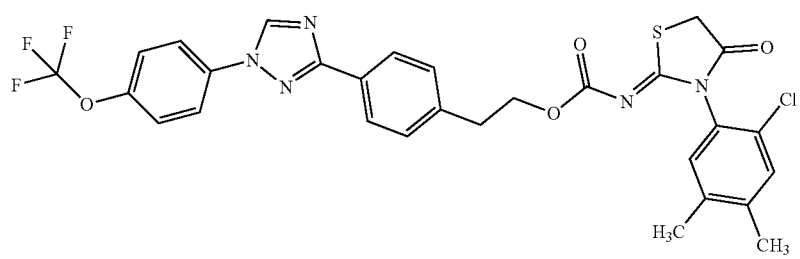 [SMILES: Cc1cc(Cl)c(N2C(=O)CS/C2=N\C(=O)OCCc2ccc(-c3ncn(-c4ccc(OC(F)(F)F)cc4)n3)cc2)cc1C]

TABLE 1-continued
Structures for Compounds
A19 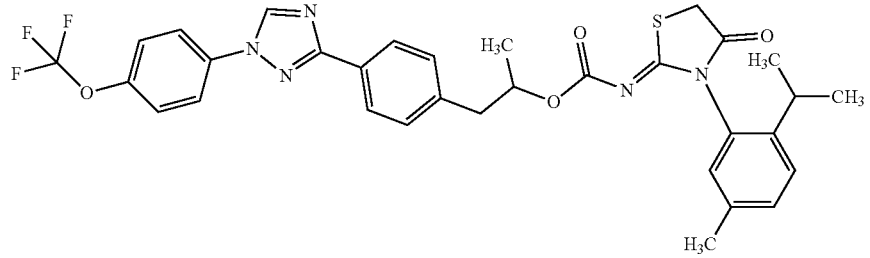 [SMILES: Cc1ccc(C(C)C)c(N2C(=O)CS/C2=N\C(=O)OC(C)Cc2ccc(-c3ncn(-c4ccc(OC(F)(F)F)cc4)n3)cc2)c1]
A20 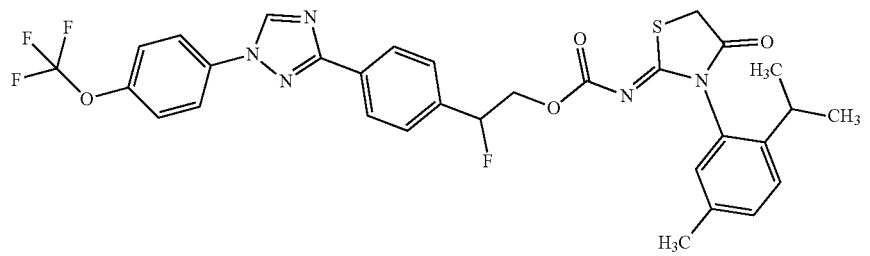
A21 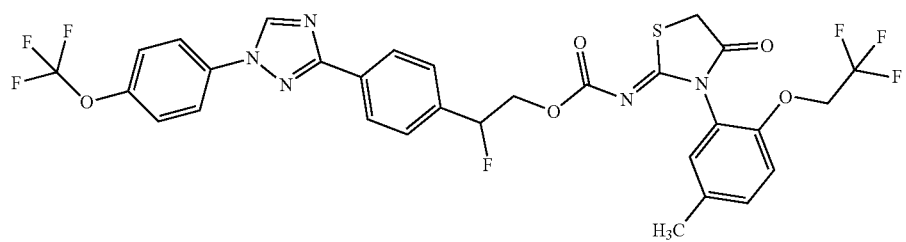 [SMILES: Cc1ccc(OCC(F)(F)F)c(N2C(=O)CS/C2=N\C(=O)OCC(F)c2ccc(-c3ncn(-c4ccc(OC(F)(F)F)cc4)n3)cc2)c1]
A22 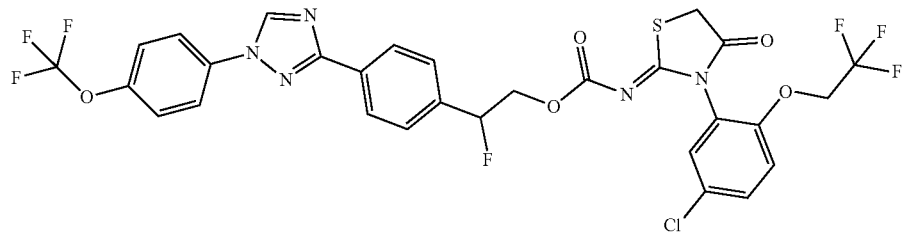 [SMILES: O=C(/N=C1\SCC(=O)N1c1cc(Cl)ccc1OCC(F)(F)F)OCC(F)c1ccc(-c2ncn(-c3ccc(OC(F)(F)F)cc3)n2)cc1]
A23 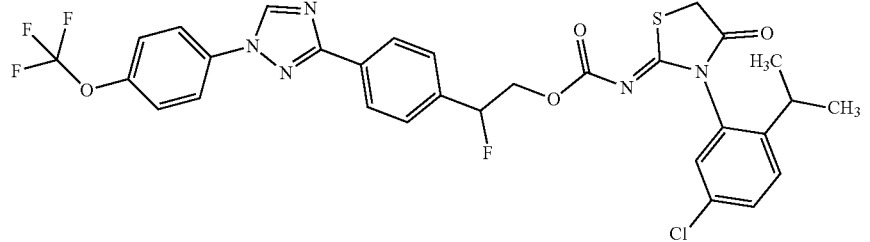 [SMILES: CC(C)c1ccc(Cl)cc1N1C(=O)CS/C1=N\C(=O)OCC(F)c1ccc(-c2ncn(-c3ccc(OC(F)(F)F)cc3)n2)cc1]
A24 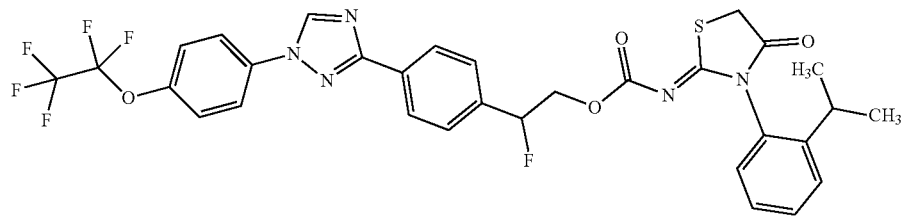 [SMILES: CC(C)c1ccccc1N1C(=O)CS/C1=N\C(=O)OCC(F)c1ccc(-c2ncn(-c3ccc(OC(F)(F)C(F)(F)F)cc3)n2)cc1]

TABLE 1-continued
Structures for Compounds
A25 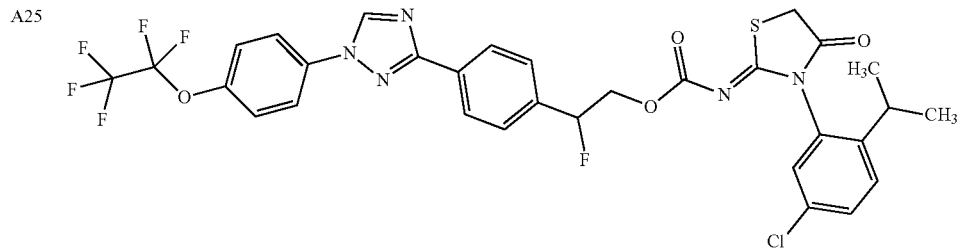
A26 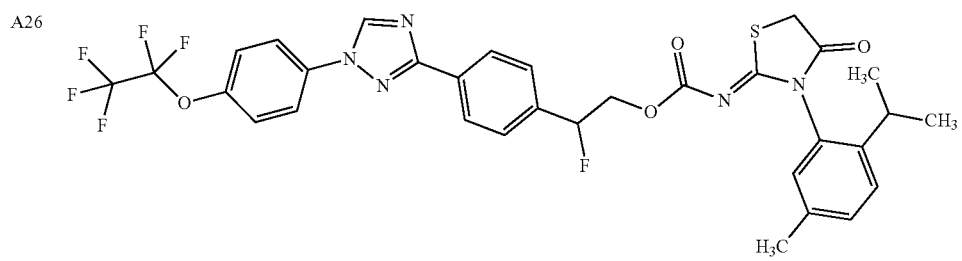
A27 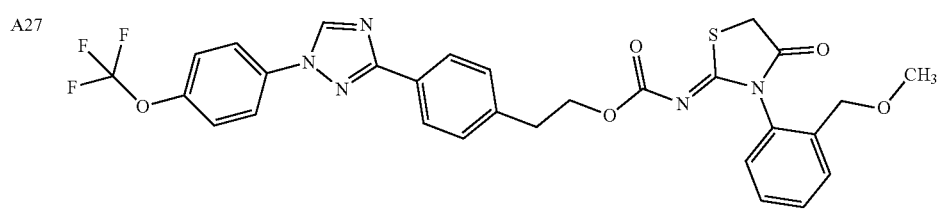
A28 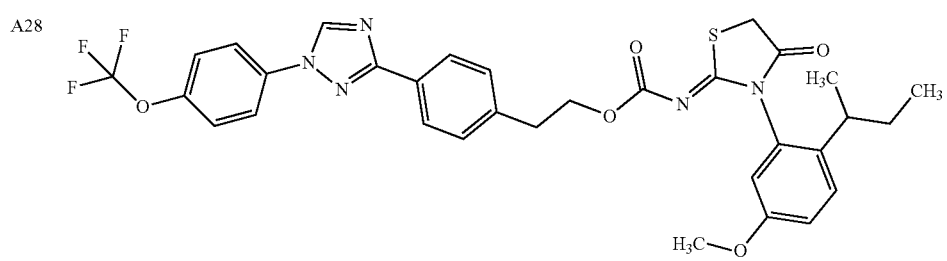
A29 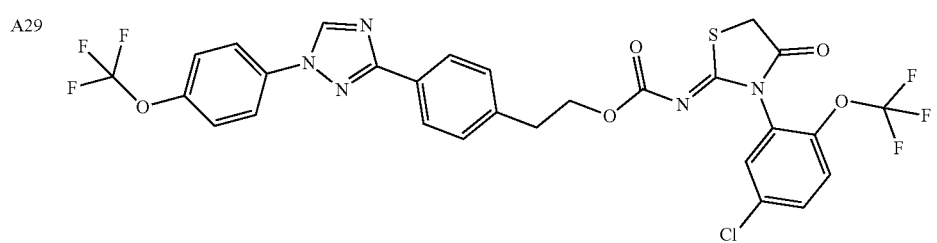
A30 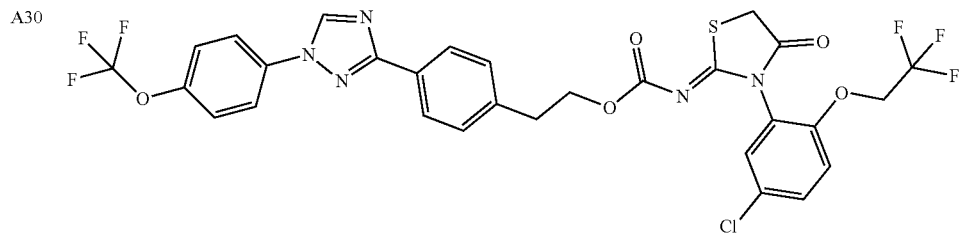

TABLE 1-continued

Structures for Compounds

TABLE 1-continued
Structures for Compounds
A37 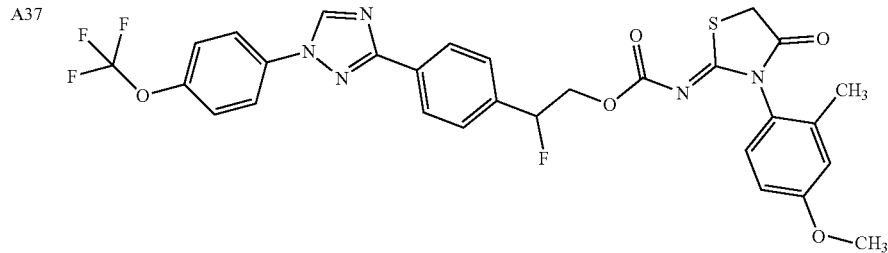
A38 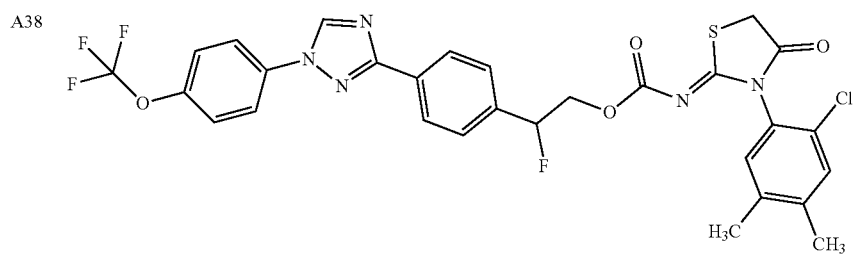
A39 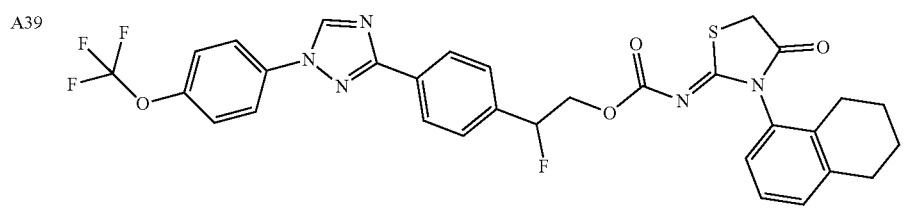
A40 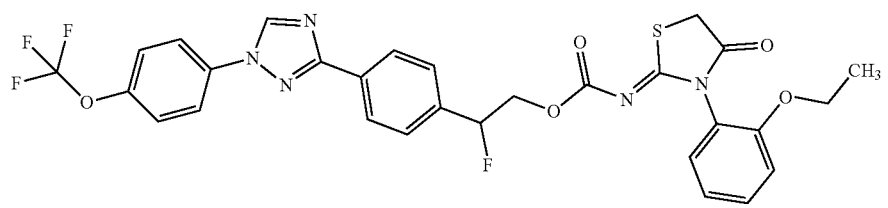 [SMILES: CCOc1ccccc1N1C(=O)CS/C1=N\C(=O)OCC(F)c1ccc(-c2ncn(-c3ccc(OC(F)(F)F)cc3)n2)cc1]
A41 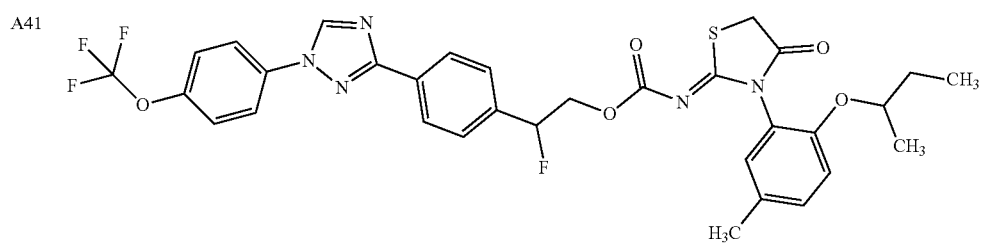
A42 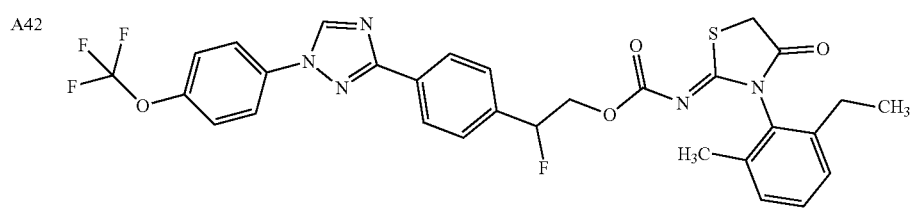

TABLE 1-continued
Structures for Compounds
A43 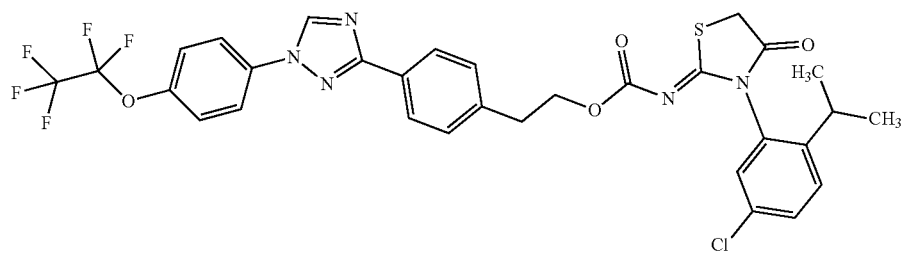 [SMILES: CC(C)c1ccc(Cl)cc1N1C(=O)CS/C1=N\C(=O)OCCc1ccc(-c2ncn(-c3ccc(OC(F)(F)C(F)(F)F)cc3)n2)cc1]
A44 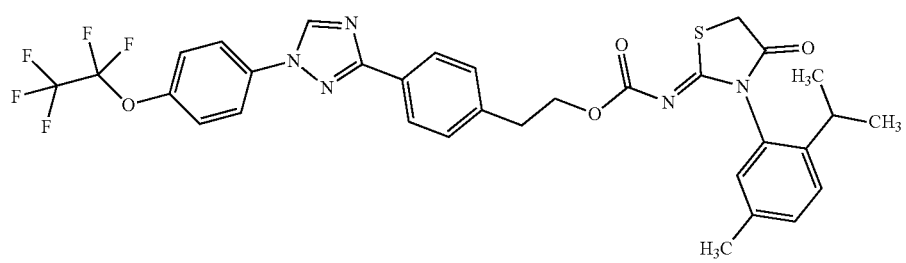 [SMILES: Cc1ccc(C(C)C)c(N2C(=O)CS/C2=N\C(=O)OCCc2ccc(-c3ncn(-c4ccc(OC(F)(F)C(F)(F)F)cc4)n3)cc2)c1]
A45 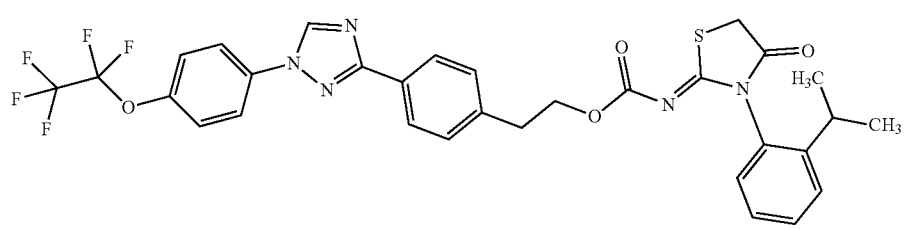 [SMILES: CC(C)c1ccccc1N1C(=O)CS/C1=N\C(=O)OCCc1ccc(-c2ncn(-c3ccc(OC(F)(F)C(F)(F)F)cc3)n2)cc1]
A46 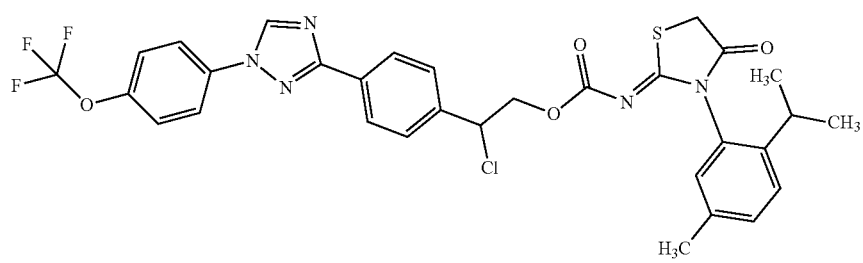 [SMILES: Cc1ccc(C(C)C)c(N2C(=O)CS/C2=N\C(=O)OCC(Cl)c2ccc(-c3ncn(-c4ccc(OC(F)(F)F)cc4)n3)cc2)c1]
A47 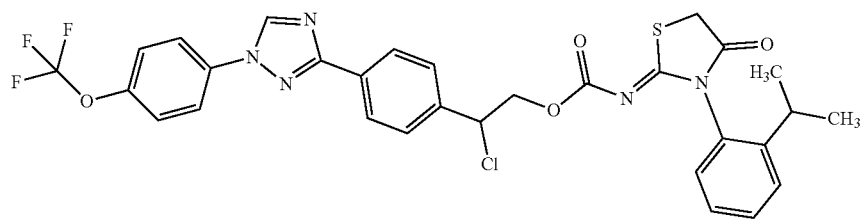 [SMILES: CC(C)c1ccccc1N1C(=O)CS/C1=N\C(=O)OCC(Cl)c1ccc(-c2ncn(-c3ccc(OC(F)(F)F)cc3)n2)cc1]
A48 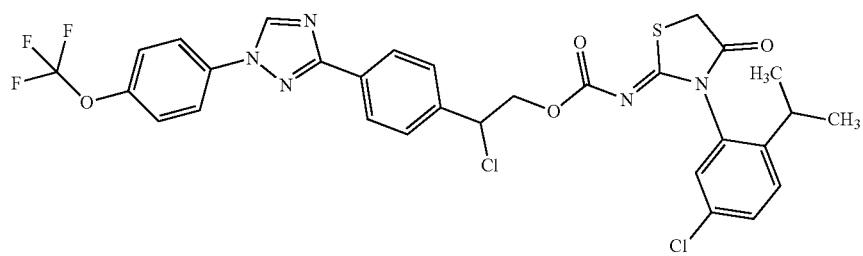

TABLE 1-continued
Structures for Compounds
A49 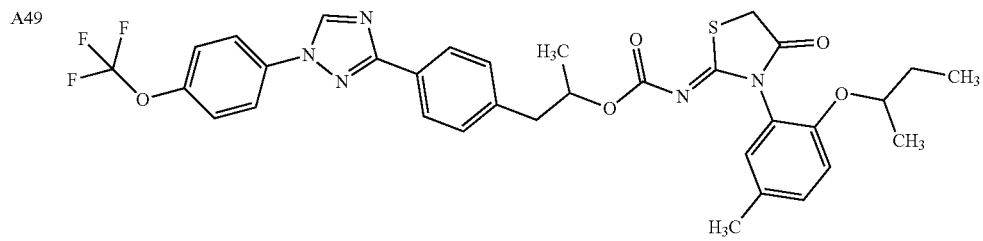
A50 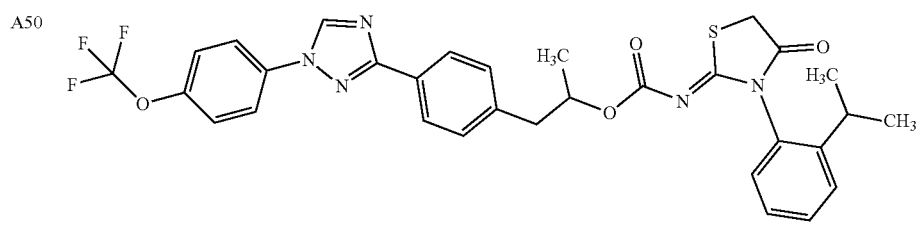
A51 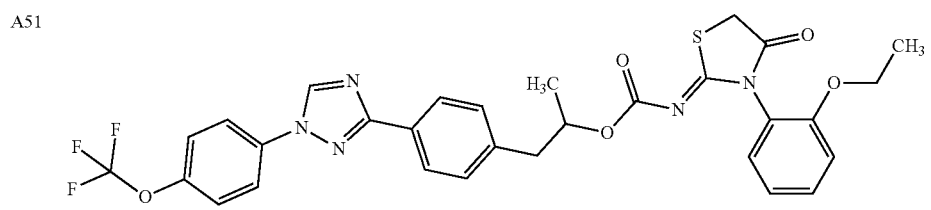
A52 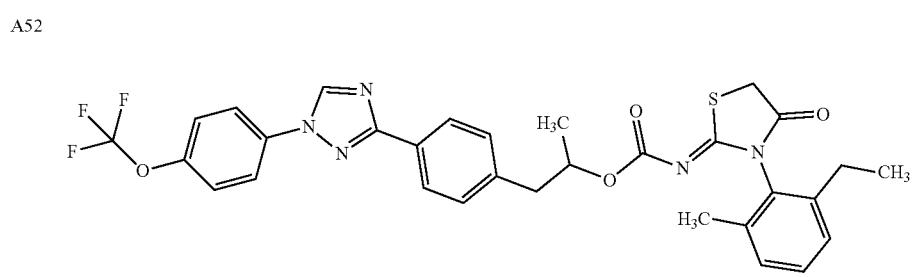
A53 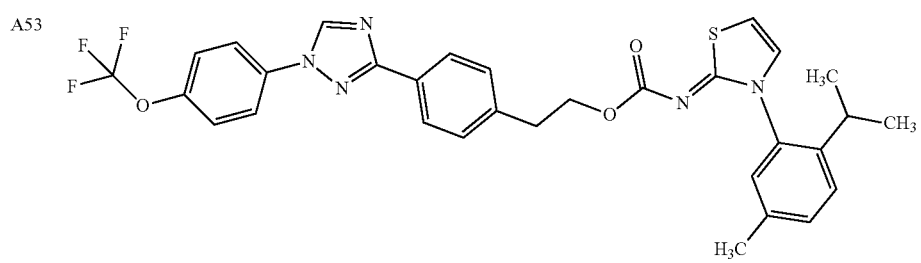
A54 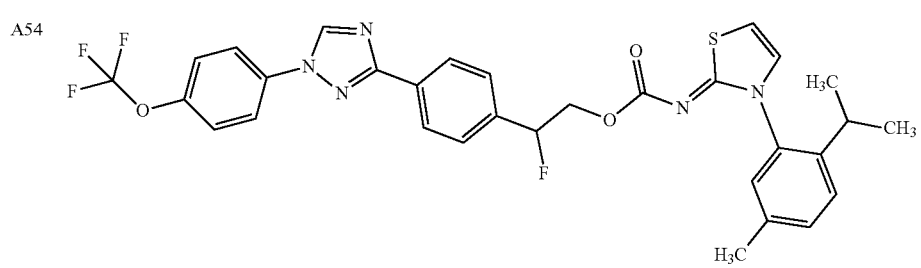

TABLE 1-continued

Structures for Compounds

A55

Preparation of Triaryl Alcohols

Alcohol analogs can be prepared as shown in Scheme 1 below. A triaryl aldehyde 1-1, wherein Het, Ar$^1$, and Ar$^2$ are as disclosed above, may be treated under Wittig olefination conditions such as methyltriphenylphosphonium bromide in the presence of a base such as 1,8-diazabicyclo[5.4.0]undec-7-ene (DBU) and in a polar, aprotic solvent such as tetrahydrofuran (THF) at the reflux temperature to provide the alkene 1-2, wherein Het, Ar$^1$, and Ar$^2$ are as disclosed above (Scheme 1, step a). The alkene 1-2, wherein Het, Ar$^1$, and Ar$^2$ are as disclosed above, can be reacted under hydroboration-oxidation conditions to afford the corresponding alcohol 1-3a, wherein Het, Ar$^1$, and Ar$^2$ are as disclosed above, by reaction with 9-borabicyclo[3.3.1]nonane (9-BBN) and 30% hydrogen peroxide in a polar, aprotic solvent such as THF and aqueous sodium hydroxide at ambient temperature (Scheme 1, step b). The triaryl alkene 1-2, wherein Het, Ar$^1$, and Ar$^2$ are as disclosed above, can be treated with meta-chloroperoxybenzoic acid (m-CPBA) in an aprotic solvent, such as dichloromethane at ambient temperature to provide the triaryl epoxide 1-4, wherein Het, Ar$^1$, and Ar$^2$ are as disclosed above (Scheme 1, step c). Opening of the epoxide and further functionalization can be achieved by reaction of the triaryl epoxide 1-4, wherein Het, Ar$^1$, and Ar$^2$ are as disclosed above, with either pyridine hydrofluoride at a temperature from 0° C. to ambient temperature to afford 1-3b, or trichloroisocyanuric acid in the presence of triphenylphosphine and in a polar, aprotic solvent such as acetonitrile at ambient temperature to provide 1-3c, wherein Het, Ar$^1$, and Ar$^2$ are as disclosed above (Scheme 1, steps d and e).

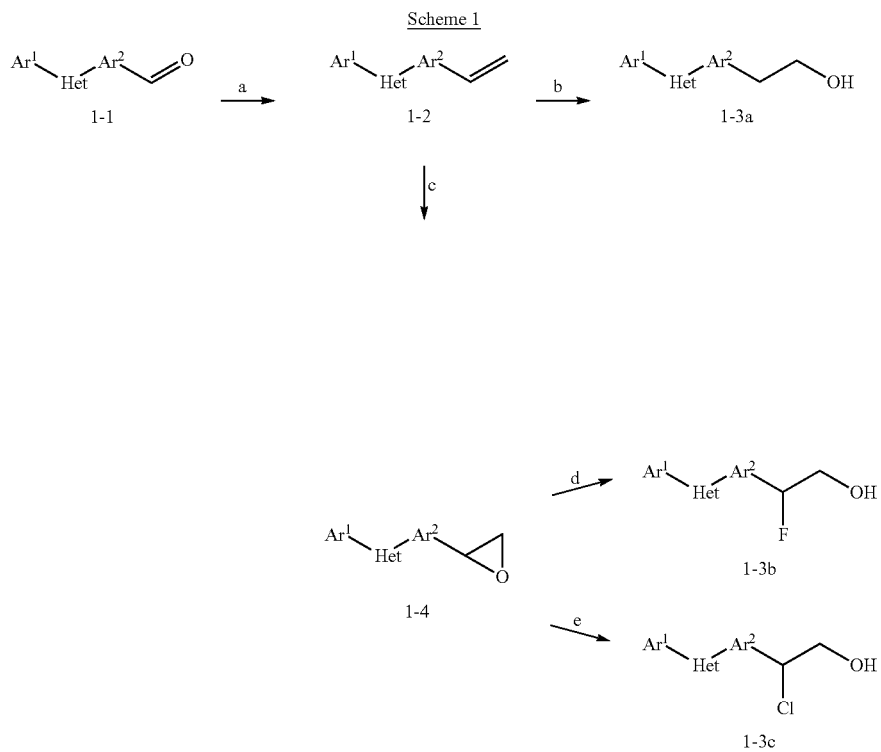

Scheme 1

Alcohol analogs can be prepared as shown in Scheme 2 below. A triaryl bromide 2-1, wherein Het, Ar¹, and Ar² are as disclosed above, may be treated with pentane-2,4-dione in the presence of a catalyst such as copper(I) iodide and a base such as potassium phosphate in a polar, aprotic solvent such as dimethyl sulfoxide (DMSO) at the temperature of about 90° C. to provide the ketone 2-2, wherein Het, Ar¹, and Ar² are as disclosed above (Scheme 2, step a). The ketone 2-2, wherein Het, Ar¹, and Ar² are as disclosed above, can be reduced to the corresponding alcohol 2-3, wherein Het, Ar¹, and Ar² are as disclosed above, by reaction with sodium borohydride in a polar, protic solvent such as ethanol at ambient temperature (Scheme 2, step b). The triaryl bromide 2-1, wherein Het, Ar¹, and Ar² are as disclosed above, may be transformed into the corresponding triaryl iodide 2-4, wherein Het, Ar¹, and Ar² are as disclosed above, using sodium iodide in the presence of a catalyst such as copper(I) iodide and a base such as (1R,2R)—$N_1,N_2$-dimethylcyclohexane-1,2-diamine in a polar, aprotic solvent such as dioxane at the temperature of about 100° C. (Scheme 2, step c). The triaryl amide 2-5 can be prepared in two steps. Reaction of a triaryl iodide 2-4, wherein Het, Ar¹, and Ar² are as disclosed above, with copper and ethyl 2-bromo-2,2-difluoroacetate in the presence of a polar, aprotic solvent such as DMSO at a temperature of about 60° C. to give the difluoroacetate ethyl ester (not shown, Scheme 2, step d). Reaction of the ester with a solution of ammonia in methanol in a polar, protic solvent such as methanol at ambient temperature affords the amide 2-5, wherein Het, Ar¹, and Ar² are as disclosed above (Scheme 3, step e). Reduction of the triaryl amide 2-5, wherein Het, Ar¹, and Ar² are as disclosed above, can be accomplished by reaction with a reducing agent such as borane-THF complex in a polar, aprotic solvent such as THF at a temperature of about 60° C. to afford the alcohol 2-6, wherein Het, Ar¹, and Ar² are as disclosed above (Scheme 2, step f).

disclosed, in a mixed solvent system, such as dichloromethane-water, and in the presence of a base, such as sodium bicarbonate (Scheme 3, step b) to afford the carbamate Scheme 3

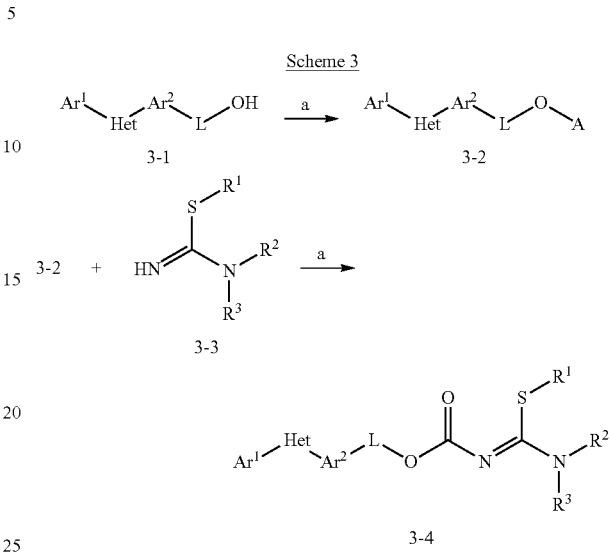

Acid and Salt Derivatives and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

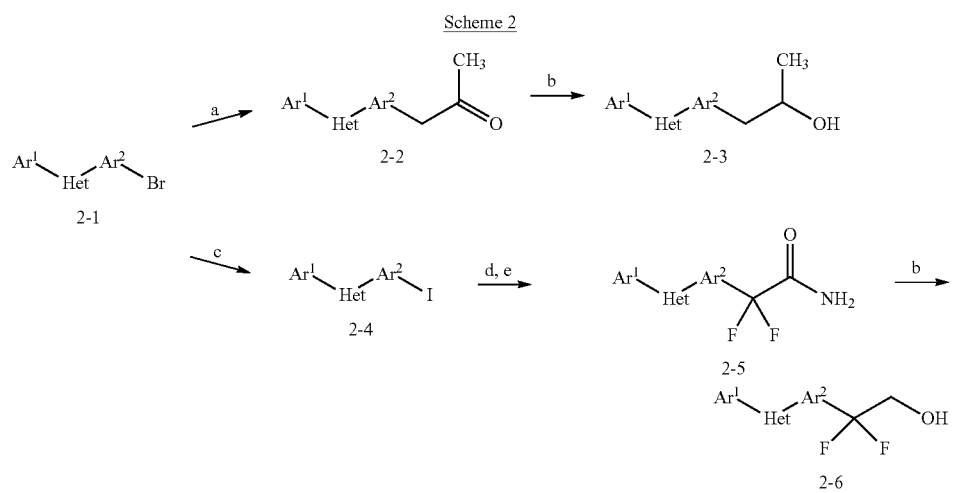

Preparation of Carbamate Analogs

The activated triaryl alcohol 3-2, wherein Het, Ar¹, Ar², and L are as previously disclosed, can be generated by treatment of the triaryl alcohol 3-1 (Scheme 3) with an activating agent such as bis(2,5-dioxopyrrolidin-1-yl) carbonate in a polar, aprotic solvent, such as acetonitrile, and in the presence of a base, such as pyridine, (Scheme 3, step a). The activated intermediate is then allowed to react with a thiourea 3-3, wherein R³, R¹, and R² are as previously Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous sodium hydroxide (NaOH), potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well-known herbicide.

The compounds disclosed in this invention can also form stable complexes with solvent molecules that remain intact after the non-complexed solvent molecules are removed from the compounds. These complexes are often referred to as "solvates."

Stereoisomers

Certain compounds disclosed in this document can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass *Ataenius*), *Atomaria linearis* (pygmy mangold beetle), *Aulacophora* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata*, *Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris*, *Conoderus stigmosus*, *Conotrachelus nenuphar* (plum *curculio*), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae*, *Hylobius* pales (pales weevil), *Hypera* spp. (weevils), *Hypera postica* (alfalfa weevil), *Hyperdoes* spp. (*Hyperodes* weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus*, *Liogenys suturalis*, *Lissorhoptrus oryzophilus* (rice water weevil), *Lyctus* spp. (wood beetles/powder post beetles), *Maecolaspis joliveti*, *Megascelis* spp., *Melanotus communis*, *Meligethes* spp., *Meligethes aeneus* (blossom beetle), *Melolontha melolontha* (common European cockchafer), *Oberea brevis*, *Oberea linearis*, *Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae*, *Pantomorus* spp. (weevils), *Phyllophaga* spp. (May/June beetle), *Phyllophaga cuyabana*, *Phyllotreta* spp. (chrysomelids), *Phynchites* spp., *Popillia japonica* (Japanese beetle), *Prostephanus* truncates (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica*, *Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochlomyia* spp. (screwworms), *Contarinia* spp. (gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis*

(little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (housefly), *Oestrus ovis* (sheep bot fly), *Oscinellafrit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea,* and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pineapple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabubfera* (jute looper), *Anticarsia gemmatalis* (velvetbean caterpillar), *Archips argyrospila* (fruit tree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leaf perforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydiafunebrana* (plum fruit moth), *Cydia molesta* (oriental fruit moth), *Cydia nignicana*

(pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwestern corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen louse).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria, Melanoplus* spp. (grasshoppers), *Microcentrum retinerve* (angular winged katydid), *Pterophylla* spp. (katydids), *chistocerca gregaria, Scudderia furcata* (fork tailed bush katydid), and *Valanga nigricorni*.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (*thrips*). A non-exhaustive list of these pests includes, but is not limited to, *Frankliniella fusca* (tobacco *thrips*), *Frankliniella occidentalis* (western flower *thrips*), *Frankliniella shultzei Frankliniella williamsi* (corn *thrips*), *Heliothrips haemorrhaidalis* (greenhouse *thrips*), *Riphiphorothrips cruentatus, Scirtothrips* spp., *Scirtothrips citri* (citrus *thrips*), *Scirtothrips dorsalis* (yellow tea *thrips*), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (American dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (two-spotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp.

(lesion nematodes), *Radopholus* spp. (burrowing nematodes), and *Rotylenchus renformis* (kidney-shaped nematode).

In another embodiment, the invention disclosed in this document can be used to control Symphyla (symphylans). A non-exhaustive list of these pests includes, but is not limited to, *Scutigerella immaculata*.

Neonicotinoid-resistant insects are known in the art (see for example WO 2012/141754 A2). Compounds of the subject invention disclosed herein have the advantage of being superior or at least equal in insecticidal activity against such neonicotinoid-resistant insects as compared to previously disclosed compounds. In some embodiments, the neonicotinoid-resistant insect has resistance to at least one of the insecticides selected from the group consisting of acetamiprid, clothianidin, dinotefuran, flupyradifurone (BYI 02960), imidacloprid, imidaclothiz, nitenpyram, thiacloprid, thiamethoxam, and combinations thereof. In other embodiments, the combination between the compounds of the subject invention and a second pesticide can be used for controlling such neonicotinoid-resistant insects. In further embodiments, the second pesticide is selected from the group consisting of acetamiprid, clothianidin, dinotefuran, flupyradifurone (BYI 02960), imidacloprid, imidaclothiz, nitenpyram, thiacloprid, and thiamethoxam.

Mixtures

The invention disclosed in this document can also be used with various insecticides, both for reasons of economy and synergy. Such insecticides include, but are not limited to, antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, fumigant insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

Some of the particular insecticides that can be employed beneficially in combination with the invention disclosed in this document include, but are not limited to, the following 1,2-dichloropropane, 1,3-dichloropropene, abamectin, acephate, acetamiprid, acethion, acetoprole, acrinathrin, acrylonitrile, acynonapyr, afidopyropen, afoxolaner, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azotoate, barium hexafluorosilicate, barthrin, bendiocarb, benfuracarb, bensultap, benzpyrimoxan, beta-cyfluthrin, beta-cypermethrin, bifenthrin, bioallethrin, bioethanomethrin, biopermethrin, bioresmethrin, bistrifluron, borax, boric acid, broflanilide, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chloroprallethrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cycloprothrin, cycloxaprid, cyfluthrin, cyhalothrin, cyhalodiamide, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dimpropyridaz, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, epsilon-metofluthrin, epsilon-momfluorothrin, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, flufiprole, fluhexafon, flupyradifurone, flupyrimin, fluralaner, fluvalinate, fluxametamide, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imidaclothiz, imiprothrin, indoxacarb, iodomethane, IPSP, isazofos, isobenzan, isocarbophos, isocycloseram, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lotilaner, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methylchloroform, methylene chloride, metofluthrin, metolcarb, metoxadiazone, mevinphos, mexacarbate, milbemectin, milbemycin oxime, mipafox, mirex, momfluorothrin, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxazosulfyl, oxydemeton-methyl, oxydeprofos, oxydisulfoton, paichongding, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sarolaner, sophamide, spinetoram, spinosad, spiromesifen, spiropidion, spirotetramat, sulcofuron, sulfoxaflor, sulfluramid, sulfotep, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, tetraniliprole, tetrachlorantraniliprole, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, tyclopyrazoflor, vamidothion, vaniliprole, XMC, xylylcarb, zeta-cypermethrin, zolaprofos, and α-ecdysone.

Additionally, any combination of the above insecticides can be used.

The invention disclosed in this document can also be used, for reasons of economy and synergy, with acaricides, algicides, antifeedants, avicides, bactericides, bird repellents, chemosterilants, fungicides, herbicide safeners, herbicides, insect attractants, insect repellents, mammal repellents, mating disrupters, molluscicides, plant activators, plant growth regulators, rodenticides, synergists, defoliants, desiccants, disinfectants, semiochemicals, and virucides (these categories not necessarily mutually exclusive).

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetylcholinesterase inhibitor; sodium channel modulator; chitin biosynthesis inhibitor; GABA-gated chloride channel antagonist; GABA- and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, and ryanodine receptor (RyRs).

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one nonionic lipophilic surface-active agent, (2) at least one nonionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, nonionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Nonionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are nonionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often nonionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV (ultra low volume) formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

Applications

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by any pest, for example, vegetable crops, fruit and nut trees, grapevines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur. Generally, pest populations, activity, or both are desirably reduced more than fifty percent, preferably more than 90 percent.

Generally, with baits, the baits are placed in the ground where, for example, termites can come into contact with the bait. Baits can also be applied to a surface of a building, (horizontal, vertical, or slant surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping. Compounds are applied in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

Combinations

In another embodiment of this invention, molecules of Formula A, Formula One, Formula Two or Formula Three may be used in combination (such as, in a compositional mixture, or a simultaneous or sequential application) with one or more active ingredients.

In another embodiment of this invention, molecules of Formula A, Formula One, Formula Two or Formula Three may be used in combination (such as, in a compositional mixture, or a simultaneous or sequential application) with one or more active ingredients each having a mode of action (MoA) that is the same as, similar to, but more likely— different from, the MoA of the molecules of Formula A, Formula One, Formula Two or Formula Three.

In another embodiment, molecules of Formula A, Formula One, Formula Two or Formula Three may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula A, Formula One, Formula Two or Formula Three may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula A, Formula One, Formula Two or Formula Three may also be used in combination (such as in a compositional mixture, or a simultaneous or sequential application) with one or more biopesticides.

In another embodiment, in a pesticidal composition combinations of a molecule of Formula A, Formula One, Formula Two or Formula Three and an active ingredient may be used in a wide variety of weight ratios. For example, in a two-component mixture, the weight ratio of a molecule of Formula A, Formula One, Formula Two or Formula Three to an active ingredient, the weight ratios in Table A may be used. However, in general, weight ratios less than about 10:1 to about 1:10 are preferred. It is also preferred sometimes to use a three, four, five, six, seven, or more, component mixture comprising a molecule of Formula A, Formula One, Formula Two or Formula Three and an additional two or more active ingredients.

TABLE A

Weight Ratios
Molecule of the Formula A, Formula One,
Formula Two or Formula Three:
active ingredient 100:1 to 1:100
50:1 to 1:50
20:1 to 1:20
10:1 to 1:10
5:1 to 1:5
3:1 to 1:3
2:1 to 1:2
1:1

Weight ratios of a molecule of Formula A, Formula One, Formula Two or Formula Three to an active ingredient may also be depicted as X:Y; wherein X is the parts by weight of a molecule of Formula A, Formula One, Formula Two or Formula Three and Y is the parts by weight of active ingredient. The numerical range of the parts by weight for X is $0 < X \leq 100$ and the parts by weight for Y is $0 < Y \leq 100$ and is shown graphically in Table B. By way of non-limiting example, the weight ratio of a molecule of Formula A, Formula One, Formula Two or Formula Three to an active ingredient may be 20:1.

Ranges of weight ratios of a molecule of Formula A, Formula One, Formula Two or Formula Three to an active ingredient may be depicted as $X_1:Y_1$ to $X_2:Y_2$, wherein X and Y are defined as above.

TABLE B

| active ingredient (Y) Parts by weight | 1 | 2 | 3 | 5 | 10 | 15 | 20 | 50 | 100 |
|---|---|---|---|---|---|---|---|---|---|
| 100 | X, Y |  | X, Y |  |  | X, Y |  |  |  |
| 50 | X, Y | X, Y | X, Y |  |  | X, Y | X, Y |  |  |
| 20 | X, Y |  | X, Y | X, Y |  | X, Y |  | X, Y |  |
| 15 | X, Y | X, Y |  |  |  |  | X, Y | X, Y | X, Y |
| 10 | X, Y |  | X, Y |  |  |  |  |  |  |
| 5 | X, Y | X, Y | X, Y |  |  |  | X, Y |  |  |
| 3 | X, Y | X, Y |  | X, Y | X, Y |  | X, Y | X, Y | X, Y |
| 2 | X, Y |  | X, Y | X, Y |  | X, Y |  | X, Y |  |
| 1 | X, Y | X, Y | X, Y | X, Y | X, Y | X, Y | X, Y | X, Y | X, Y | molecule of Formula A, Formula One, Formula Two or Formula Three (X) Parts by weight In one embodiment, the range of weight ratios may be $X_1:Y_1$ to $X_2:Y_2$, wherein $X_1 > Y_1$ and $X_2 < Y_2$. By way of non-limiting example, the range of a weight ratio of a molecule of Formula A, Formula One, Formula Two or Formula Three to an active ingredient may be between 3:1 and 1:3, inclusive of the endpoints.

In another embodiment, the range of weight ratios may be $X_1:Y_1$ to $X_2:Y_2$, wherein $X_1 > Y_1$ and $X_2 > Y_2$. By way of non-limiting example, the range of weight ratio of a molecule of Formula A, Formula One, Formula Two or Formula Three to an active ingredient may be between 15:1 and 3:1, inclusive of the endpoints.

In another embodiment, the range of weight ratios may be $X_1:Y_1$ to $X_2:Y_2$, wherein $X_1 < Y_1$ and $X_2 < Y_2$. By way of non-limiting example, the range of weight ratios of a molecule of Formula A, Formula One, Formula Two or Formula Three to an active ingredient may be between about 1:3 and about 1:20, inclusive of the endpoints.

It is envisioned that certain weight ratios of a molecule of Formula A, Formula One, Formula Two or Formula Three to an active ingredient, as presented in Table A and B, may be synergistic.

EXAMPLES

The examples are for illustration purposes and are not to be construed as limiting the invention disclosed in this document to only the embodiments disclosed in these examples.

Starting materials, reagents and solvents which are obtained from commercial sources are used without further purification. Anhydrous solvents are purchased as Sure/Seal™ from Aldrich and are used as received. Melting points are obtained on a Thomas Hoover Unimelt capillary melting point apparatus or an OptiMelt Automated Melting Point System from Sanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H nuclear magnetic resonance (NMR) spectral data are in parts per million (ppm, δ) and were recorded at 300, 400, or 500; $^{13}$C NMR spectral data are in ppm (δ) and were recorded at 75, 100, or 150 MHz, and $^{19}$F NMR spectral data are in ppm (δ) and were recorded at 376 MHz, unless otherwise stated.

Example 1: Preparation of 1-(4-(perfluoroethoxy) phenyl)-3-(4-vinylphenyl)-1H-1,2,4-triazole (C1)

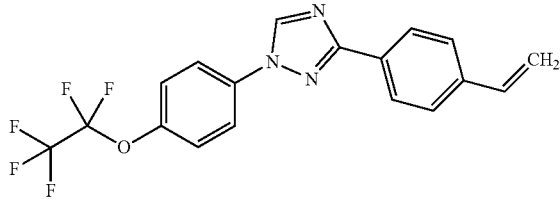 [SMILES: C=Cc1ccc(-c2ncn(-c3ccc(OC(F)(F)C(F)(F)F)cc3)n2)cc1]

The title compound was prepared as in Fischer, L. G. et al., U. S. Patent Application Publication 2014/0274688 from 4-(1-(4-(perfluoroethoxy)phenyl)-1H-1,2,4-triazol-3-yl) benzaldehyde (prepared as in Crouse, G. et al., PCT International Application WO 2009/102736 A1, 1.5 g, 3.9 mmol) and isolated as a white solid (895 mg, 59%): mp 141-143° C.; $^1$H NMR (400 MHz, CDCl$_3$) δ 8.57 (s, 1H), 8.19-8.13 (m, 2H), 7.86-7.77 (m, 2H), 7.58-7.46 (m, 2H), 7.44-7.35 (m, 2H), 6.78 (dd, J=17.6, 10.9 Hz, 1H), 5.84 (dd, J=17.6, 0.8 Hz, 1H), 5.32 (dd, J=10.8, 0.8 Hz, 1H); $^{19}$F NMR (376 MHz, CDCl$_3$) δ −85.90, −87.84; ESIMS m z 382 ([M+H]$^+$).

Example 2: Preparation of 2-(4-(1-(4-(perfluoroethoxy)phenyl)-1H-1,2,4-triazol-3-yl)phenyl)ethan-1-ol (C2)

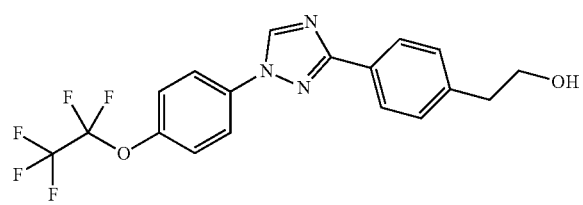 [SMILES: OCCc1ccc(-c2ncn(-c3ccc(OC(F)(F)C(F)(F)F)cc3)n2)cc1]

To 1-(4-(perfluoroethoxy)phenyl)-3-(4-vinylphenyl)-1H-1,2,4-triazole (C1; 896 milligrams (mg), 2.35 mmol) was dissolved in THF (15 milliliters (mL)). 9-Borabicyclo[3.3.1] nonane (9-BBN; 9.4 mL, 4.7 mmol) was added, and the reaction mixture was stirred at room temperature for 5 hours (h). 2 Normal (N) Sodium hydroxide (NaOH; 2.35 mL, 4.7 mmol) and 30% hydrogen peroxide (0.6 mL, 5.9 mmol) were added sequentially. A slight exotherm was observed. The bright yellow solution was stirred at room temperature and turned pale over 2 h. After 2 h, the mixture was diluted with water and extracted with ethyl acetate. The organic extracts were dried over sodium sulfate, filtered, and concentrated to give a clear oil. The oil was loaded onto a Celite® cartridge with dichloromethane (DCM). Purification by flash chromatography (0-100% ethyl acetate/ hexanes) provided the title compound as a white solid (223 mg, 23%): mp 91-96° C.; $^1$H NMR (400 MHz, CDCl$_3$) δ 8.57 (s, 1H), 8.16-8.11 (m, 2H), 7.83-7.78 (m, 2H), 7.40 (d, J=8.8 Hz, 2H), 7.36 (d, J=8.2 Hz, 2H), 3.92 (q, J=6.4 Hz, 2H), 2.95 (t, J=6.5 Hz, 2H), 1.40 (t, J=5.9 Hz, 1H); $^{19}$F NMR (376 MHz, CDCl$_3$) δ −85.90, −87.84; ESIMS m z 400 ([M+H]$^+$).

Example 3: Preparation of (E)-N-((dimethylamino) methylene)-4-methoxybenzamide (C3)

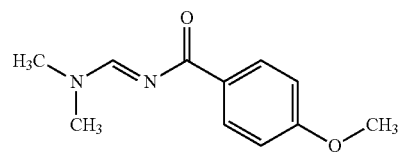

4-Methoxybenzamide (10 g, 66 mmol) in N,N-dimethylformamide dimethyl acetal (DMF-DMA; 35 mL) was heated at 90° C. for 2 h. The reaction mixture was cooled, diluted with diethyl ether and ethyl acetate, and washed twice with water. The organic layer was dried over sodium sulfate, filtered, and concentrated. The title compound was isolated as a white solid (11.9 g, 86%): mp 92-93° C.; $^1$H NMR (400 MHz, DMSO-d$_6$) δ 8.56 (s, 1H), 8.13-8.07 (m, 2H), 7.00-6.92 (m, 2H), 3.81 (s, 3H), 3.18 (s, 3H), 3.12 (s, 3H); $^{13}$C NMR (101 MHz, DMSO-d$_6$) δ 175.23, 162.07, 160.40, 131.20, 129.43, 113.18, 55.25, 40.76, 34.82.

Example 4: Preparation of 3-(4-methoxyphenyl)-1H-1,2,4-triazole (C4)

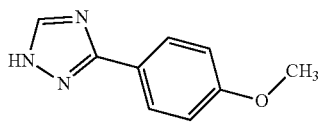

To (E)-N-((dimethylamino)methylene)-4-methoxybenzamide (C3; 11.9 g, 57.5 mmol) in acetic acid (75 mL) was added hydrazine monohydrate (2.7 mL, 87 mmol). The reaction mixture was heated at 100° C. for 1.5 h. The reaction mixture was cooled, diluted with water, and allowed to sit at room temperature for 3 days. The white precipitate was filtered and dried. The title compound was isolated as a white solid (7.50 g, 74%): mp 188-189.5° C.; $^1$H NMR (400 MHz, DMSO-d$_6$) δ 14.09 (s, 1H), 8.35 (s, 1H), 8.12-7.79 (m, 2H), 7.05 (d, J=8.6 Hz, 2H), 3.81 (s, 3H); EIMS m z 175.

Example 5: Preparation of 3-(4-methoxyphenyl)-1-(4-(trifluoromethoxy)phenyl)-1H-1,2,4-triazole (C5)

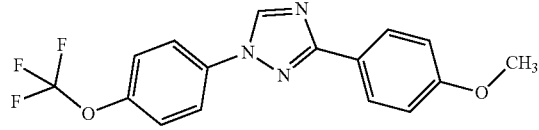 [SMILES: COc1ccc(-c2ncn(-c3ccc(OC(F)(F)F)cc3)n2)cc1]

3-(4-Methoxyphenyl)-1H-1,2,4-triazole (C4; 4.47 g, 256 mmol), 1-iodo-4-(trifluoromethoxy)benzene (10.3 g, 36 mmol), cesium carbonate (22.4 g, 69 mmol), copper(I) iodide (1.98 g, 10.4 mmol), and 8-hydroxyquinoline (1.49 g, 10.3 mmol) in N,N-dimethylformamide (DMF; 160 mL) and water (16 mL) was heated at 150° C. for 6 h. The reaction mixture was cooled to room temperature overnight. The reaction was quenched with water and ammonium hydroxide, and the mixture was extracted with diethyl ether. The emulsion was filtered to remove copper solids, and the mixture was extracted once more with diethyl ether. The combined organic extracts were washed with water, dried over sodium sulfate, filtered, and concentrated. Purification of the resulting concentrate by flash chromatography (0-50% ethyl acetate/hexanes) provided the title compound as a white solid (4.58 g, 53%): mp 99.5-100.5° C.; $^1$H NMR (400 MHz, CDCl$_3$) δ 8.53 (s, 1H), 8.18-8.07 (m, 2H), 7.84-7.73 (m, 2H), 7.38 (dd, J=9.0, 0.7 Hz, 2H), 7.08-6.96 (m, 2H), 3.88 (s, 3H); $^{19}$F NMR (376 MHz, CDCl$_3$) δ −58.04; EIMS m z 335.

Example 6: Preparation of 4-(1-(4-(trifluoromethoxy)phenyl)-1H-1,2,4-triazol-3-yl)phenol (C6)

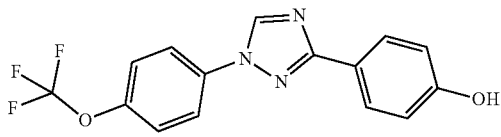 [SMILES: Oc1ccc(-c2ncn(-c3ccc(OC(F)(F)F)cc3)n2)cc1]

To 3-(4-methoxyphenyl)-1-(4-(trifluoromethoxy)phenyl)-1H-1,2,4-triazole (C5; 4.57 g, 13.6 mmol) in DCM (45 mL) at 0° C. was added boron tribromide (1 molar (M) solution in DCM; 41 mL, 41 mmol) in portions over 15 minutes (min). The reaction mixture was stirred at 0° C. for 2.5 h. The reaction mixture was diluted with DCM and water, cooled in an ice bath, and brought to pH 7 by the slow addition of a saturated aqueous sodium bicarbonate solution. The organic layer was separated, and the aqueous layer was extracted twice with ethyl acetate. The combined organic layers were dried over sodium sulfate, filtered, and concentrated. The resultant material was adsorbed onto silica gel. Purification by flash chromatography (0-100% ethyl acetate/hexanes) provided the title compound as a white solid (3.99 g, 91%): mp 182-184° C.; $^1$H NMR (400 MHz, DMSO-d$_6$) δ 9.84 (s, 1H), 9.32 (s, 1H), 8.09-7.98 (m, 2H), 7.98-7.87 (m, 2H), 7.61 (d, J=8.3 Hz, 2H), 6.94-6.83 (m, 2H); $^{19}$F NMR (376 MHz, DMSO-d$_6$) δ −56.98; ESIMS m z 322 ([M+H]$^+$).

Example 7: Preparation of 1-(4-(1-(4-(trifluoromethoxy)phenyl)-1H-1,2,4-triazol-3-yl)phenyl)propan-2-one (C7)

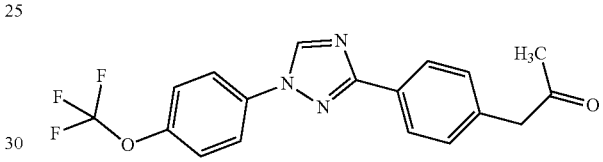

A solution of 3-(4-bromophenyl)-1-(4-(trifluoromethoxy)phenyl)-1H-1,2,4-triazole (prepared as in Fischer, L. G. et al., U. S. Patent Application Publication 2014/0274688; 12.3 g, 32.0 mmol), potassium phosphate (20.4 g, 96 mmol), water (0.692 g, 38.4 mmol), copper(I) iodide (0.61 g, 3.2 mmol), and pentane-2,4-dione (9.62 g, 96 mmol) in DMSO (100 mL) was degassed under nitrogen for 30 min. The reaction mixture was heated at 90° C. for 24 h. The reaction mixture was cooled, diluted with water (150 mL), and extracted with diethyl ether (2×150 mL). The combined organic layers were washed with water, dried over sodium sulfate, and concentrated. Purification by flash chromatography (0-70% ethyl acetate/hexanes) provided the title compound as an off-white solid (7.15 g, 60%): mp 91-95° C.; H NMR (400 MHz, CDCl$_3$) δ 8.58 (s, 1H), 8.17 (d, J=7.9 Hz, 2H), 7.84-7.75 (m, 2H), 7.44-7.37 (m, 2H), 7.33 (d, J=7.8 Hz, 2H), 3.77 (s, 2H), 2.19 (s, 3H); ESIMS m z 362 ([M+H]$^+$).

Example 8: Preparation of 1-(4-(1-(4-(trifluoromethoxy)phenyl)-1H-1,2,4-triazol-3-yl)phenyl)propan-2-ol (C8)

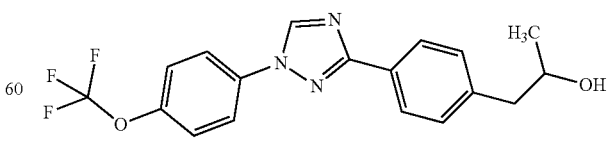

To 1-(4-(1-(4-(trifluoromethoxy)phenyl)-1H-1,2,4-triazol-3-yl)phenyl)propan-2-one (C7; 3.74 g, 10.4 mmol) in ethanol (150 mL) was added sodium borohydride (0.78 g, 20.7 mmol). The reaction mixture was stirred at room temperature for 2 h. The solution was poured onto water and extracted with ethyl acetate. The organic layers were dried over sodium sulfate and concentrated. The title compound was isolated as a beige solid (3.55 g, 93%): mp 72-80° C.; ¹H NMR (400 MHz, CDCl₃) δ 8.56 (s, 1H), 8.18-8.09 (m, 2H), 7.86-7.75 (m, 2H), 7.39 (dt, J=8.0, 1.0 Hz, 2H), 7.34 (d, J=8.2 Hz, 2H), 4.10 (dd, J=14.0, 7.0 Hz, 1H), 2.94-2.65 (m, 2H), 1.54 (s, 1H), 1.28 (d, J=6.2 Hz, 3H); ¹³C NMR (101 MHz, CDCl₃) δ 163.89, 153.06, 141.95, 140.78, 136.05, 130.24, 129.14, 127.25, 126.77, 122.87, 121.66, 69.31, 46.14, 23.36; ESIMS m z 364 ([M+H]⁺).

Example 9: Preparation of 3-(4-(oxiran-2-yl)phenyl)-1-(4-(trifluoromethoxy)phenyl)-1H-1,2,4-triazole (C9)

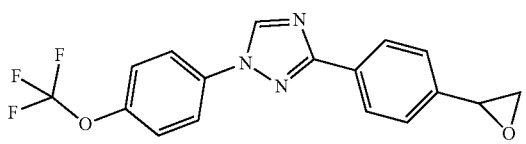 [SMILES: FC(F)(F)Oc1ccc(-n2cnc(-c3ccc(C4CO4)cc3)n2)cc1]

To a solution of 1-(4-(trifluoromethoxy)phenyl)-3-(4-vinylphenyl)-1H-1,2,4-triazole (prepared as in Fischer, L. G. et al., U. S. Patent Application Publication 2014/0274688; 10 g, 30.2 mmol) in DCM (60 mL) was added meta-chloroperoxybenzoic acid (m-CPBA; 11.8 g, 45.3 mmol) portion wise at 0° C., and the reaction mixture was warmed to room temperature for 4 h. The reaction mixture was quenched with saturated aqueous sodium bicarbonate and extracted with ethyl acetate (3×150 mL). The organic layer was washed with water and brine, dried over anhydrous sodium sulfate, filtered, and concentrated under reduced pressure. Purification by column chromatography (15-20% ethyl acetate/petroleum ether) provided the title compound as a pale yellow solid (7 g, 70%): ¹H NMR (300 MHz, CDCl₃) δ 8.60 (s, 1H), 8.18 (d, J=7.8 Hz, 2H), 7.80 (d, J=9.0 Hz, 2H), 7.44-7.36 (m, 4H), 3.93-3.91 (m, 1H), 3.22-3.17 (m, 1H), 2.87-2.84 (m, 1H); ESIMS m z 348 ([M+H]⁺).

The following compound was prepared according to the procedure in Example 9.

3-(4-(Oxiran-2-yl)phenyl)-1-(4-(perfluoroethoxy)phenyl)-1H-1,2,4-triazole (C10)

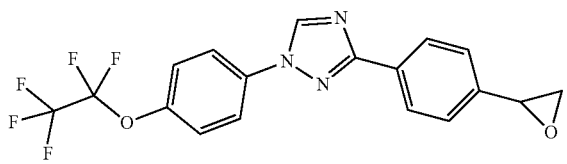 [SMILES: FC(F)(F)C(F)(F)Oc1ccc(-n2cnc(-c3ccc(C4CO4)cc3)n2)cc1]

The title compound was prepared from intermediate C1 and was isolated as an off-white solid (5 g, 80%): ¹H NMR (400 MHz, CDCl₃) δ 8.57 (s, 1H), 8.18 (d, J=8.4 Hz, 2H), 7.82-7.79 (m, 2H), 7.44-7.38 (m, 4H), 3.96-3.91 (m, 1H), 3.21-3.18 (m, 1H), 2.88-2.84 (m, 1H); ESIMS m z 398 ([M+H]⁺).

Example 10: Preparation of 2-fluoro-2-(4-(1-(4-(trifluoromethoxy)phenyl)-1H-1,2,4-triazol-3-yl)phenyl)ethan-1-ol (C11)

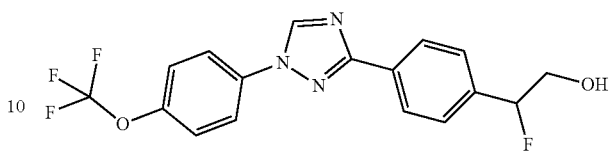

To a solution of 3-(4-(oxiran-2-yl)phenyl)-1-(4-(trifluoromethoxy)phenyl)-1H-1,2,4-triazole (C9, 7 g, 20.2 mmol) in DCM (50 mL) was added pyridine hydrofluoride (HF-pyridine; 9 mL, 30.3 mmol) dropwise at 0° C., and the reaction mixture was stirred at room temperature for 4 h. The reaction mixture was quenched with water and extracted with ethyl acetate (3×50 mL). The organic layer was washed with water and brine, dried over anhydrous sodium sulfate, filtered, and concentrated under reduced pressure. Purification by column chromatography (15-20% ethyl acetate/petroleum ether) provided the title compound as an off-white solid (5 g, 64%): mp 126-128° C. ¹H NMR (400 MHz, DMSO-d₆) δ 9.40 (s, 1H), 8.13 (d, J=8.4 Hz, 2H), 8.10-8.05 (m, 2H), 7.62 (d, J=8.0 Hz, 2H), 7.53 (d, J=8.4 Hz, 2H), 5.66-5.51 (m, 1H), 5.20 (t, J=6.0 Hz, 1H), 3.79-3.29 (m, 2H); ¹⁹F NMR (376 MHz, DMSO-d₆) δ −56.98, −183.38; ESIMS m z 368 ([M+H]⁺).

The following compound was prepared according to the procedure in Example 10.

2-Fluoro-2-(4-(1-(4-(perfluoroethoxy)phenyl)-1H-1,2,4-triazol-3-yl)phenyl)ethan-1-ol (C12)

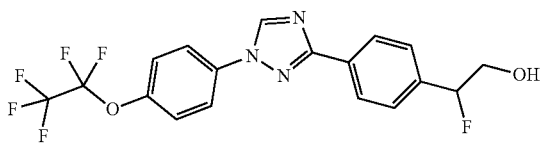 [SMILES: OCC(F)c1ccc(-c2ncn(-c3ccc(OC(F)(F)C(F)(F)F)cc3)n2)cc1]

The title compound was prepared from intermediate C10 and was isolated as an off-white solid (5 g, 49%): ¹H NMR (400 MHz, DMSO-d₆) δ 9.41 (s, 1H), 8.14-8.06 (m, 4H), 7.63 (d, J=9.2 Hz, 2H), 7.53 (d, J=8.4 Hz, 2H), 5.66-5.51 (m, 1H), 5.20 (t, J=5.6 Hz, 1H), 3.79-3.29 (m, 2H); ¹⁹F NMR (376 MHz, DMSO-d₆) δ −85.20, −86.89, −183.38; ESIMS m z 418 ([M+H]⁺).

Example 11: Preparation of 2-chloro-2-(4-(1-(4-(trifluoromethoxy)phenyl)-1H-1,2,4-triazol-3-yl)phenyl)ethan-1-ol (C13)

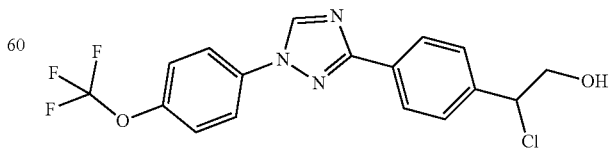

A solution of 3-(4-(oxiran-2-yl)phenyl)-1-(4-(trifluoromethoxy)phenyl)-1H-1,2,4-triazole (C9; 175 mg, 0.50 mmol), trichloroisocyanuric acid (59 mg, 0.25 mmol), and triphenylphosphine (198 mg, 0.76 mmol) in acetonitrile (4.9 mL) and water (0.1 mL) was stirred at room temperature for 3 h. The reaction mixture was concentrated under a stream of nitrogen overnight. The yellow oil was loaded onto a Celite® cartridge with DCM. Purification by flash chromatography (0-100% ethyl acetate/hexanes) provided the title compound as a white solid (114 mg, 58%): mp 135-137° C.; $^1$H NMR (400 MHz, CDCl$_3$) δ 8.57 (s, 1H), 8.24-8.18 (m, 2H), 7.84-7.76 (m, 2H), 7.55-7.51 (m, 2H), 7.43-7.36 (m, 2H), 5.06 (dd, J=7.2, 5.7 Hz, 1H), 3.99 (ddd, J=8.0, 5.9, 2.1 Hz, 2H), 2.12 (dd, J=7.8, 6.2 Hz, 1H); $^{19}$F NMR (376 MHz, CDCl$_3$) δ −58.03; ESIMS m z 384 ([M+H]$^+$).

Example 12: Preparation of 3-(4-iodophenyl)-1-(4-(trifluoromethoxy)phenyl)-1H-1,2,4-triazole (C14)

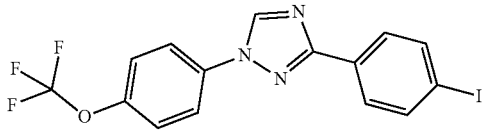 [SMILES: FC(F)(F)Oc1ccc(-n2cnc(-c3ccc(I)cc3)n2)cc1]

An oven-dried round bottomed flask was charged with 3-(4-bromophenyl)-1-(4-(trifluoromethoxy)phenyl)-1H-1,2,4-triazole (prepared as in Fischer, L. G. et al., U. S. Patent Application Publication 2014/0274688; 25.1 g, 65.2 mmol), (1R,2R)—N$_1$,N$_2$-dimethylcyclohexane-1,2-diamine (1.39 g, 9.8 mmol), sodium iodide (20.0 g, 134 mmol), copper(I) iodide (1.24 g, 6.52 mmol), and dioxane (100 mL). The reaction mixture was heated at 100° C. After 24 h, additional sodium iodide (5.0 g) and copper(I) iodide (0.60 g) were added and the reaction mixture was heated another 24 h at 100° C. After 24 h, additional (1R,2R)—N$_1$,N$_2$-dimethylcyclohexane-1,2-diamine (1.0 g), sodium iodide (5.5 g), and copper(I) iodide (1.0 g) were added. The reaction mixture was heated at 100° C. for 24 h. The reaction mixture was cooled, and the reaction quenched with saturated ammonium chloride and ammonium hydroxide. The mixture was stirred for 1 h. The biphasic mixture was extracted twice with ethyl acetate. The organic layers were dried over sodium sulfate, filtered, and concentrated. The resulting solid was adsorbed onto Celite®. Purification by reverse-phase flash chromatography (0-100% acetonitrile/water) provided the title compound as an off-white fluffy solid (28.0 g, 99%): mp 107-108° C.; $^1$H NMR (300 MHz, CDCl$_3$) δ 8.56 (s, 1H), 7.97-7.89 (m, 2H), 7.87-7.76 (m, 4H), 7.39 (dq, J=9.0, 1.0 Hz, 2H); $^{13}$C NMR (101 MHz, CDCl$_3$) δ 162.79, 148.51, 141.62, 137.87, 135.46, 129.88, 128.22, 122.42, 121.26, 119.10, 95.94; $^{19}$F NMR (376 MHz, CDCl$_3$) δ −58.03; HRMS-ESI (m z) [M+H]$^+$ calcd for C$_{15}$H$_9$F$_3$IN$_3$O, 430.9742; found, 430.9742.

Example 13: Preparation of Ethyl 2,2-difluoro-2-(4-(1-(4-(trifluoromethoxy)phenyl)-1H-1,2,4-triazol-3-yl)phenyl)acetate (C15)

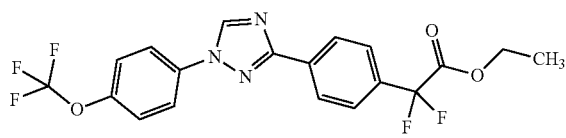 [SMILES: CCOC(=O)C(F)(F)c1ccc(-c2ncn(-c3ccc(OC(F)(F)F)cc3)n2)cc1]

A dry round-bottomed flask was charged with 3-(4-iodophenyl)-1-(4-(trifluoromethoxy)phenyl)-1H-1,2,4-triazole (C14; 2.60 g, 4.8 mmol), copper (0.92 g, 14.5 mmol), and dimethyl sulfoxide (DMSO; 8 mL). The flask was evacuated and backfilled with nitrogen. Ethyl 2-bromo-2,2-difluoroacetate (1.3 mL, 10.1 mmol) was added and the reaction mixture was heated at 60° C. for 24 h. The reaction mixture was cooled, and the reaction quenched with saturated ammonium chloride. The mixture was extracted with ethyl acetate. The organic layer was washed four times with water, dried over sodium sulfate, filtered, and concentrated. The brown oil was loaded onto a Celite® cartridge. Purification by flash chromatography (0-20% ethyl acetate/hexanes) provided the title compound as an off-white solid (1.72 g, 82%): mp 51.5-53.2° C.; $^1$H NMR (300 MHz, CDCl$_3$) δ 8.59 (s, 1H), 8.36-8.21 (m, 2H), 7.87-7.78 (m, 2H), 7.78-7.64 (m, 2H), 7.40 (dt, J=8.0, 0.9 Hz, 2H), 4.32 (q, J=7.2 Hz, 2H), 1.32 (t, J=7.1 Hz, 3H); $^{19}$F NMR (376 MHz, CDCl$_3$) δ −58.02, −104.09; ESIMS m z 428 ([M+H]$^+$); HRMS-ESI (m z) [M+H]+ calcd for C$_{19}$H$_{14}$F$_5$N$_3$O$_3$, 427.0955; found, 427.0964.

Example 14: Preparation of 2,2-difluoro-2-(4-(1-(4-(trifluoromethoxy)phenyl)-1H-1,2,4-triazol-3-yl)phenyl)acetamide (C16)

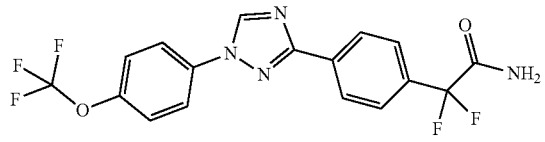 [SMILES: NC(=O)C(F)(F)c1ccc(-c2ncn(-c3ccc(OC(F)(F)F)cc3)n2)cc1]

To ethyl 2,2-difluoro-2-(4-(1-(4-(trifluoromethoxy)phenyl)-1H-1,2,4-triazol-3-yl)phenyl)acetate (C15; 0.81 g, 1.90 mmol) in methanol (19 ml) was added 2 M ammonia (7.6 mL, 15.2 mmol). The reaction mixture was stirred at room temperature for 30 min, then concentrated under a stream of nitrogen. The title compound was isolated as a white solid (770 mg, 100%): mp 218-226° C.; $^1$H NMR (300 MHz, DMSO-d$_6$) δ 9.46 (s, 1H), 8.43 (s, 1H), 8.25 (d, J=8.1 Hz, 2H), 8.12-8.06 (m, 3H), 7.74 (d, J=8.2 Hz, 2H), 7.64 (d, J=8.5 Hz, 2H); $^{13}$C NMR (126 MHz, DMSO-d$_6$) δ 165.78, 165.53, 165.29, 161.66, 147.74, 147.73, 144.62, 136.06, 135.05, 134.85, 134.64, 126.78, 126.40, 123.06, 121.80, 121.52, 119.48, 115.00; $^{19}$F NMR (471 MHz, DMSO-d$_6$) δ −56.95, −101.91; ESIMS m z 399 ([M+H]$^+$); HRMS-ESI (m z) [M+H]$^+$ calcd for C$_{17}$H$_{11}$F$_5$N$_4$O$_2$, 398.0802, found, 398.0806.

Example 15: Preparation of 2,2-difluoro-2-(4-(1-(4-(trifluoromethoxy)phenyl)-1H-1,2,4-triazol-3-yl)phenyl)ethan-1-ol (C17) and 2,2-difluoro-2-(4-(1-(4-(trifluoromethoxy)phenyl)-1H-1,2,4-triazol-3-yl)phenyl)ethan-1-amine (C18)

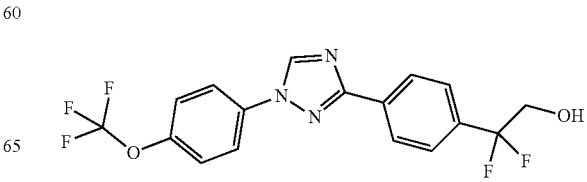

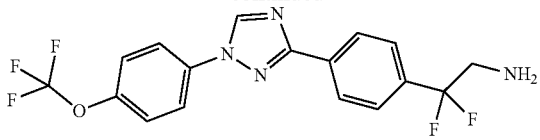

2,2-Difluoro-2-(4-(1-(4-(trifluoromethoxy)phenyl)-1H-1,2,4-triazol-3-yl)phenyl)-acetamide (C16; 109 mg, 0.27 mmol) in 1 M borane-THF complex in THF (1.1 mL, 1.1 mmol) was heated at 60° C. for 3 days. 2 N Hydrochloric acid (HCl) was added to the mixture, and the reaction mixture was stirred at 50° C. for 2 h. The mixture was cooled and made basic with 50% weight per weight (w/w) NaOH. The solution was diluted with water and extracted twice with ethyl acetate. The organic extracts were dried over sodium sulfate, filtered, and concentrated. The residue was purified by reverse-phase flash chromatography (0-100% acetonitrile/water) to provide a mixture of the title compounds. C17: ESIMS m z 386 ([M+H]+); C18: ESIMS m z 385 ([M+H]+).

Example 16: Preparation of 2,2-difluoro-2-(4-(1-(4-(trifluoromethoxy)phenyl)-1H-1,2,4-triazol-3-yl)phenyl)ethyl (2,5-dioxopyrrolidin-1-yl) carbonate (C19) and 2,5-dioxopyrrolidin-1-yl (2,2-difluoro-2-(4-(1-(4-(trifluoromethoxy)phenyl)-1H-1,2,4-triazol-3-yl)phenyl)ethyl)carbamate (C20)

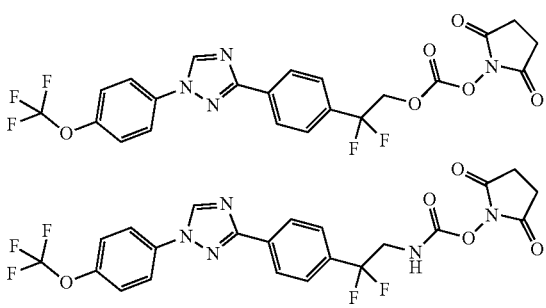

To a mixture of 2,2-difluoro-2-(4-(1-(4-(trifluoromethoxy)phenyl)-1H-1,2,4-triazol-3-yl)phenyl)ethanol (C17) and 2,2-difluoro-2-(4-(1-(4-(trifluoromethoxy)phenyl)-1H-1,2,4-triazol-3-yl)phenyl)ethanamine (C18; 320 mg, ~0.92 mmol) were added bis(2,5-dioxopyrrolidin-1-yl) carbonate (282 mg, 1.1 mmol), acetonitrile (3 mL), and pyridine (0.09 mL, 1.1 mmol). The reaction mixture was stirred at room temperature for 5 h and loaded directly onto a Celite® cartridge with acetonitrile. The cartridge was dried in a vacuum oven overnight. Purification by reverse-phase flash chromatography (0-100% acetonitrile/water) provided the title carbonate (25 mg, 43%) and the title carbamate (14 mg, 74% purity).

Carbonate C19: $^1$H NMR (400 MHz, CDCl$_3$) δ 8.59 (s, 1H), 8.31 (d, J=8.2 Hz, 2H), 7.84-7.79 (m, 2H), 7.65 (d, J=8.3 Hz, 2H), 7.43-7.38 (m, 2H), 4.69 (t, J=12.3 Hz, 2H), 2.83 (s, 4H); $^{19}$F NMR (376 MHz, CDCl$_3$) δ −58.02, −104.97; ESIMS m z 527 ([M+H]+).

Example 17: Preparation of 2,5-dioxopyrrolidin-1-yl (4-(1-(4-(trifluoromethoxy)phenyl)-1H-1,2,4-triazol-3-yl)phenethyl) Carbonate (C21)

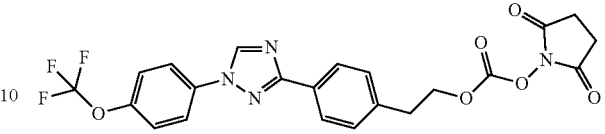

To 2-(4-(1-(4-(trifluoromethoxy)phenyl)-1H-1,2,4-triazol-3-yl)phenyl)ethan-1-ol (prepared as in Fischer, L. G. et al., U. S. Patent Application Publication 2014/0274688; 320 mg, 0.92 mmol) and bis(2,5-dioxopyrrolidin-1-yl) carbonate (282 mg, 1.1 mmol) in acetonitrile (3 mL) was added pyridine (0.09 mL, 1.1 mmol), and the reaction mixture was stirred at room temperature for 4 h. The reaction mixture was concentrated under nitrogen and loaded onto a Celite® cartridge with DCM. Purification by flash chromatography (0-100% ethyl acetate/hexanes) provided the title compound as a clear oil (498 mg, 100%): $^1$H NMR (400 MHz, CDCl$_3$) δ 8.62 (s, 1H), 8.17-8.12 (m, 2H), 7.85-7.78 (m, 2H), 7.43-7.31 (m, 4H), 4.55 (t, J=7.1 Hz, 2H), 3.13 (t, J=7.1 Hz, 2H), 2.84 (s, 4H); $^{19}$F NMR (376 MHz, CDCl$_3$) δ −58.02; ESIMS m z 491 ([M+H]+).

The following compounds were prepared according to the procedure in Example 17.

2,5-Dioxopyrrolidin-1-yl (4-(1-(4-(trifluoromethoxy)phenyl)-1H-1,2,4-triazol-3-yl)phenyl) Carbonate (C22)

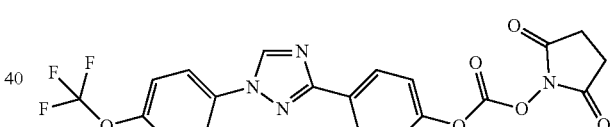

The title compound was prepared from compound C6 and isolated as a clear oil (56 mg, 28%): $^1$H NMR (400 MHz, CDCl$_3$) δ 8.70 (d, J=3.0 Hz, 1H), 8.27-8.19 (m, 2H), 7.86-7.77 (m, 2H), 7.45-7.37 (m, 4H), 2.90 (s, 4H); $^{19}$F NMR (376 MHz, CDCl$_3$) δ −58.01; ESIMS m z 463 ([M+H]+).

2,5-Dioxopyrrolidin-1-yl (1-(4-(1-(4-(trifluoromethoxy)phenyl)-1H-1,2,4-triazol-3-yl)phenyl)propan-2-yl) Carbonate (C23)

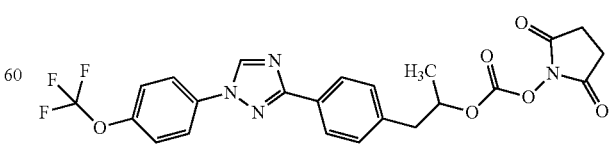

The title compound was prepared from compound C8 and isolated as a clear oil (97 mg, 98%); ESIMS m z 505 ([M+H]+).

Example 18: Preparation of 4-(1-(4-(trifluoromethoxy)phenyl)-1H-1,2,4-triazol-3-yl)phenethyl (Z)-(3-(2-isopropyl-5-methylphenyl)-4-oxothiazolidin-2-ylidene)carbamate (A1)

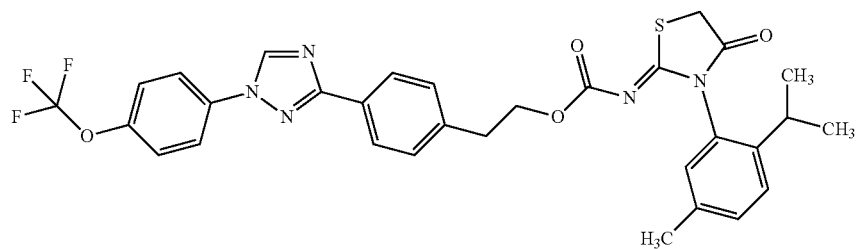 [SMILES: Cc1ccc(C(C)C)c(N2C(=O)CS/C2=N\C(=O)OCCc2ccc(-c3ncn(-c4ccc(OC(F)(F)F)cc4)n3)cc2)c1]

2,5-Dioxopyrrolidin-1-yl 4-(1-(4-(trifluoromethoxy)phenyl)-1H-1,2,4-triazol-3-yl)phenethyl carbonate (C21; 21.5 mg, 0.044 mmol), 2-imino-3-(2-isopropyl-5-methylphenyl)thiazolidin-4-one (prepared as in Fischer, L. G. et al., U. S. Patent Application Publication 2014/0274688; 16 mg, 0.064 mmol), and sodium bicarbonate (14 mg, 0.17 mmol) in DCM (0.2 mL) and water (0.1 mL) were stirred at room temperature overnight. The reaction mixture was diluted with DCM and filtered through a phase separator directly onto a Celite® cartridge. Purification by flash chromatography (0-100% ethyl acetate/B, where B=1:1 DCM/hexanes) provided the title compound as a white solid (18 mg, 65%).

The following compounds were prepared according to the procedure in Example 18.

4-(1-(4-(Trifluoromethoxy)phenyl)-1H-1,2,4-triazol-3-yl)phenethyl (Z)-(3-(2-isopropylphenyl)-4-oxothiazolidin-2-ylidene)carbamate (A2)

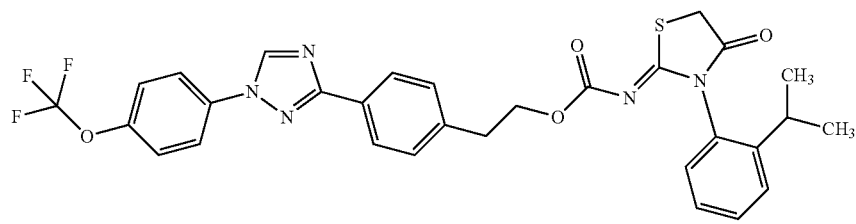 [SMILES: CC(C)c1ccccc1N1C(=O)CS/C1=N\C(=O)OCCc1ccc(-c2ncn(-c3ccc(OC(F)(F)F)cc3)n2)cc1]

The title compound was prepared from compound C21 and 2-imino-3-(2-isopropylphenyl)thiazolidin-4-one (prepared as in Baum, E. W. et al., PCT International Application WO 2016/033025 A1) and isolated as a white solid (51 mg, 80%).

4-(1-(4-(Trifluoromethoxy)phenyl)-1H-1,2,4-triazol-3-yl)phenyl (Z)-(3-(2-isopropyl-5-methylphenyl)-4-oxothiazolidin-2-ylidene)carbamate (A3)

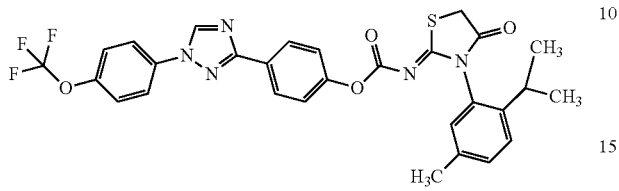

The title compound was prepared from compound C22 and 2-imino-3-(2-isopropyl-5-methylphenyl)thiazolidin-4-one (prepared as in Fischer, L. G. et al., U. S. Patent Application Publication 2014/0274688) and isolated as a white foamy solid (30 mg, 38%).

4-(1-(4-(Trifluoromethoxy)phenyl)-1H-1,2,4-triazol-3-yl)phenethyl (Z)-(3-(2-ethoxyphenyl)-4-oxothiazolidin-2-ylidene)carbamate (A5)

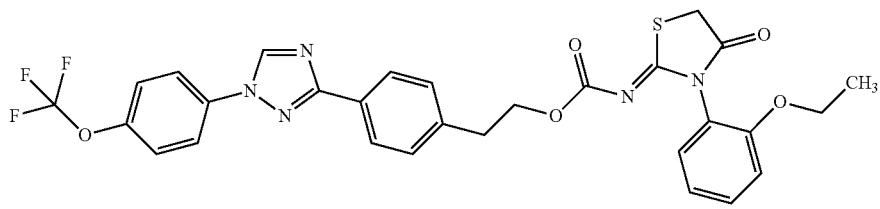 [SMILES: CCOc1ccccc1N1C(=O)CS/C1=N\C(=O)OCCc1ccc(-c2ncn(-c3ccc(OC(F)(F)F)cc3)n2)cc1]

The title compound was prepared from compound C21 and 3-(2-ethoxyphenyl)-2-iminothiazolidin-4-one (prepared as in Baum, E. W. et al., PCT International Application WO 2018/067764) and isolated as a yellow oil (28 mg, 31%).

4-(1-(4-(Trifluoromethoxy)phenyl)-1H-1,2,4-triazol-3-yl)phenethyl (Z)-(3-(2-butylphenyl)-4-oxothiazolidin-2-ylidene)carbamate (A6)

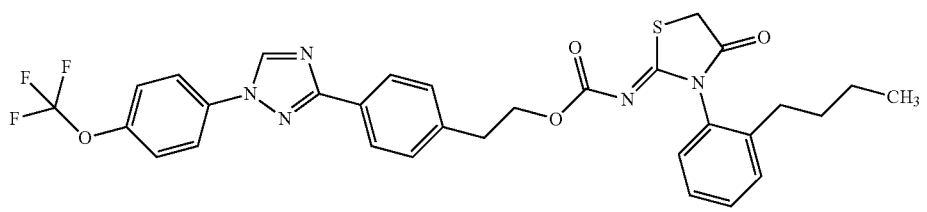 [SMILES: CCCCc1ccccc1N1C(=O)CS/C1=N\C(=O)OCCc1ccc(-c2ncn(-c3ccc(OC(F)(F)F)cc3)n2)cc1]

The title compound was prepared from compounds C21 and C44 and isolated as a cream solid (45 mg, 69%).

4-(1-(4-(Trifluoromethoxy)phenyl)-1H-1,2,4-triazol-3-yl)phenethyl (Z)-(3-(2-(2-cyclopropylethyl)phenyl)-4-oxothiazolidin-2-ylidene)carbamate (A7)

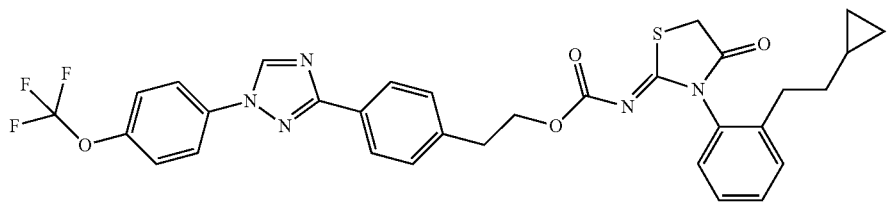 [SMILES: O=C(/N=C1\SCC(=O)N1c1ccccc1CCC1CC1)OCCc1ccc(-c2ncn(-c3ccc(OC(F)(F)F)cc3)n2)cc1]

The title compound was prepared from compounds C21 and C45 and isolated as a cream solid (43 mg, 61%).

4-(1-(4-(Trifluoromethoxy)phenyl)-1H-1,2,4-triazol-3-yl)phenethyl (Z)-(4-oxo-3-(2-(3,3,3-trifluoropropyl)phenyl)thiazolidin-2-ylidene)carbamate (A8)

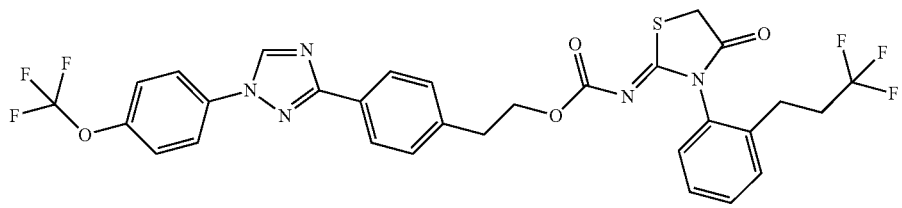 [SMILES: O=C(/N=C1\SCC(=O)N1c1ccccc1CCC(F)(F)F)OCCc1ccc(-c2ncn(-c3ccc(OC(F)(F)F)cc3)n2)cc1]

The title compound was prepared from compounds C21 and C47 and isolated as a cream solid (42 mg, 59%).

4-(1-(4-(Trifluoromethoxy)phenyl)-1H-1,2,4-triazol-3-yl)phenethyl ((Z)-4-oxo-3-(2-((E)-3,3,3-trifluoroprop-1-en-1-yl)phenyl)thiazolidin-2-ylidene)carbamate (A9)

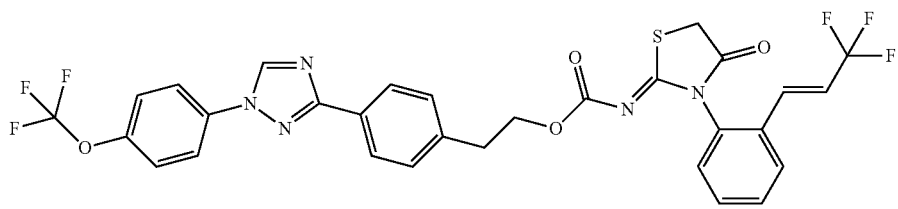 [SMILES: O=C(/N=C1\SCC(=O)N1c1ccccc1/C=C/C(F)(F)F)OCCc1ccc(-c2ncn(-c3ccc(OC(F)(F)F)cc3)n2)cc1]

The title compound was prepared from compounds C21 and C46 and isolated as a white solid (43 mg, 62%).

4-(1-(4-(Trifluoromethoxy)phenyl)-1H-1,2,4-triazol-3-yl)phenethyl (Z)-(3-(4-methoxy-2-methylphenyl)-4-oxothiazolidin-2-ylidene)carbamate (A10)

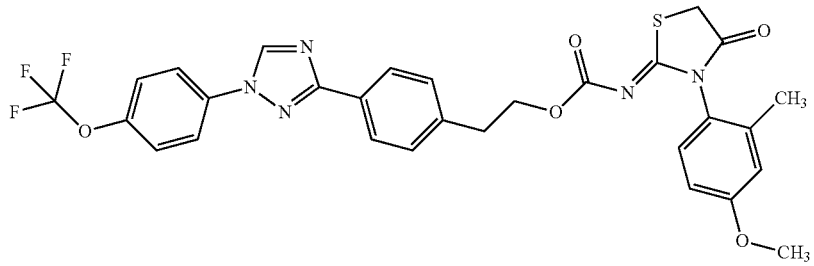 [SMILES: COc1ccc(N2C(=O)CS/C2=N\C(=O)OCCc2ccc(-c3ncn(-c4ccc(OC(F)(F)F)cc4)n3)cc2)c(C)c1]

The title compound was prepared from intermediates C21 and 2-imino-3-(4-methoxy-2-methylphenyl)thiazolidin-4-one (prepared as in Baum, E. W. et al., PCT International Application WO 2016/033025 A1) and isolated as a white solid (52 mg, 56%).

4-(1-(4-(Trifluoromethoxy)phenyl)-1H-1,2,4-triazol-3-yl)phenethyl (Z)-(3-(2-fluoro-5-methylphenyl)-4-oxothiazolidin-2-ylidene)carbamate (A11)

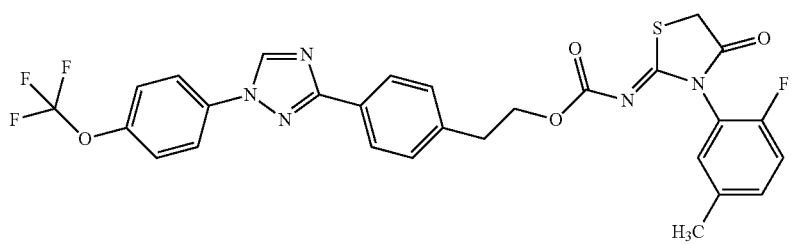 [SMILES: Cc1ccc(F)c(N2C(=O)CS/C2=N\C(=O)OCCc2ccc(-c3ncn(-c4ccc(OC(F)(F)F)cc4)n3)cc2)c1]

The title compound was prepared from compound C21 and 3-(2-fluoro-5-methylphenyl)-2-iminothiazolidin-4-one (prepared as in Giampietro, N. C. et al., PCT International Application WO 2017/040194 A1) and isolated as a white solid (47 mg, 76%).

4-(1-(4-(Trifluoromethoxy)phenyl)-1H-1,2,4-triazol-3-yl)phenethyl (Z)-(3-(2-chloro-5-methylphenyl)-4-oxothiazolidin-2-ylidene)carbamate (A12)

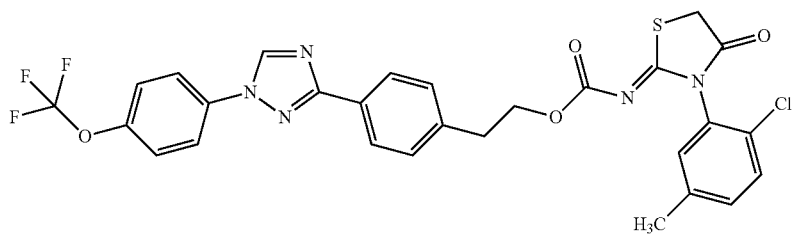 [SMILES: Cc1ccc(Cl)c(N2C(=O)CS/C2=N\C(=O)OCCc2ccc(-c3ncn(-c4ccc(OC(F)(F)F)cc4)n3)cc2)c1]

The title compound was prepared from compound C21 and 3-(2-chloro-5-methylphenyl)-2-iminothiazolidin-4-one (prepared as in Baum, E. W. et al., PCT International Application WO 2016/033025 A1) and isolated as a white solid (48 mg, 74%).

4-(1-(4-(Trifluoromethoxy)phenyl)-1H-1,2,4-triazol-3-yl)phenethyl (Z)-(3-(2-methoxy-5-methylphenyl)-4-oxothiazolidin-2-ylidene)carbamate (A13)

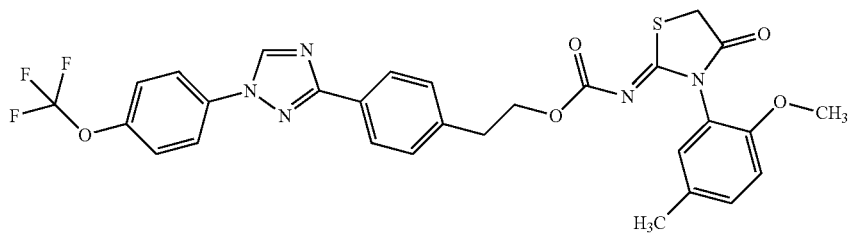 [SMILES: COc1ccc(C)cc1N1C(=O)CS/C1=N\C(=O)OCCc1ccc(-c2ncn(-c3ccc(OC(F)(F)F)cc3)n2)cc1]

The title compound was prepared from compound C21 and 2-imino-3-(2-methoxy-5-methylphenyl)thiazolidin-4-one (prepared as in Baum, E. W. et al., PCT International Application WO 2016/033025 A1) and isolated as a tan solid (40 mg, 60%).

4-(1-(4-(Trifluoromethoxy)phenyl)-1H-1,2,4-triazol-3-yl)phenethyl (Z)-(3-(5-methyl-2-(trifluoromethyl)phenyl)-4-oxothiazolidin-2-ylidene)carbamate (A14)

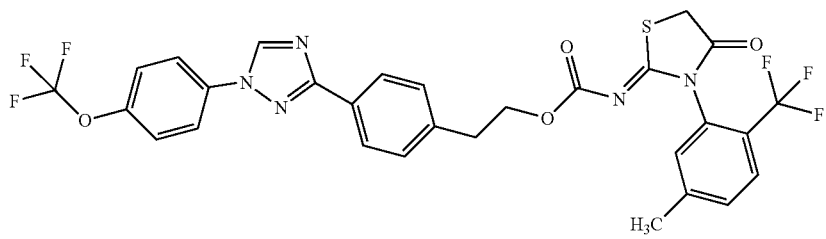 [SMILES: Cc1ccc(C(F)(F)F)c(N2C(=O)CS/C2=N\C(=O)OCCc2ccc(-c3ncn(-c4ccc(OC(F)(F)F)cc4)n3)cc2)c1]

The title compound was prepared from compound C21 and 2-imino-3-(5-methyl-2-(trifluoromethyl)phenyl)thiazolidin-4-one (prepared as in Giampietro, N. C. et al., PCT International Application WO 2017/040742 A1) and isolated as a white solid (19 mg, 28%).

4-(1-(4-(Trifluoromethoxy)phenyl)-1H-1,2,4-triazol-3-yl)phenethyl (Z)-(3-(5-methyl-2-propylphenyl)-4-oxothiazolidin-2-ylidene)carbamate (A15)

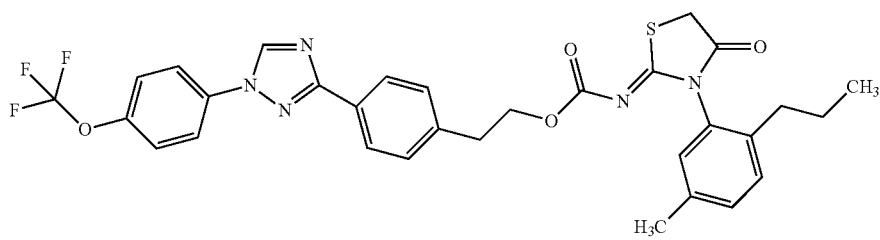 [SMILES: CCCc1ccc(C)cc1N1C(=O)CS/C1=N\C(=O)OCCc1ccc(-c2ncn(-c3ccc(OC(F)(F)F)cc3)n2)cc1]

The title compound was prepared from compound C21 and 2-imino-3-(5-methyl-2-propylphenyl)thiazolidin-4-one (prepared as in Baum, E. W. et al., PCT International Application WO 2016/033025 A1) and isolated as a white solid (45 mg, 68%).

4-(1-(4-(Trifluoromethoxy)phenyl)-1H-1,2,4-triazol-3-yl)phenethyl (Z)-(3-(2-ethoxy-5-methylphenyl)-4-oxothiazolidin-2-ylidene)carbamate (A16)

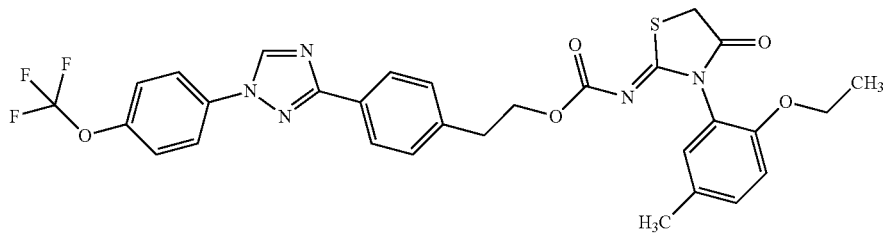 [SMILES: CCOc1ccc(C)cc1N1C(=O)CS/C1=N\C(=O)OCCc1ccc(-c2ncn(-c3ccc(OC(F)(F)F)cc3)n2)cc1]

The title compound was prepared from compound C21 and 3-(2-ethoxy-5-methylphenyl)-2-iminothiazolidin-4-one (prepared as in Giampietro, N. C. et al., PCT International Application WO 2017/040742 A1) and isolated as a tan solid (33 mg, 49%).

4-(1-(4-(Trifluoromethoxy)phenyl)-1H-1,2,4-triazol-3-yl)phenethyl (Z)-(3-(4-fluoro-2-isopropyl-5-methylphenyl)-4-oxothiazolidin-2-ylidene)carbamate (A17)

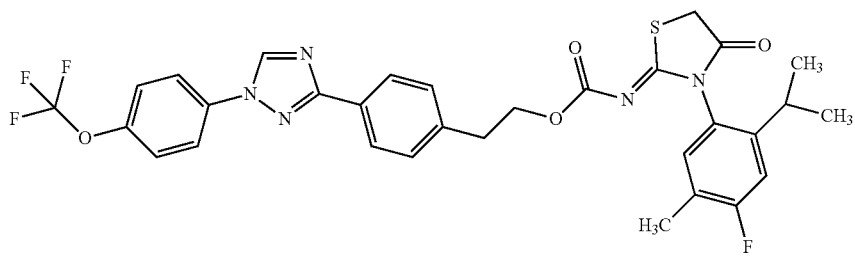 [SMILES: Cc1cc(N2C(=O)CS/C2=N\C(=O)OCCc2ccc(-c3ncn(-c4ccc(OC(F)(F)F)cc4)n3)cc2)c(C(C)C)cc1F]

The title compound was prepared from compound C21 and 3-(4-fluoro-2-isopropyl-5-methylphenyl)-2-iminothiazolidin-4-one (prepared as in Giampietro, N. C. et al., PCT International Application WO 2017/040742 A1) and isolated as a white solid (76 mg, 79%).

4-(1-(4-(Trifluoromethoxy)phenyl)-1H-1,2,4-triazol-3-yl)phenethyl (Z)-(3-(2-chloro-4,5-dimethylphenyl)-4-oxothiazolidin-2-ylidene)carbamate (A18)

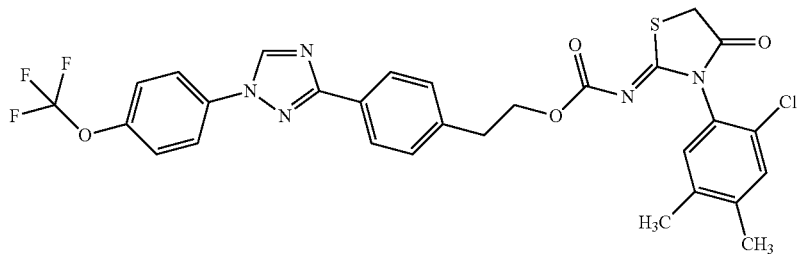 [SMILES: Cc1cc(Cl)c(N2C(=O)CS/C2=N\C(=O)OCCc2ccc(-c3ncn(-c4ccc(OC(F)(F)F)cc4)n3)cc2)cc1C]

The title compound was prepared from compounds C21 and C48 and isolated as a cream solid (50 mg, 75%).

1-(4-(1-(4-(Trifluoromethoxy)phenyl)-1H-1,2,4-triazol-3-yl)phenyl)propan-2-yl (Z)-(3-(2-isopropyl-5-methylphenyl)-4-oxothiazolidin-2-ylidene)carbamate (A19)

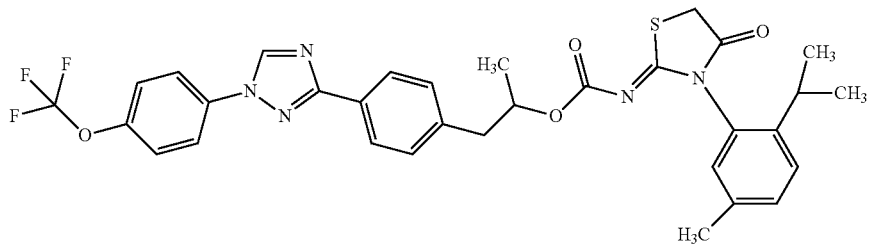 [SMILES: Cc1ccc(C(C)C)c(N2C(=O)CS/C2=N\C(=O)OC(C)Cc2ccc(-c3ncn(-c4ccc(OC(F)(F)F)cc4)n3)cc2)c1]

The title compound was prepared from compound C23 and 2-imino-3-(2-isopropyl-5-methylphenyl)thiazolidin-4-one (prepared as in Fischer, L. G. et al., U. S. Patent Application Publication 2014/0274688 and isolated as a tan solid (50 mg, 41%).

Example 19: Preparation of 4-(1-(4-(trifluoromethoxy)phenyl)-1H-1,2,4-triazol-3-yl)phenethyl (Z)-(3-(2-(methoxymethyl)phenyl)-4-oxothiazolidin-2-ylidene)carbamate (A27)

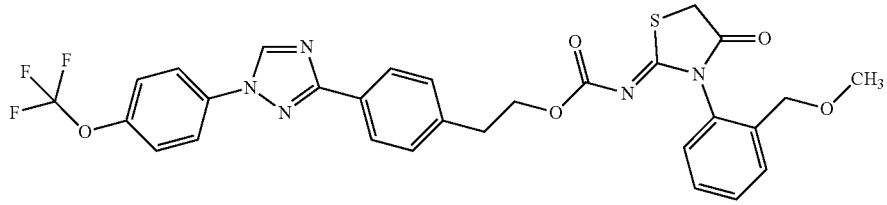 [SMILES: COCc1ccccc1N1C(=O)CS/C1=N\C(=O)OCCc1ccc(-c2ncn(-c3ccc(OC(F)(F)F)cc3)n2)cc1]

To 2-(4-(1-(4-(trifluoromethoxy)phenyl)-1H-1,2,4-triazol-3-yl)phenyl)ethan-1-ol (prepared as in Fischer, L. G. et al., U. S. Patent Application Publication 2014/0274688; 50 mg, 0.14 mmol) and bis(2,5-dioxopyrrolidin-1-yl) carbonate (48 mg, 0.19 mmol) in acetonitrile (0.72 mL) was added pyridine (0.045 mL, 0.57 mmol). The reaction was stirred at room temperature overnight. The reaction mixture was concentrated under a stream of nitrogen to provide C21. 2-Imino-3-(2-(methoxymethyl)phenyl)thiazolidin-4-one (C49; 34 mg, 0.14 mmol), DCM (0.5 mL), water (0.25 mL), and sodium bicarbonate (120 mg, 1.43 mmol) were added. The reaction mixture was stirred at room temperature overnight and filtered through a phase separator rinsing with DCM directly onto a Celite® cartridge. Purification by flash chromatography (0-100% ethyl acetate/hexanes) provided the title compound as a yellow oil (34 mg, 37%).

The following compounds were prepared according to the procedure in Example 19.

2-Fluoro-2-(4-(1-(4-(perfluoroethoxy)phenyl)-1H-1,2,4-triazol-3-yl)phenyl)ethyl (Z)-(3-(2-isopropylphenyl)-4-oxothiazolidin-2-ylidene)carbamate (A24)

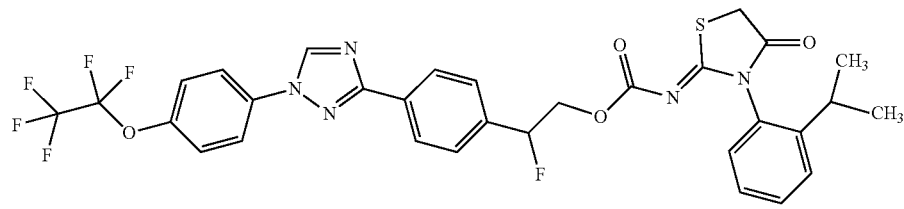 [SMILES: CC(C)c1ccccc1N1C(=O)CS/C1=N\C(=O)OCC(F)c1ccc(-c2ncn(-c3ccc(OC(F)(F)C(F)(F)F)cc3)n2)cc1]

The title compound was prepared from compound C12 and 2-imino-3-(2-isopropylphenyl)thiazolidin-4-one (prepared as in Baum, E. W. et al., PCT International Application WO 2016/033025 A1) and isolated as a yellow oil (77 mg, 90%).

2-Fluoro-2-(4-(1-(4-(perfluoroethoxy)phenyl)-1H-1,2,4-triazol-3-yl)phenyl)ethyl (Z)-(3-(5-chloro-2-isopropylphenyl)-4-oxothiazolidin-2-ylidene)carbamate (A25)

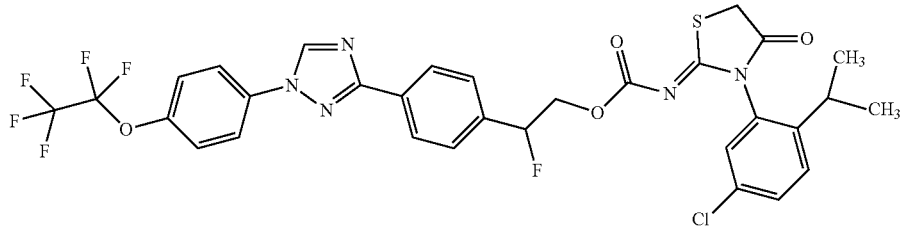 [SMILES: CC(C)c1ccc(Cl)cc1N1C(=O)CS/C1=N\C(=O)OCC(F)c1ccc(-c2ncn(-c3ccc(OC(F)(F)C(F)(F)F)cc3)n2)cc1]

The title compound was prepared from compound C12 and 3-(5-chloro-2-isopropylphenyl)-2-iminothiazolidin-4-one (prepared as in Baum, E. W. et al., PCT International Application WO 2016/033025 A1) and isolated as an orange oily solid (32 mg, 36%).

2-Fluoro-2-(4-(1-(4-(perfluoroethoxy)phenyl)-1H-1,2,4-triazol-3-yl)phenyl)ethyl (Z)-(3-(2-isopropyl-5-methylphenyl)-4-oxothiazolidin-2-ylidene)carbamate (A26)

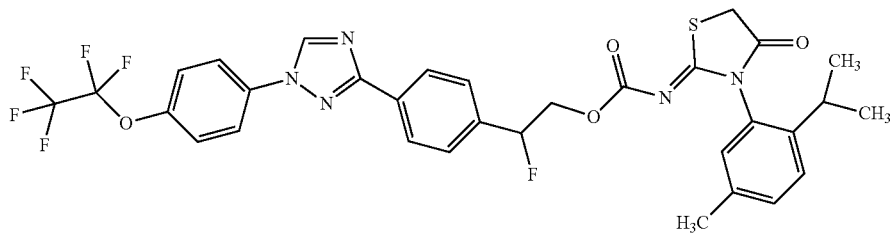 [SMILES: Cc1ccc(C(C)C)c(N2C(=O)CS/C2=N\C(=O)OCC(F)c2ccc(-c3ncn(-c4ccc(OC(F)(F)C(F)(F)F)cc4)n3)cc2)c1]

The title compound was prepared from compound C12 and 2-imino-3-(2-isopropyl-5-methylphenyl)thiazolidin-4-one (prepared as in Fischer, L. G. et al., U. S. Patent Application Publication 2014/0274688) and isolated as a white solid (19 mg, 22%).

4-(1-(4-(Trifluoromethoxy)phenyl)-1H-1,2,4-triazol-3-yl)phenethyl (Z)-(3-(2-(sec-butyl)-5-methoxyphenyl)-4-oxothiazolidin-2-ylidene)carbamate (A28)

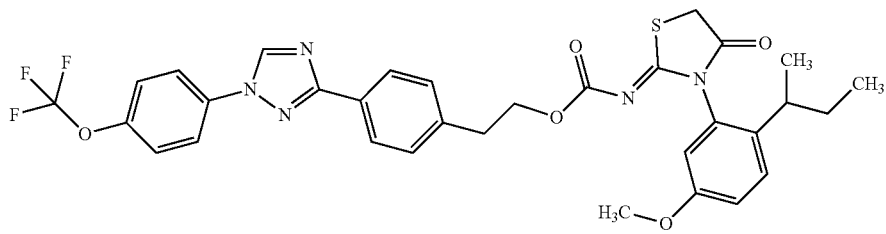 [SMILES: CCC(C)c1ccc(OC)cc1N1C(=O)CS/C1=N\C(=O)OCCc1ccc(-c2ncn(-c3ccc(OC(F)(F)F)cc3)n2)cc1]

The title compound was prepared from compounds C21 and C50 and isolated as a white solid (83 mg, 87%).

4-(1-(4-(Trifluoromethoxy)phenyl)-1H-1,2,4-triazol-3-yl)phenethyl (Z)-(3-(5-chloro-2-(trifluoromethoxy)phenyl)-4-oxothiazolidin-2-ylidene)carbamate (A29)

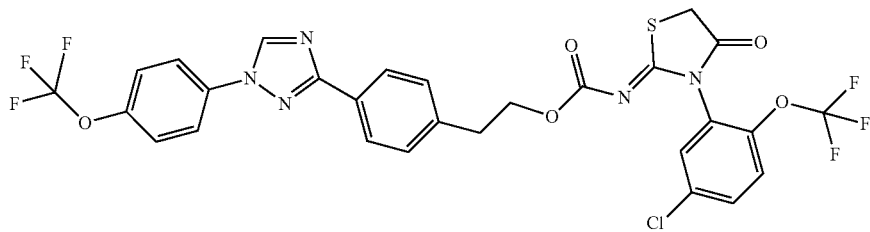 [SMILES: O=C(/N=C1\SCC(=O)N1c1cc(Cl)ccc1OC(F)(F)F)OCCc1ccc(-c2ncn(-c3ccc(OC(F)(F)F)cc3)n2)cc1]

The title compound was prepared from compounds C21 and C51 and isolated as a white solid (63 mg, 63%).

4-(1-(4-(Trifluoromethoxy)phenyl)-1H-1,2,4-triazol-3-yl)phenethyl (Z)-(3-(5-chloro-2-(2,2,2-trifluoroethoxy)phenyl)-4-oxothiazolidin-2-ylidene)carbamate (A30)

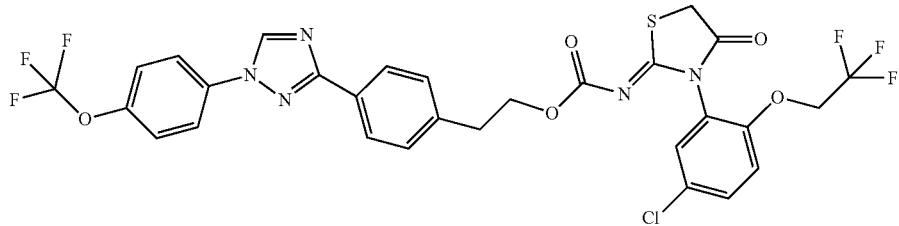 [SMILES: O=C(/N=C1\SCC(=O)N1c1cc(Cl)ccc1OCC(F)(F)F)OCCc1ccc(-c2ncn(-c3ccc(OC(F)(F)F)cc3)n2)cc1]

The title compound was prepared from compounds C21 and C52 and isolated as a yellow solid (77 mg, 75%).

4-(1-(4-(Trifluoromethoxy)phenyl)-1H-1,2,4-triazol-3-yl)phenethyl (Z)-(3-(5-methyl-2-(2,2,2-trifluoroethoxy)phenyl)-4-oxothiazolidin-2-ylidene)carbamate (A31)

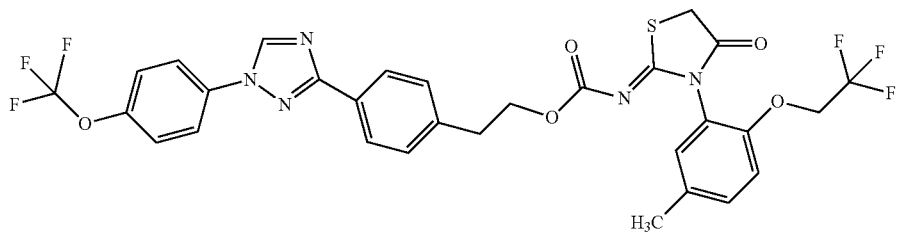 [SMILES: Cc1ccc(OCC(F)(F)F)c(N2C(=O)CS/C2=N\C(=O)OCCc2ccc(-c3ncn(-c4ccc(OC(F)(F)F)cc4)n3)cc2)c1]

The title compound was prepared from compounds C21 and 2-imino-3-(5-methyl-2-(2,2,2-trifluoroethoxy)phenyl)thiazolidin-4-one (prepared as in Giampietro, N. C. et al., PCT International Application WO 2017/040742 A1) and isolated as a white solid (94 mg, 92%).

4-(1-(4-(Trifluoromethoxy)phenyl)-1H-1,2,4-triazol-3-yl)phenethyl (Z)-(3-(2-ethyl-6-methylphenyl)-4-oxothiazolidin-2-ylidene)carbamate (A32)

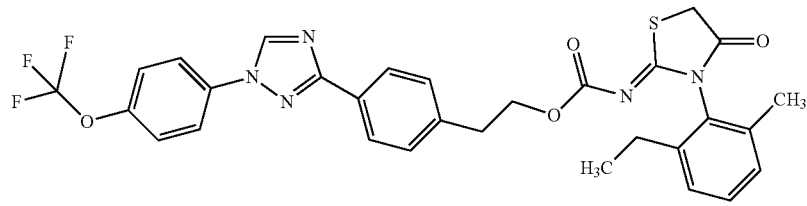 [SMILES: CCc1cccc(C)c1N1C(=O)CS/C1=N\C(=O)OCCc1ccc(-c2ncn(-c3ccc(OC(F)(F)F)cc3)n2)cc1]

The title compound was prepared from compounds C21 and 3-(2-ethyl-6-methylphenyl)-2-iminothiazolidin-4-one (prepared as in Baum, E. W. et al., PCT International Application WO 2016/033025 A1) and isolated as a white solid (87 mg, 95%).

4-(1-(4-(Trifluoromethoxy)phenyl)-1H-1,2,4-triazol-3-yl)phenethyl (Z)-(4-oxo-3-(5,6,7,8-tetrahydronaphthalen-1-yl)thiazolidin-2-ylidene)carbamate (A33)

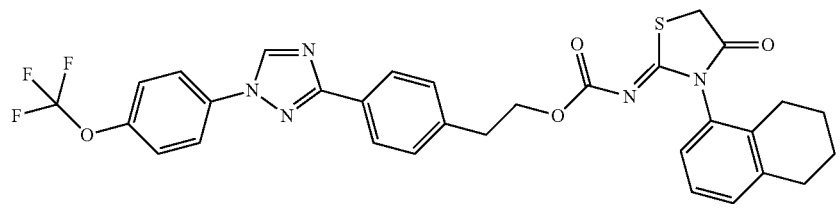 [SMILES: O=C(/N=C1\SCC(=O)N1c1cccc2c1CCCC2)OCCc1ccc(-c2ncn(-c3ccc(OC(F)(F)F)cc3)n2)cc1]

The title compound was prepared from compounds C21 and C53 and isolated as a tan solid (65 mg, 69%).

2-Fluoro-2-(4-(1-(4-(trifluoromethoxy)phenyl)-1H-1,2,4-triazol-3-yl)phenyl)ethyl (Z)-(3-(2-isopropylphenyl)-4-oxothiazolidin-2-ylidene)carbamate (A34)

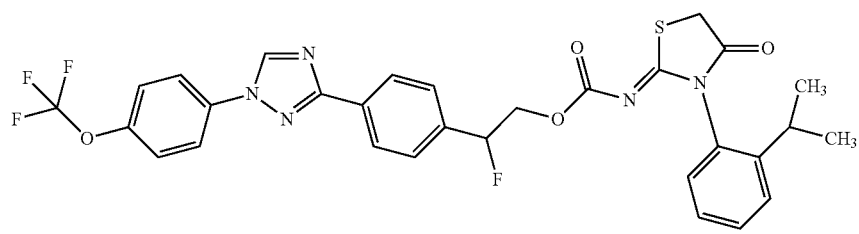 [SMILES: CC(C)c1ccccc1N1C(=O)CS/C1=N\C(=O)OCC(F)c1ccc(-c2ncn(-c3ccc(OC(F)(F)F)cc3)n2)cc1]

The title compound was prepared from compound C11 and 2-imino-3-(2-isopropylphenyl)thiazolidin-4-one (prepared as in Baum, E. W. et al., PCT International Application WO 2016/033025 A1) and isolated as a clear oil (22 mg, 25%).

4-(1-(4-(Trifluoromethoxy)phenyl)-1H-1,2,4-triazol-3-yl)phenethyl (Z)-(3-(2-(sec-butoxy)-5-methylphenyl)-4-oxothiazolidin-2-ylidene)carbamate (A35)

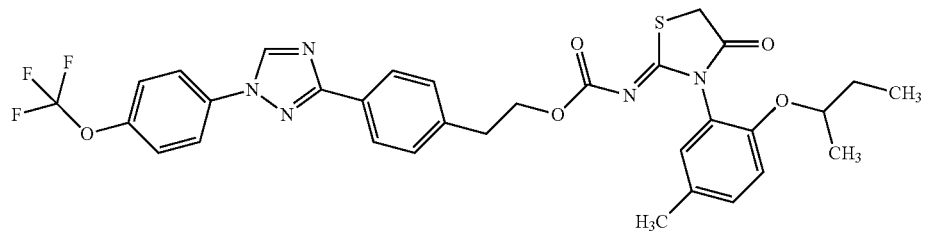 [SMILES: CCC(C)Oc1ccc(C)cc1N1C(=O)CS/C1=N\C(=O)OCCc1ccc(-c2ncn(-c3ccc(OC(F)(F)F)cc3)n2)cc1]

The title compound was prepared from compound C21 and 3-(2-(sec-butoxy)-5-methylphenyl)-2-iminothiazolidin-4-one (prepared as in Giampietro, N. C. et al., PCT International Application WO 2017/040742 A1) and isolated as an off-white solid (59 mg, 62%).

2-Fluoro-2-(4-(1-(4-(trifluoromethoxy)phenyl)-1H-1,2,4-triazol-3-yl)phenyl)ethyl (Z)-(3-(5-chloro-2-(trifluoromethoxy)phenyl)-4-oxothiazolidin-2-ylidene)carbamate (A36)

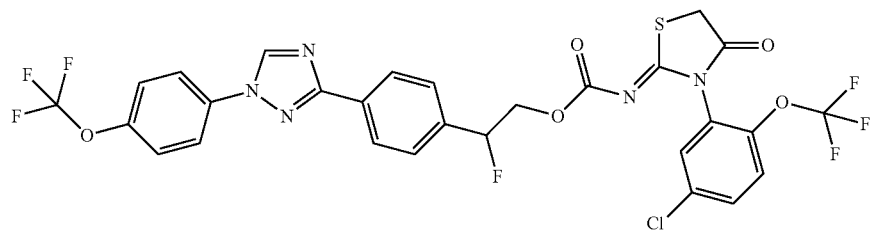 [SMILES: O=C(/N=C1\SCC(=O)N1c1cc(Cl)ccc1OC(F)(F)F)OCC(F)c1ccc(-c2ncn(-c3ccc(OC(F)(F)F)cc3)n2)cc1]

The title compound was prepared from compounds C11 and C51 and isolated as an orange oily solid (53 mg, 54%).

2-Fluoro-2-(4-(1-(4-(trifluoromethoxy)phenyl)-1H-1,2,4-triazol-3-yl)phenyl)ethyl (Z)-(3-(4-methoxy-2-methylphenyl)-4-oxothiazolidin-2-ylidene)carbamate (A37)

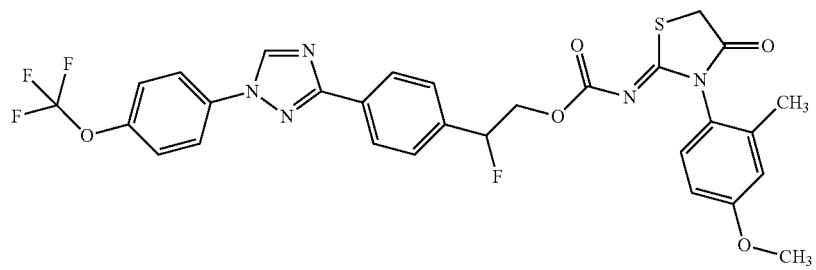 [SMILES: COc1ccc(N2C(=O)CS/C2=N\C(=O)OCC(F)c2ccc(-c3ncn(-c4ccc(OC(F)(F)F)cc4)n3)cc2)c(C)c1]

The title compound was prepared from compound C11 and 2-imino-3-(4-methoxy-2-methylphenyl)thiazolidin-4-one (prepared as in Baum, E. W. et al., PCT International Application WO 2016/033025 A1) and isolated as an off-white solid (24 mg, 27%).

2-Fluoro-2-(4-(1-(4-(trifluoromethoxy)phenyl)-1H-1,2,4-triazol-3-yl)phenyl)ethyl (Z)-(3-(2-chloro-4,5-dimethylphenyl)-4-oxothiazolidin-2-ylidene)carbamate (A38)

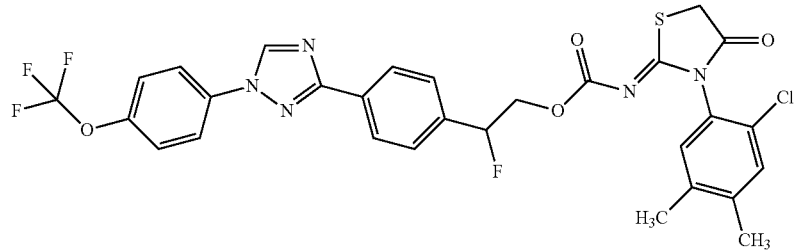 [SMILES: Cc1cc(Cl)c(N2C(=O)CS/C2=N\C(=O)OCC(F)c2ccc(-c3ncn(-c4ccc(OC(F)(F)F)cc4)n3)cc2)cc1C]

The title compound was prepared from compounds C11 and C48 and isolated as a tan solid (61 mg, 66%).

2-Fluoro-2-(4-(1-(4-(trifluoromethoxy)phenyl)-1H-1,2,4-triazol-3-yl)phenyl)ethyl (Z)-(4-oxo-3-(5,6,7,8-tetrahydronaphthalen-1-yl)thiazolidin-2-ylidene)carbamate (A39)

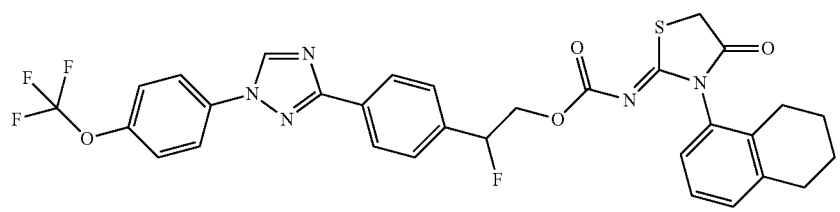 [SMILES: O=C(/N=C1\SCC(=O)N1c1cccc2c1CCCC2)OCC(F)c1ccc(-c2ncn(-c3ccc(OC(F)(F)F)cc3)n2)cc1]

The title compound was prepared from compounds C11 and C53 and isolated as an orange solid (79 mg, 86%).

2-Fluoro-2-(4-(1-(4-(trifluoromethoxy)phenyl)-1H-1,2,4-triazol-3-yl)phenyl)ethyl (Z)-(3-(2-ethoxyphenyl)-4-oxothiazolidin-2-ylidene)carbamate (A40)

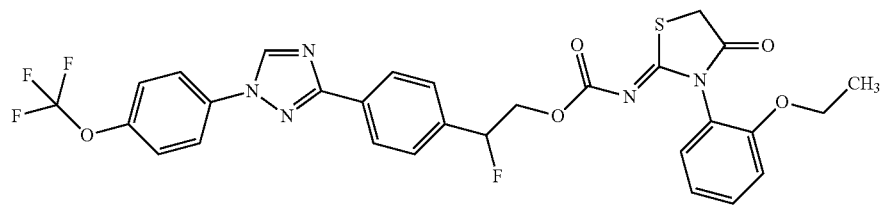 [SMILES: CCOc1ccccc1N1C(=O)CS/C1=N\C(=O)OCC(F)c1ccc(-c2ncn(-c3ccc(OC(F)(F)F)cc3)n2)cc1]

The title compound was prepared from compound C11 and 3-(2-ethoxyphenyl)-2-iminothiazolidin-4-one (prepared as in Baum, E. W. et al., PCT International Application WO 2018/067764) and isolated as a yellow oil (5.5 mg, 6%).

2-Fluoro-2-(4-(1-(4-(trifluoromethoxy)phenyl)-1H-1,2,4-triazol-3-yl)phenyl)ethyl (Z)-(3-(2-(sec-butoxy)-5-methylphenyl)-4-oxothiazolidin-2-ylidene)carbamate (A41)

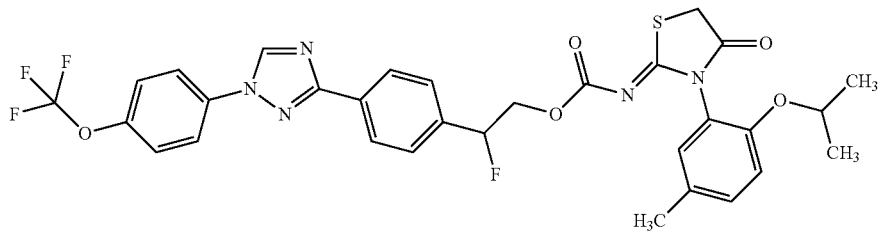 [SMILES: Cc1ccc(OC(C)C)c(N2C(=O)CS/C2=N\C(=O)OCC(F)c2ccc(-c3ncn(-c4ccc(OC(F)(F)F)cc4)n3)cc2)c1]

The title compound was prepared from compound C11 and 3-(2-(sec-butoxy)-5-methylphenyl)-2-iminothiazolidin-4-one (prepared as in Giampietro, N. C. et al., PCT International Application WO 2017/040742 A1) and isolated as an orange oily solid (40 mg, 42%).

2-Fluoro-2-(4-(1-(4-(trifluoromethoxy)phenyl)-1H-1,2,4-triazol-3-yl)phenyl)ethyl (Z)-(3-(2-ethyl-6-methylphenyl)-4-oxothiazolidin-2-ylidene)carbamate (A42)

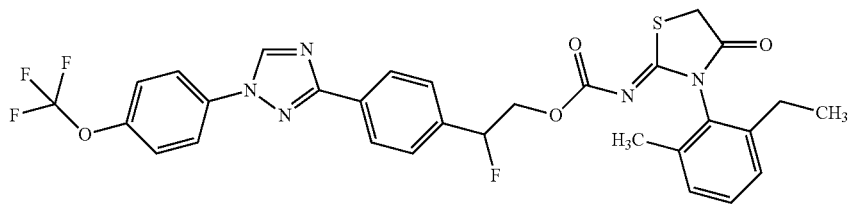 [SMILES: CCc1cccc(C)c1N1C(=O)CS/C1=N\C(=O)OCC(F)c1ccc(-c2ncn(-c3ccc(OC(F)(F)F)cc3)n2)cc1]

The title compound was prepared from compound C11 and 3-(2-ethyl-6-methylphenyl)-2-iminothiazolidin-4-one (prepared as in Baum, E. W. et al., PCT International Application WO 2016/033025 A1) and isolated as a white solid (29 mg, 33%).

4-(1-(4-(Perfluoroethoxy)phenyl)-1H-1,2,4-triazol-3-yl)phenethyl (Z)-(3-(5-chloro-2-isopropylphenyl)-4-oxothiazolidin-2-ylidene)carbamate (A43)

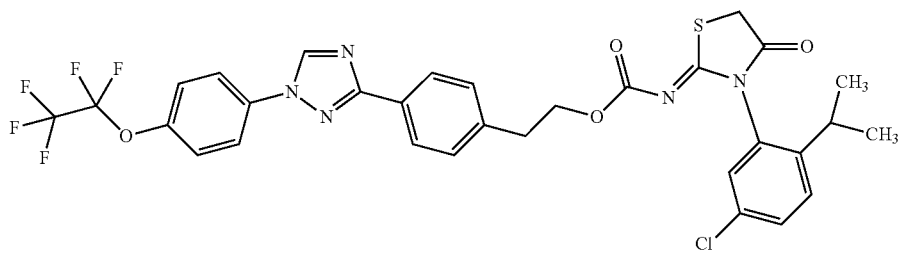 [SMILES: CC(C)c1ccc(Cl)cc1N1C(=O)CS/C1=N\C(=O)OCCc1ccc(-c2ncn(-c3ccc(OC(F)(F)C(F)(F)F)cc3)n2)cc1]

The title compound was prepared from compound C2 and 3-(5-chloro-2-isopropylphenyl)-2-iminothiazolidin-4-one (prepared as in Baum, E. W. et al., PCT International Application WO 2016/033025 A1) and isolated as an orange oily solid (42 mg, 38%).

4-(1-(4-(Perfluoroethoxy)phenyl)-1H-1,2,4-triazol-3-yl)phenethyl (Z)-(3-(2-isopropyl-5-methylphenyl)-4-oxothiazolidin-2-ylidene)carbamate (A44)

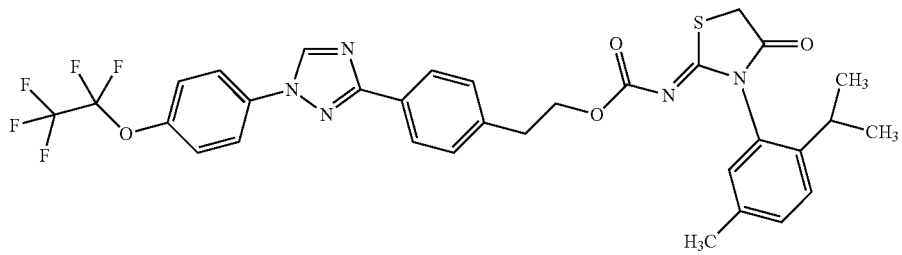 [SMILES: Cc1ccc(C(C)C)c(N2C(=O)CS/C2=N\C(=O)OCCc2ccc(-c3ncn(-c4ccc(OC(F)(F)C(F)(F)F)cc4)n3)cc2)c1]

The title compound was prepared from compound C2 and 2-imino-3-(2-isopropyl-5-methylphenyl)thiazolidin-4-one (prepared as in Fischer, L. G. et al., U. S. Patent Application Publication 2014/0274688; 16 mg, 0.064 mmol) and isolated as a tan solid (70 mg, 66%).

4-(1-(4-(Perfluoroethoxy)phenyl)-1H-1,2,4-triazol-3-yl)phenethyl (Z)-(3-(2-isopropylphenyl)-4-oxothiazolidin-2-ylidene)carbamate (A45)

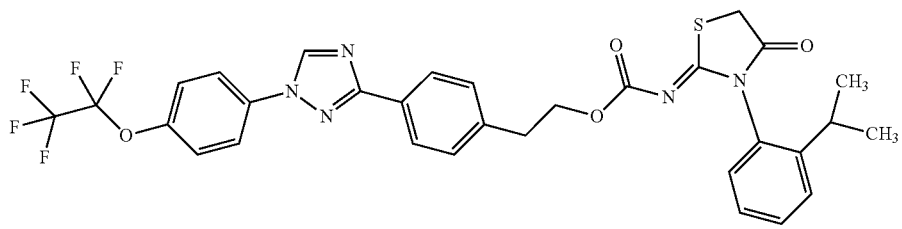 [SMILES: CC(C)c1ccccc1N1C(=O)CS/C1=N\C(=O)OCCc1ccc(-c2ncn(-c3ccc(OC(F)(F)C(F)(F)F)cc3)n2)cc1]

The title compound was prepared from compound C2 and 2-imino-3-(2-isopropylphenyl)thiazolidin-4-one (prepared as in Baum, E. W. et al., PCT International Application WO 2016/033025 A1) and isolated as a white solid (53 mg, 51%).

2-Chloro-2-(4-(1-(4-(trifluoromethoxy)phenyl)-1H-1,2,4-triazol-3-yl)phenyl)ethyl (Z)-(3-(2-isopropyl-5-methylphenyl)-4-oxothiazolidin-2-ylidene)carbamate (A46)

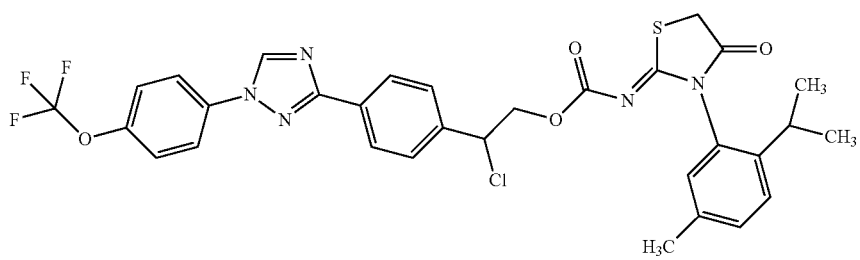 [SMILES: Cc1ccc(C(C)C)c(N2C(=O)CS/C2=N\C(=O)OCC(Cl)c2ccc(-c3ncn(-c4ccc(OC(F)(F)F)cc4)n3)cc2)c1]

The title compound was prepared from compound C13 and 2-imino-3-(2-isopropyl-5-methylphenyl)thiazolidin-4-one (prepared as in Fischer, L. G. et al., U. S. Patent Application Publication 2014/0274688) and isolated as a yellow oil (27 mg, 79%).

2-Chloro-2-(4-(1-(4-(trifluoromethoxy)phenyl)-1H-1,2,4-triazol-3-yl)phenyl)ethyl (Z)-(3-(2-isopropylphenyl)-4-oxothiazolidin-2-ylidene)carbamate (A47)

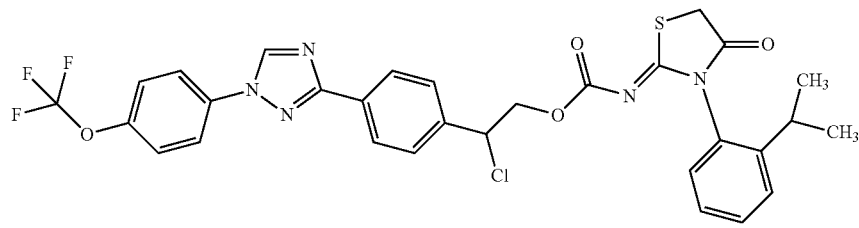 [SMILES: CC(C)c1ccccc1N1C(=O)CS/C1=N\C(=O)OCC(Cl)c1ccc(-c2ncn(-c3ccc(OC(F)(F)F)cc3)n2)cc1]

The title compound was prepared from compound C13 and 2-imino-3-(2-isopropylphenyl)thiazolidin-4-one (prepared as in Baum, E. W. et al., PCT International Application WO 2016/033025 A1) and isolated as a white sticky solid (38 mg, 54%).

2-Chloro-2-(4-(1-(4-(trifluoromethoxy)phenyl)-1H-1,2,4-triazol-3-yl)phenyl)ethyl (Z)-(3-(5-chloro-2-isopropylphenyl)-4-oxothiazolidin-2-ylidene)carbamate (A48)

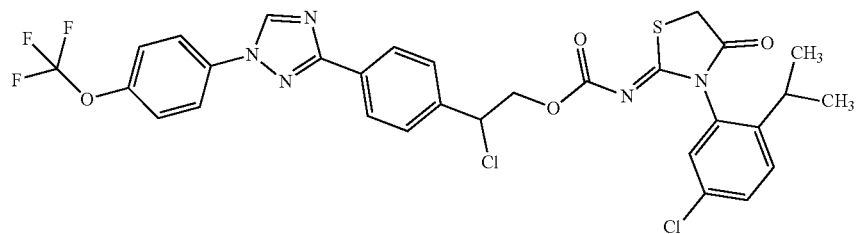 [SMILES: CC(C)c1ccc(Cl)cc1N1C(=O)CS/C1=N\C(=O)OCC(Cl)c1ccc(-c2ncn(-c3ccc(OC(F)(F)F)cc3)n2)cc1]

The title compound was prepared from compound C13 and 3-(5-chloro-2-isopropylphenyl)-2-iminothiazolidin-4-one (prepared as in Baum, E. W. et al., PCT International Application WO 2016/033025 A1) and isolated as a clear oil (34 mg, 47%).

1-(4-(1-(4-(Trifluoromethoxy)phenyl)-1H-1,2,4-triazol-3-yl)phenyl)propan-2-yl (Z)-(3-(2-(sec-butoxy)-5-methylphenyl)-4-oxothiazolidin-2-ylidene)carbamate (A49)

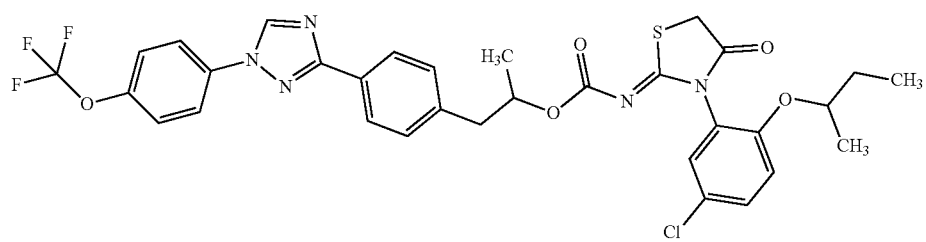 [SMILES: CCC(C)Oc1ccc(Cl)cc1N1C(=O)CS/C1=N\C(=O)OC(C)Cc1ccc(-c2ncn(-c3ccc(OC(F)(F)F)cc3)n2)cc1]

The title compound was prepared from compound C23 and 3-(2-(sec-butoxy)-5-methylphenyl)-2-iminothiazolidin-4-one (prepared as in Giampietro, N. C. et al., PCT International Application WO 2017/040742 A1) and isolated as a yellow oil (12 mg, 11%).

1-(4-(1-(4-(Trifluoromethoxy)phenyl)-1H-1,2,4-triazol-3-yl)phenyl)propan-2-yl (Z)-(3-(2-isopropylphenyl)-4-oxothiazolidin-2-ylidene)carbamate (A50)

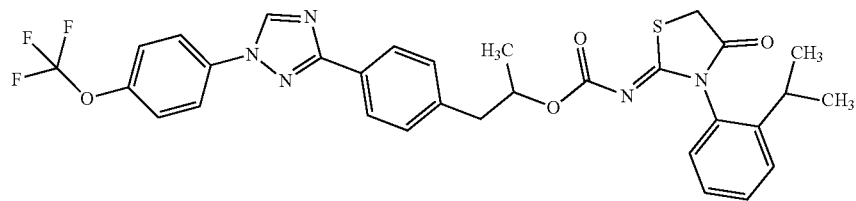 [SMILES: CC(Cc1ccc(-c2ncn(-c3ccc(OC(F)(F)F)cc3)n2)cc1)OC(=O)/N=C1\SCC(=O)N1c1ccccc1C(C)C]

The title compound was prepared from compound C23 and 2-imino-3-(2-isopropylphenyl)thiazolidin-4-one (prepared as in Baum, E. W. et al., PCT International Application WO 2016/033025 A1) and isolated as a tan oily foam (28 mg, 27%).

1-(4-(1-(4-(Trifluoromethoxy)phenyl)-1H-1,2,4-triazol-3-yl)phenyl)propan-2-yl (Z)-(3-(2-ethoxyphenyl)-4-oxothiazolidin-2-ylidene)carbamate (A51)

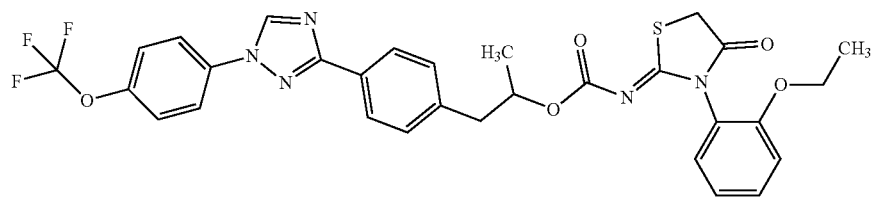 [SMILES: CCOc1ccccc1N1C(=O)CS/C1=N\C(=O)OC(C)Cc1ccc(-c2ncn(-c3ccc(OC(F)(F)F)cc3)n2)cc1]

The title compound was prepared from compound C23 and 3-(2-ethoxyphenyl)-2-iminothiazolidin-4-one (prepared as in Baum, E. W. et al., PCT International Application WO 2018/067764) and isolated as a yellow oil (17 mg, 16%).

1-(4-(1-(4-(Trifluoromethoxy)phenyl)-1H-1,2,4-triazol-3-yl)phenyl)propan-2-yl (Z)-(3-(2-ethyl-6-methylphenyl)-4-oxothiazolidin-2-ylidene)carbamate (A52)

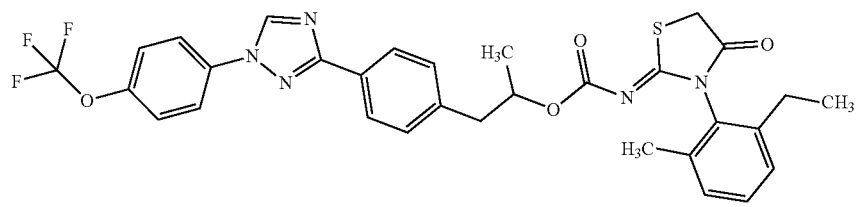 [SMILES: CCc1cccc(C)c1N1C(=O)CS/C1=N\C(=O)OC(C)Cc1ccc(-c2ncn(-c3ccc(OC(F)(F)F)cc3)n2)cc1]

The title compound was prepared from compound C23 and 3-(2-ethyl-6-methylphenyl)-2-iminothiazolidin-4-one (prepared as in Baum, E. W. et al., PCT International Application WO 2016/033025 A1) and isolated as an orange oily foam (42 mg, 40%).

4-(1-(4-(Trifluoromethoxy)phenyl)-1H-1,2,4-triazol-3-yl)phenethyl (Z)-(3-(2-isopropyl-5-methylphenyl)thiazol-2(3H)-ylidene)carbamate (A53)

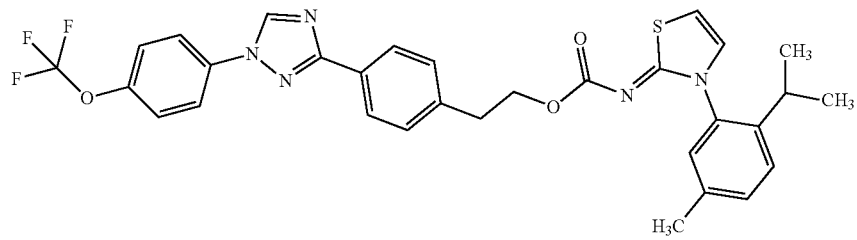

The title compound was prepared from intermediates C21 and 3-(2-isopropyl-5-methylphenyl)thiazol-2(3H)-imine (prepared as in Giampietro, N. C. et al., PCT International Application WO 2017/040742 A1) and isolated as a white solid (76 mg, 86%).

2-Fluoro-2-(4-(1-(4-(trifluoromethoxy)phenyl)-1H-1,2,4-triazol-3-yl)phenyl)ethyl (Z)-(3-(2-isopropyl-5-methylphenyl)thiazol-2(3H)-ylidene)carbamate (A54)

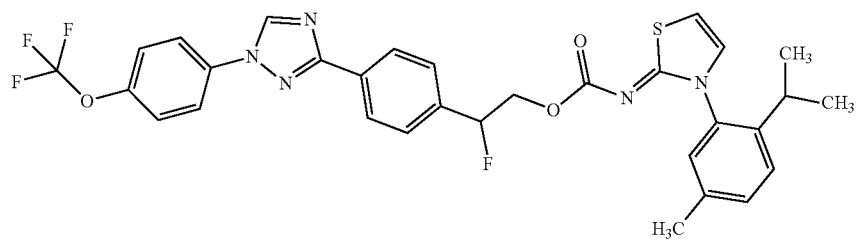 [SMILES: Cc1ccc(C(C)C)c(-n2ccs/c2=N\C(=O)OCC(F)c2ccc(-c3ncn(-c4ccc(OC(F)(F)F)cc4)n3)cc2)c1]

The title compound was prepared from compound C11 and 3-(2-isopropyl-5-methylphenyl)thiazol-2(3H)-imine (prepared as in Giampietro, N. C. et al., PCT International Application WO 2017/040742 A1) and isolated as a clear oil (56 mg, 64%). 1-(4-(1-(4-(Trifluoromethoxy)phenyl)-1H-1,2,4-triazol-3-yl)phenyl)propan-2-yl (Z)-(3-(2-isopropyl-5-methylphenyl)thiazol-2(3H)-ylidene)carbamate (A55)

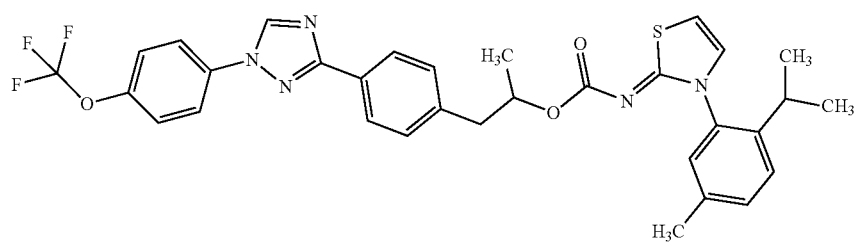 [SMILES: Cc1ccc(C(C)C)c(-n2ccs/c2=N\C(=O)OC(C)Cc2ccc(-c3ncn(-c4ccc(OC(F)(F)F)cc4)n3)cc2)c1]

The title compound was prepared from intermediates C23 and 3-(2-isopropyl-5-methylphenyl)thiazol-2(3H)-imine (prepared as in Giampietro, N. C. et al., PCT International Application WO 2017/040742 A1) and isolated as a white solid (44 mg, 41%).

Example 20: Preparation of 2-fluoro-2-(4-(1-(4-(trifluoromethoxy)phenyl)-1H-1,2,4-triazol-3-yl)phenyl)ethyl (Z)-(3-(2-isopropyl-5-methylphenyl)-4-oxothiazolidin-2-ylidene)carbamate (A20)

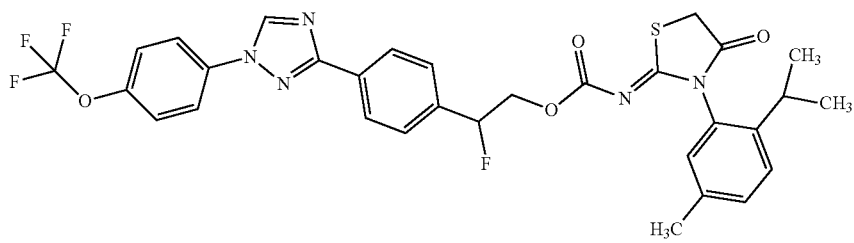

Bis(2,5-dioxopyrrolidin-1-yl) carbonate (42 mg, 0.16 mmol) was added to 2-fluoro-2-(4-(1-(4-(trifluoromethoxy)phenyl)-1H-1,2,4-triazol-3-yl)phenyl)ethan-1-ol (C11, 50 mg, 0.14 mmol) and triethylamine (0.02 mL, 0.14 mmol) in DCM (1 mL), and the reaction mixture was stirred at 23° C. overnight. 2-Imino-3-(2-isopropyl-5-methylphenyl)thiazolidin-4-one (prepared as in Fischer, L. G. et al., U. S. Patent Application Publication 2014/0274688; 34 mg, 0.14 mmol) was added, and the reaction mixture was stirred at 23° C. overnight. The reaction mixture was filtered through a phase separator, rinsing with DCM. The filtrate was concentrated onto silica gel. Purification by flash chromatography (silica/ethyl acetate/DCM-hexanes) yielded the title compound as an off-white solid (70 mg, 76%).

The following compounds were prepared according to the procedure in Example 20.

2-Fluoro-2-(4-(1-(4-(trifluoromethoxy)phenyl)-1H-1,2,4-triazol-3-yl)phenyl)ethyl (Z)-(3-(5-methyl-2-(2,2,2-trifluoroethoxy)phenyl)-4-oxothiazolidin-2-ylidene)carbamate (A21)

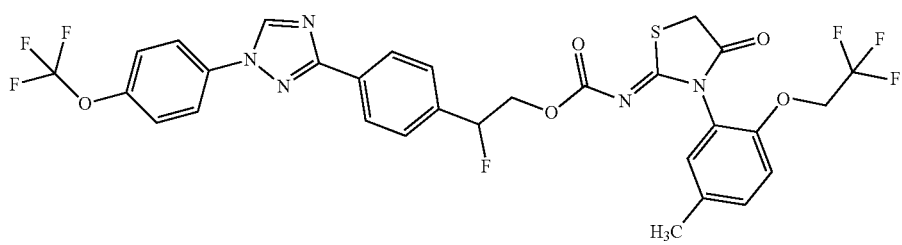

The title compound was prepared from intermediates C11 and 2-imino-3-(5-methyl-2-(2,2,2-trifluoroethoxy)phenyl)thiazolidin-4-one (prepared as in Giampietro, N. C. et al., PCT International Application WO 2017/040742 A1) and isolated as a white foam (73 mg, 73%). 2-Fluoro-2-(4-(1-(4-(trifluoromethoxy)phenyl)-1H-1,2,4-triazol-3-yl)phenyl) ethyl (Z)-(3-(5-chloro-2-(2,2,2-trifluoroethoxy)phenyl)-4-oxothiazolidin-2-ylidene)carbamate (A22)

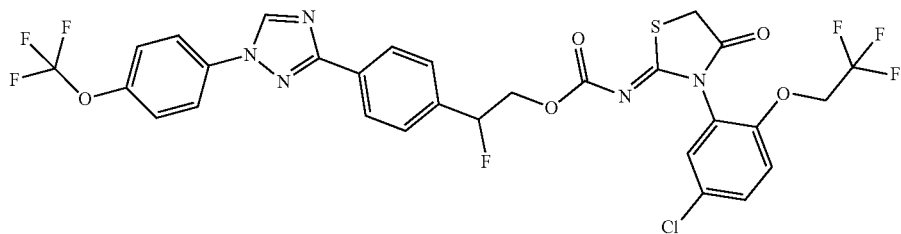 [SMILES: O=C(/N=C1\SCC(=O)N1c1cc(Cl)ccc1OCC(F)(F)F)OCC(F)c1ccc(-c2ncn(-c3ccc(OC(F)(F)F)cc3)n2)cc1]

The title compound was prepared from compounds C11 and C52 and isolated as a white foam (56 mg, 54%).

2-Fluoro-2-(4-(1-(4-(trifluoromethoxy)phenyl)-1H-1,2,4-triazol-3-yl)phenyl)ethyl (Z)-(3-(5-chloro-2-isopropylphenyl)-4-oxothiazolidin-2-ylidene)carbamate (A23)

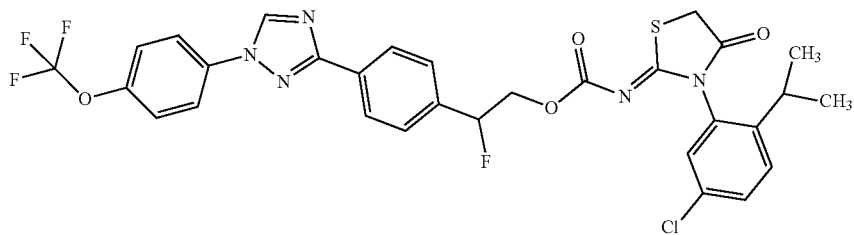 [SMILES: CC(C)c1ccc(Cl)cc1N1C(=O)CS/C1=N\C(=O)OCC(F)c1ccc(-c2ncn(-c3ccc(OC(F)(F)F)cc3)n2)cc1]

The title compound was prepared from compound C11 and 3-(5-chloro-2-isopropylphenyl)-2-iminothiazolidin-4-one (prepared as in Baum, E. W. et al., PCT International Application WO 2016/033025 A1) and isolated as a white foam (60 mg, 63%).

Example 21: Preparation of 2,2-difluoro-2-(4-(1-(4-(trifluoromethoxy)phenyl)-1H-1,2,4-triazol-3-yl)phenyl)ethyl (Z)-(3-(2-isopropyl-5-methylphenyl)-4-oxothiazolidin-2-ylidene)carbamate (A4)

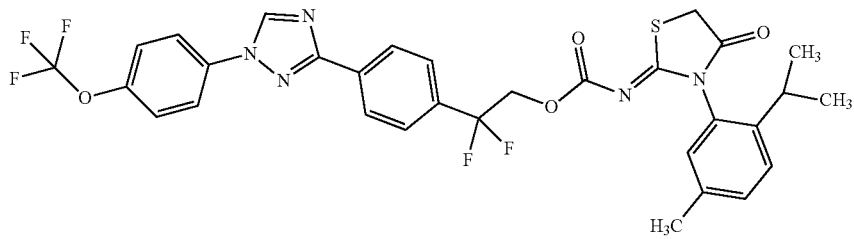 [SMILES: Cc1ccc(C(C)C)c(N2C(=O)CS/C2=N\C(=O)OCC(F)(F)c2ccc(-c3ncn(-c4ccc(OC(F)(F)F)cc4)n3)cc2)c1]

A mixture of 2,2-difluoro-2-(4-(1-(4-(trifluoromethoxy) phenyl)-1H-1,2,4-triazol-3-yl)phenyl)ethyl (2,5-dioxopyrrolidin-1-yl) carbonate (C19; 22 mg, 0.042 mmol), 2-imino-3-(2-isopropyl-5-methylphenyl)thiazolidin-4-one (prepared as in Fischer, L. G. et al., U. S. Patent Application Publication 2014/0274688; 20 mg, 0.081 mmol), and sodium bicarbonate (16 mg, 0.19 mmol) in DCM (0.5 mL) and water (0.1 mL) was stirred at room temperature for 3 h. The reaction mixture was filtered through a phase separator directly onto a Celite® cartridge, rinsing with DCM. Purification by flash chromatography (0-100% ethyl acetate/B, where B=1:1 DCM/hexanes) provided impure product. Further purification by flash chromatography (0-40, 40-40, 40-100% ethyl acetate/hexanes) provided the title compound as a white solid (21 mg, 75%).

Example 22: Preparation of (E)-1-(2-cyclopropylvinyl)-2-nitrobenzene (C24)

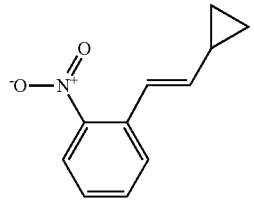

To a suspension of (cyclopropylmethyl)triphenylphosphonium bromide (3.57 g, 8.99 mmol) in THF (24 mL) at 0° C. under nitrogen was added 1 M potassium tert-butoxide (18 mL, 18 mmol). The reaction mixture was stirred at room temperature for 30 min. 2-Nitrobenzaldehyde (1.086 g, 7.19 mmol) was added, and the reaction mixture was stirred at room temperature for 1 h. The reaction was quenched with 1 N HCl and poured onto water. The mixture was extracted with ethyl acetate, and the organic extracts were dried over sodium sulfate and concentrated. Purification by flash chromatography (0-20% ethyl acetate/hexanes) provided the title compound as a brown oil (482 mg, 32%): $^1$H NMR (400 MHz, CDCl$_3$) δ 7.85 (dd, J=8.1, 1.3 Hz, 1H), 7.62-7.41 (m, 2H), 7.35-7.26 (m, 1H), 6.94 (d, J=15.6 Hz, 1H), 5.74 (dd, J=15.5, 9.2 Hz, 1H), 1.71-1.58 (m, 1H), 0.97-0.80 (m, 2H), 0.65-0.43 (m, 2H); EIMS m z 189.

Example 23: Preparation of 2-(2-cyclopropylethyl)aniline (C25)

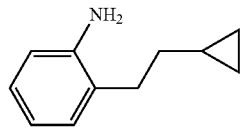 [SMILES: Nc1ccccc1CCC1CC1]

A flask containing a degassed solution of (E)-1-(2-cyclopropylvinyl)-2-nitrobenzene (C24; 683 mg, 3.61 mmol) and 10% palladium on carbon (154 mg, 1.44 mmol) was evacuated under vacuum and a balloon of hydrogen was added. The reaction mixture was stirred at room temperature for 20 h. The solution was diluted with ethyl acetate, filtered through Celite®, and concentrated. Purification by flash chromatography (0-100% ethyl acetate/hexanes) provided the title compound as a yellow oil (220 mg, 37%): $^1$H NMR (400 MHz, CDCl$_3$) δ 7.13-6.97 (m, 2H), 6.73 (td, J=7.5, 1.3 Hz, 1H), 6.68 (dd, J=7.8, 1.2 Hz, 1H), 3.64 (s, 2H), 2.68-2.54 (m, 2H), 1.58-1.46 (m, 2H), 0.81-0.67 (m, 1H), 0.52-0.39 (m, 2H), 0.13-0.04 (m, 2H); $^{13}$C NMR (101 MHz, CDCl$_3$) δ 171.59, 144.53, 129.89, 127.27, 119.16, 115.94, 34.50, 31.62, 11.39, 5.03; EIMS m z 161.

Example 24: Preparation of (E)-2-(3,3,3-trifluoroprop-1-en-1-yl)aniline (C26)

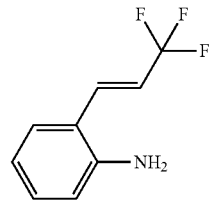 [SMILES: Nc1ccccc1/C=C/C(F)(F)F]

To three separate 20 mL microwave vials were added potassium carbonate (1.704 g, 12.33 mmol), palladium(II) acetate (0.018 g, 0.082 mmol), and 2-iodoaniline (0.9 g, 4.11 mmol). The vials were evacuated under vacuum and backfilled with nitrogen. The solids were dissolved in dry DMF (17 mL) and stirred. 1,1,1-Trifluoro-3-iodopropane (0.482 mL, 4.11 mmol) was added via syringe. The reaction mixtures were heated in the microwave at 200° C. for 1 h each. Each solution was diluted in hexanes and washed with water. The hexanes layers were separated and combined. The aqueous layer was extracted with ethyl acetate and then combined with the hexanes. All organic layers were dried and concentrated. Purification by flash chromatography (0-10% ethyl acetate/hexanes) provided the title compound as an orange solid (1.10 g, 42%): $^1$H NMR (400 MHz, CDCl$_3$) δ 7.32-7.26 (m, 1H), 7.23 (q, J=2.3 Hz, 1H), 7.21-7.15 (m, 1H), 6.87-6.74 (m, 1H), 6.72 (dd, J=8.0, 1.1 Hz, 1H), 6.23-6.00 (m, 1H), 3.82 (s, 2H); $^{19}$F NMR (376 MHz, CDCl$_3$) δ −63.13; EIMS m z 187.

Example 25: Preparation of 2-(3,3,3-trifluoropropyl)aniline (C27)

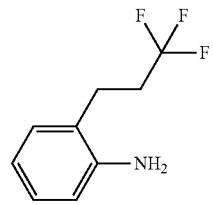 [SMILES: Nc1ccccc1CCC(F)(F)F]

To a dry, evacuated 250 mL round-bottomed flask were added (E)-2-(3,3,3-trifluoroprop-1-en-1-yl)aniline (C26; 1.61 g, 8.60 mmol), methanol (30 mL), and palladium(II) hydroxide on carbon (0.483 g, 3.44 mmol). The flask was evacuated and backfilled with nitrogen, then evacuated and filled with hydrogen by balloon. The reaction mixture was stirred at room temperature for 24 h. The solution was diluted in ethyl acetate and filtered through Celite®. The filtrate was concentrated. The title compound was isolated as an orange oil (1.45 g, 88%): $^1$H NMR (400 MHz, CDCl$_3$) δ 7.09 (td, J=7.7, 1.6 Hz, 1H), 7.04 (dd, J=7.5, 1.5 Hz, 1H), 6.77 (td, J=7.4, 1.2 Hz, 1H), 6.71 (dd, J=7.9, 1.3 Hz, 1H), 3.62 (s, 2H), 2.83-2.63 (m, 2H), 2.51-2.29 (m, 2H); $^{13}$C NMR (101 MHz, CDCl$_3$) δ 144.48, 129.68, 128.38, 125.97, 123.50, 119.57, 116.42, 33.15, 24.31; EIMS m/z 189.

Example 26: Preparation of 1-(methoxymethyl)-2-nitrobenzene (C28)

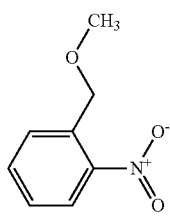

(2-Nitrophenyl)methanol (2 g, 13.1 mmol) was dissolved in THF (52 mL) and cooled to 0° C. To this mixture was added a 60% mineral oil dispersion of sodium hydride (0.575 g, 14.4 mmol) in portions. The mixture was stirred at 0° C. for 30 min, and methyl iodide (2.45 mL, 39.2 mmol) was added. The mixture was stirred an additional 90 min. The reaction was quenched with a saturated aqueous ammonium chloride solution and extracted with diethyl ether. The combined organic extracts were washed with brine, dried, and concentrated. Purification of the resulting yellow oil by flash chromatography (0-30% acetone/hexanes) provided the title compound as a clear yellow oil (1.45 g, 67%): $^1$H NMR (400 MHz, CDCl$_3$) δ 8.07 (dd, J=8.2, 1.4 Hz, 1H), 7.79 (dd, J=7.8, 1.3 Hz, 1H), 7.65 (td, J=7.6, 1.3 Hz, 1H), 7.47-7.41 (m, 1H), 4.85 (s, 2H), 3.50 (s, 3H); EIMS m z 166.

Example 27: Preparation of 2-(methoxymethyl)aniline (C29)

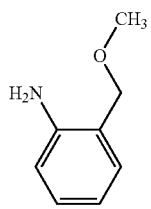

5% Palladium on carbon (0.926 g, 0.44 mmol) was added to 1-(methoxymethyl)-2-nitrobenzene (C28; 1.45 g, 8.70 mmol) dissolved in ethanol (17.4 mL) and ethyl acetate (17.4 mL). The flask was evacuated and backfilled with a balloon of hydrogen. The reaction mixture was stirred at room temperature overnight, filtered through Celite®, and concentrated. Purification by flash chromatography (0-30% ethyl acetate/hexanes) provided the title compound as a pale yellow oil (923 mg, 77%): $^1$H NMR (400 MHz, CDCl$_3$) δ 7.13 (td, J=7.6, 1.6 Hz, 1H), 7.10-7.00 (m, 1H), 6.74-6.65 (m, 2H), 4.48 (s, 2H), 4.15 (s, 2H), 3.34 (s, 3H); EIMS m z 137.

Example 28: Preparation of (E)-1-(but-2-en-2-yl)-4-methoxy-2-nitrobenzene (C30)

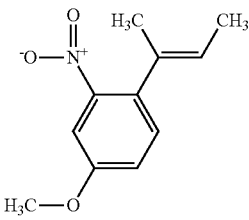

To a suspension of 1-bromo-4-methoxy-2-nitrobenzene (2.8 g, 12.1 mmol) in DMF (40 mL), degassed with argon, were added (E)-but-2-en-2-yltributylstannane (prepared as in *Org. Lett.* 2013, 15, 670-673; 4.5 g, 18.2 mmol), cesium fluoride (3.7 g, 24.2 mmol), and bis(triphenylphosphine) palladium(II) dichloride (Pd(PPh$_3$)$_2$Cl$_2$; 850 mg, 1.2 mmol), and the reaction mixture was stirred at 80° C. for 16 h. The reaction mixture was cooled to room temperature, poured into water and extracted with ethyl acetate (2×50 mL). The organic layer was washed with brine, dried over sodium sulfate, filtered, and concentrated under reduced pressure. Purification by column chromatography (10-20% ethyl acetate/petroleum ether) provided the title compound as a brown oil (1.5 g, 60%): $^1$H NMR (300 MHz, CDCl$_3$) δ 7.32 (d, J=2.7 Hz, 1H), 7.17 (d, J=8.4 Hz, 1H), 7.05 (dd, J=3.3, 8.4 Hz, 1H), 5.42 (q, J=1.5 Hz, 1H), 3.85 (s, 3H), 1.90 (s, 3H), 1.73 (d, J=6.6 Hz, 3H); ESIMS m z 208 ([M+H]$^+$).

Example 29: Preparation of 2-(sec-butyl)-5-methoxyaniline (C31)

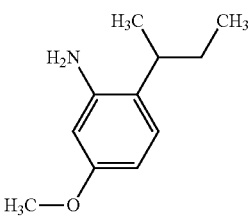

To a solution of (E)-1-(but-2-en-2-yl)-4-methoxy-2-nitrobenzene (C30; 1.5 g, 7.25 mmol) in ethyl acetate (50 mL) was added 10% palladium on carbon (1 g), and the reaction mixture was stirred under hydrogen gas (100 psi) in a Parr Shaker for 36 h. The reaction mixture was filtered through a pad of Celite®, washed with ethyl acetate, and the filtrate was concentrated under reduced pressure. The title compound was isolated as a brown liquid (3 g, crude), which was used in the next step without purification.

Example 30: Preparation of 4-chloro-2-nitro-1-(2,2,2-trifluoroethoxy)benzene (C32)

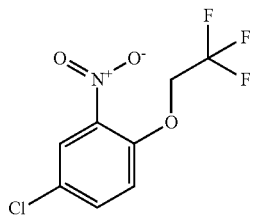 [SMILES: O=[N+]([O-])c1cc(Cl)ccc1OCC(F)(F)F]

To 4-chloro-2-nitrophenol (2 g, 11.5 mmol) in acetone (25 mL) were added sequentially potassium carbonate (3.19 g, 23.1 mmol) and 2,2,2-trifluoroethyl trifluoromethanesulfonate (2.5 mL, 17.3 mmol). The reaction mixture was stirred overnight under nitrogen then warmed to 60° C. for 3 h. The mixture was cooled to room temperature and diluted with ethyl acetate and water. The organic layer was separated and washed with brine, dried over sodium sulfate, filtered and concentrated. The title compound was isolated as a red solid (2.8 g, 90%): mp 59-61° C.; $^1$H NMR (400 MHz, CDCl$_3$) δ 7.90 (d, J=2.6 Hz, 1H), 7.55 (dd, J=8.9, 2.6 Hz, 1H), 7.09 (d, J=8.9 Hz, 1H), 4.48 (q, J=7.9 Hz, 2H); $^{19}$F NMR (376 MHz, CDCl$_3$) δ −73.74; EIMS m z 255.

Example 31: Preparation of 5-chloro-2-(2,2,2-trifluoroethoxy)aniline (C33)

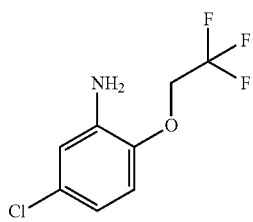 [SMILES: Nc1cc(Cl)ccc1OCC(F)(F)F]

To 4-chloro-2-nitro-1-(2,2,2-trifluoroethoxy)benzene (C32; 2.75 g, 10.8 mmol) and ammonium chloride (0.288 g, 5.38 mmol) in ethanol (20 mL) and water (5 mL) was added iron (3.00 g, 53.8 mmol). The reaction mixture was heated to 70° C. for 3 h under nitrogen. The mixture was cooled to room temperature and filtered through Celite®. The filtrate was diluted with ethyl acetate and water. The organic layer was separated and washed with brine, dried over sodium sulfate, filtered and concentrated. The title compound was isolated as a brown oil (2.63 g, 100%): $^1$H NMR (400 MHz, CDCl$_3$) δ 6.78-6.61 (m, 3H), 4.33 (q, J=8.1 Hz, 2H), 3.91 (s, 2H); $^{19}$F NMR (376 MHz, CDCl$_3$) δ −74.13; ESIMS m z 226 ([M+H]$^+$).

Example 32: Preparation of N-(2-butylphenyl)-2-chloroacetamide (C34)

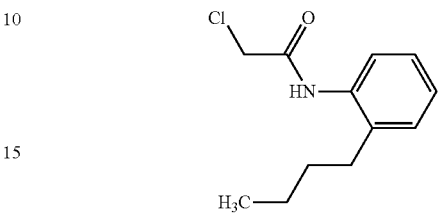

To a solution of commercially available 2-butylaniline (1 g, 6.70 mmol) in ethyl acetate (5 mL) in an ice bath was added sodium bicarbonate (1.12 g, 13.4 mmol) in portions. A solution of chloroacetyl chloride (0.64 mL, 8.0 mmol) in ethyl acetate (1 mL) was added. A white precipitate formed and the suspension was stirred at room temperature for 30 min. The reaction mixture was diluted in ethyl acetate and washed with water. The organic layer was dried over sodium sulfate and concentrated. The title compound was isolated as a white solid (1.41 g, 92%): $^1$H NMR (400 MHz, CDCl$_3$) δ 8.32 (s, 1H), 7.91 (dd, J=8.0, 1.4 Hz, 1H), 7.25-7.18 (m, 2H), 7.15 (dd, J=7.3, 1.3 Hz, 1H), 4.25 (s, 2H), 2.70-2.48 (m, 2H), 1.67-1.50 (m, 2H), 1.48-1.32 (m, 2H), 0.95 (t, J=7.3 Hz, 3H); $^{13}$C NMR (101 MHz, CDCl$_3$) δ 164.20, 134.61, 133.95, 130.26, 127.35, 126.27, 123.18, 43.71, 32.54, 31.72, 23.05, 14.37; EIMS m z 225.

The following compounds were prepared according to the procedure in Example 32.

2-Chloro-N-(2-(2-cyclopropylethyl)phenyl)acetamide (C35)

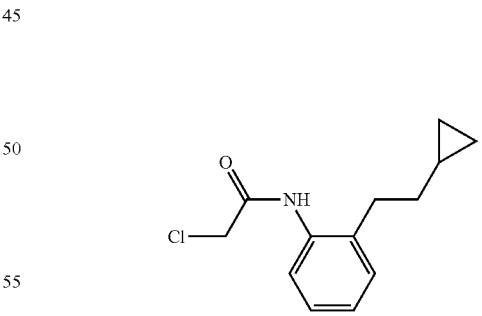

The title compound was prepared from compound C25 and isolated as a pink solid (391 mg, 100% yield): $^1$H NMR (400 MHz, CDCl$_3$) δ 8.39 (s, 1H), 7.85 (dd, J=7.9, 1.3 Hz, 1H), 7.25-7.20 (m, 2H), 7.19-7.12 (m, 1H), 4.12 (s, 2H), 2.79-2.66 (m, 2H), 1.51 (q, J=7.2 Hz, 2H), 0.76-0.65 (m, 1H), 0.55-0.35 (m, 2H), 0.11-0.01 (m, 2H); $^{13}$C NMR (101 MHz, CDCl$_3$) δ 164.68, 134.48, 134.12, 130.40, 127.33, 126.51, 123.56, 43.66, 41.02, 35.81, 31.87, 11.07, 5.04; ESIMS m z 238 ([M+H]$^+$).

113

(E)-2-Chloro-N-(2-(3,3,3-trifluoroprop-1-en-1-yl)phenyl)acetamide (C36)

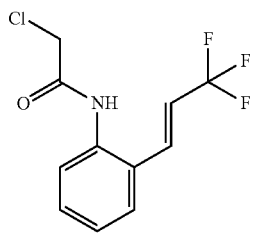 [SMILES: O=C(CCl)Nc1ccccc1/C=C/C(F)(F)F]

The title compound was prepared from compound C26 and isolated as a peach solid (777 mg, 91%): $^1$H NMR (400 MHz, CDCl$_3$) δ 8.27 (s, 1H), 7.79-7.73 (m, 1H), 7.50 (dd, J=7.8, 1.5 Hz, 1H), 7.43 (td, J=7.8, 1.6 Hz, 1H), 7.32-7.26 (m, 2H), 6.21 (dq, J=16.0, 6.4 Hz, 1H), 4.26 (s, 2H); $^{13}$C NMR (101 MHz, CDCl$_3$) δ 164.81, 134.63, 132.89, 131.16, 127.92, 127.76, 127.24, 125.16, 120.39, 120.05, 43.45; ESIMS m z 262 ([M−H]$^−$).

2-Chloro-N-(2-(3,3,3-trifluoropropyl)phenyl)acetamide (C37)

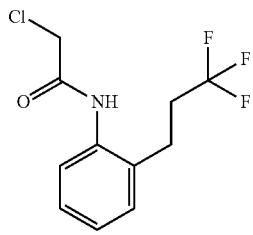 [SMILES: O=C(CCl)Nc1ccccc1CCC(F)(F)F]

The title compound was prepare from compound 27 and isolated as a peach solid (1.85 g, 85%): $^1$H NMR (400 MHz, CDCl$_3$) δ 8.19 (s, 1H), 7.71-7.62 (m, 1H), 7.35-7.28 (m, 1H), 7.26-7.21 (m, 2H), 4.25 (s, 2H), 2.95-2.70 (m, 2H), 2.52-2.26 (m, 2H); $^{19}$F NMR (376 MHz, CDCl$_3$) δ −66.74; ESIMS m z 266 ([M+H]$^+$).

2-Chloro-N-(2-chloro-4,5-dimethylphenyl)acetamide (C38)

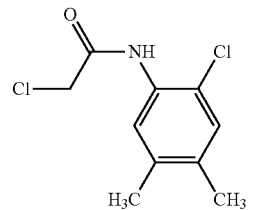

The title compound was prepared from commercial starting materials and isolated as a brown solid (2.77 g, 93%): mp 124-128° C.; $^1$H NMR (400 MHz, CDCl$_3$) δ 8.77 (s, 1H), 8.10 (s, 1H), 7.16 (s, 1H), 4.22 (s, 2H), 2.25 (s, 3H), 2.22 (s, 3H); $^{13}$C NMR (101 MHz, CDCl$_3$) δ 163.66, 136.42, 134.44, 131.01, 129.65, 122.41, 120.50, 43.13, 19.65, 19.21; EIMS m/z 232.

114

2-Chloro-N-(2-(methoxymethyl)phenyl)acetamide (C39)

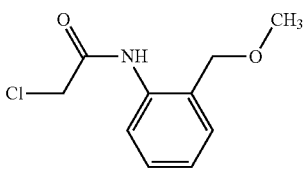

The title compound was prepared from compound C29 and isolated as an off-white solid (1.423 g, 99%): $^1$H NMR (400 MHz, CDCl$_3$) δ 9.87-9.67 (m, 1H), 8.24-8.14 (m, 1H), 7.36 (td, J=7.8, 1.7 Hz, 1H), 7.21 (dd, J=7.6, 1.7 Hz, 1H), 7.11 (td, J=7.5, 1.2 Hz, 1H), 4.53 (s, 2H), 4.21 (s, 2H), 3.45 (s, 3H); $^{13}$C NMR (126 MHz, CDCl$_3$) δ 164.33, 136.89, 129.26, 129.23, 126.86, 124.57, 121.66, 73.81, 58.14, 43.08; EIMS m z 213.

N-(2-(sec-Butyl)-5-methoxyphenyl)-2-chloroacetamide (C40)

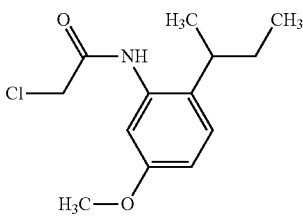 [SMILES: CCC(C)c1ccc(OC)cc1NC(=O)CCl]

The title compound was prepared from compound C31 and isolated as a brown oil (2.0 g, used without purification): $^1$H NMR (400 MHz, CDCl$_3$) δ 8.36 (s, 1H), 7.46 (d, J=2.8 Hz, 1H), 7.15 (d, J=8.8 Hz, 1H), 6.77 (dd, J=3.2, 5.6 Hz, 1H), 4.26 (s, 2H), 3.79 (s, 3H), 2.72-2.65 (m, 1H), 1.65-1.55 (m, 2H), 1.25 (dd, J=2.4, 6.8 Hz, 3H), 0.87 (t, J=7.2 Hz, 3H); ESIMS m z 256 ([M+H]$^+$).

2-Chloro-N-(5-chloro-2-(trifluoromethoxy)phenyl)acetamide (C41)

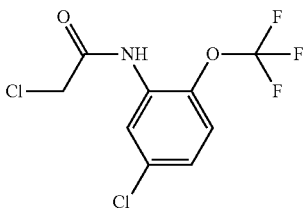 [SMILES: O=C(CCl)Nc1cc(Cl)ccc1OC(F)(F)F]

The title compound was prepared from commercially available starting materials and isolated as a light pink solid (4.3 g, 96%): mp 72-74° C.; $^1$H NMR (400 MHz, CDCl$_3$) δ 8.74 (s, 1H), 8.50 (d, J=2.5 Hz, 1H), 7.23 (dq, J=8.8, 1.5 Hz, 1H), 7.15 (dd, J=8.8, 2.5 Hz, 1H), 4.23 (s, 2H); $^{19}$F NMR (376 MHz, CDCl$_3$) δ −58.01; ESIMS m z 288 ([M+H]$^+$).

2-Chloro-N-(5-chloro-2-(2,2,2-trifluoroethoxy)phenyl)acetamide (C42)

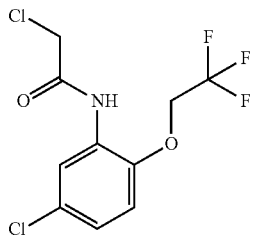 [SMILES: O=C(CCl)Nc1cc(Cl)ccc1OCC(F)(F)F]

The title compound was prepared from compound C33 and isolated as a tan solid (3.45 g, 97%): mp 116-118° C.; $^1$H NMR (400 MHz, CDCl$_3$) δ 8.97 (s, 1H), 8.46 (d, J=2.6 Hz, 1H), 7.09 (dd, J=8.7, 2.5 Hz, 1H), 6.82 (d, J=8.8 Hz, 1H), 4.43 (q, J=7.8 Hz, 2H), 4.21 (s, 2H); $^{19}$F NMR (376 MHz, CDCl$_3$) δ −74.09; ESIMS m z 302 ([M+H]$^+$).

2-Imino-3-(5,6,7,8-tetrahydronaphthalen-1-yl)thiazolidin-4-one (C43)

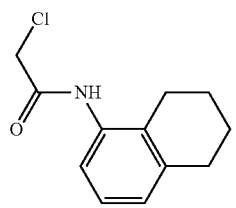 [SMILES: O=C(CCl)Nc1cccc2c1CCCC2]

The title compound was prepared from commercially available starting materials and isolated as a tan solid (1.91 g, 82%): mp 102-106° C.; $^1$H NMR (400 MHz, CDCl$_3$) δ 9.19 (s, 1H), 7.25-7.07 (m, 2H), 6.92 (dd, J=7.3, 1.7 Hz, 1H), 4.28-4.09 (m, 2H), 2.77 (d, J=5.5 Hz, 2H), 2.39 (q, J=5.5, 3.9 Hz, 2H), 1.69 (d, J=7.0 Hz, 4H); $^{13}$C NMR (101 MHz, CDCl$_3$) δ 131.14, 126.63, 125.92, 29.50, 24.21, 22.46, 22.36; ESIMS m z 247 ([M+H]$^+$).

Example 33: Preparation of 3-(2-butylphenyl)-2-iminothiazolidin-4-one (C44)

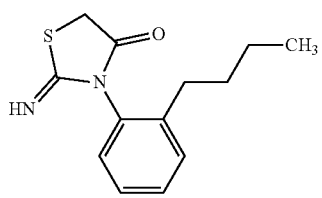 [SMILES: CCCCc1ccccc1N1C(=N)SCC1=O]

To a solution of N-(2-butylphenyl)-2-chloroacetamide (C34; 1.41 g, 6.3 mmol) in acetone (6.3 mL) was added potassium thiocyanate (1.22 g, 12.5 mmol) in portions. The reaction mixture was stirred at reflux for 5 h and at room temperature overnight. Cesium carbonate (0.102 g, 0.31 mmol) was added slowly, and the reaction mixture was stirred for 30 min. The solution was filtered through Celite® and the filtrate was concentrated. Purification by flash chromatography (0-60% ethyl acetate/hexanes) provided the title compound as a red oil (1.50 g, 96%): $^1$H NMR (400 MHz, CDCl$_3$) δ 7.44-7.37 (m, 2H), 7.37-7.30 (m, 1H), 7.10 (dd, J=7.5, 1.2 Hz, 1H), 4.08 (s, 2H), 2.50-2.31 (m, 2H), 1.58-1.48 (m, 2H), 1.38-1.28 (m, 2H), 0.90 (t, J=7.3 Hz, 3H); $^{13}$C NMR (101 MHz, CDCl$_3$) δ 171.58, 161.18, 141.58, 130.91, 130.59, 129.40, 127.94, 34.34, 32.41, 31.37, 31.18, 23.03, 14.27; ESIMS m z 249 ([M+H]$^+$).

The following compounds were prepared according to the procedure in Example 33.

3-(2-(2-Cyclopropylethyl)phenyl)-2-iminothiazolidin-4-one (C45)

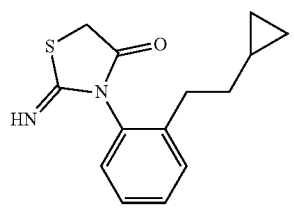 [SMILES: N=C1SCC(=O)N1c1ccccc1CCC1CC1]

The title compound was prepared from compound C35 and isolated as a brown solid (303 mg, 68%): $^1$H NMR (400 MHz, CDCl$_3$) δ 7.90 (s, 1H), 7.67 (d, J=7.9 Hz, 1H), 7.25-7.19 (m, 2H), 7.18 (dd, J=6.8, 2.0 Hz, 1H), 3.89 (d, J=3.2 Hz, 2H), 2.72 (t, J=7.5 Hz, 2H), 1.51 (q, J=7.3 Hz, 2H), 0.70 (tt, J=6.9, 3.0 Hz, 1H), 0.51-0.38 (m, 2H), 0.07 (dt, J=5.8, 2.9 Hz, 2H); $^{13}$C NMR (101 MHz, CDCl$_3$) δ 163.67, 135.15, 134.34, 130.36, 127.27, 127.08, 124.79, 111.46, 37.94, 35.73, 31.66, 11.09, 5.16; ESIMS m z 261 ([M+H]$^+$).

(E)-2-Imino-3-(2-(3,3,3-trifluoroprop-1-en-1-yl)phenyl)thiazolidin-4-one (C46)

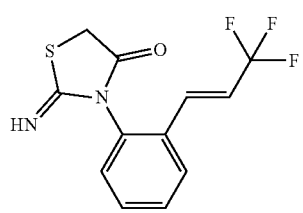 [SMILES: N=C1SCC(=O)N1c1ccccc1/C=C/C(F)(F)F]

The title compound was prepared from compound C36 and isolated as a red solid (795 mg, 89%): $^1$H NMR (400 MHz, CDCl$_3$) δ 7.94 (s, 1H), 7.69 (d, J=7.2 Hz, 1H), 7.60-7.42 (m, 2H), 7.26-7.22 (m, 1H), 6.96 (d, J=16.0 Hz, 1H), 6.28-6.11 (m, 1H), 4.12 (d, J=7.2 Hz, 2H); $^{19}$F NMR (376 MHz, CDCl$_3$) δ −63.82; ESIMS m z 287 ([M+H]$^+$).

2-Imino-3-(2-(3,3,3-trifluoropropyl)phenyl)thiazolidin-4-one (C47)

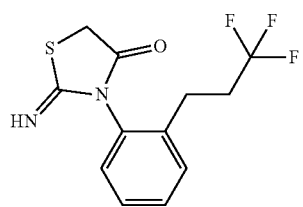 [SMILES: N=C1SCC(=O)N1c1ccccc1CCC(F)(F)F]

The title compound was prepared from intermediate C37 and isolated as a red solid (1.85 g, 88%): $^1$H NMR (400 MHz, CDCl$_3$) δ 7.90 (s, 1H), 7.57-7.31 (m, 3H), 7.16 (dd, J=7.7, 1.6 Hz, 1H), 4.10 (d, J=1.8 Hz, 2H), 2.76-2.60 (m, 2H), 2.43-2.22 (m, 2H); $^{19}$F NMR (376 MHz, CDCl$_3$) δ −67.08; $^{13}$C NMR (101 MHz, CDCl$_3$) δ 161.07, 137.88, 130.88, 130.67, 129.84, 128.99, 128.33, 125.58, 34.91, 34.63, 24.19; ESIMS m z 289 ([M+H]$^+$).

3-(2-Chloro-4,5-dimethylphenyl)-2-iminothiazolidin-4-one (C48)

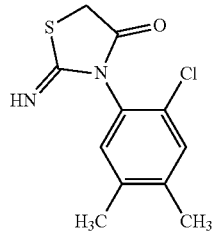 [SMILES: Cc1cc(Cl)c(N2C(=N)SCC2=O)cc1C]

The title compound was prepared from compound C38 and isolated as a brown oil (2.62 g, 82%): $^1$H NMR (400 MHz, DMSO-d$_6$) δ 9.28 (s, 1H), 7.39 (s, 1H), 7.15-7.12 (m, 1H), 4.25-4.14 (m, 2H), 2.25 (s, 3H), 2.22 (s, 3H); $^{13}$C NMR (101 MHz, DMSO-d$_6$) δ 170.99, 156.80, 139.50, 136.47, 131.52, 130.07, 130.01, 128.53, 33.63, 18.82, 18.62; ESIMS m z 255 ([M+H]$^+$).

2-Imino-3-(2-(methoxymethyl)phenyl)thiazolidin-4-one (C49)

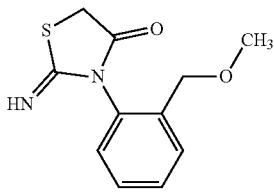 [SMILES: COCc1ccccc1N1C(=N)SCC1=O]

The title compound was prepared from compound C39 and isolated as a brown oil (1.88 g, 72%): $^1$H NMR (400 MHz, DMSO-d$_6$) δ 9.23 (s, 1H), 7.51-7.36 (m, 3H), 7.18 (dd, J=7.5, 1.5 Hz, 1H), 4.34-3.95 (m, 4H), 3.22 (s, 3H); $^{13}$C NMR (101 MHz, CDCl$_3$) δ 170.87, 160.31, 136.49, 129.91, 129.71, 129.24, 129.12, 71.07, 58.34, 33.98; ESIMS m z 237 ([M+H]$^+$).

3-(2-(sec-Butyl)-5-methoxyphenyl)-2-iminothiazolidin-4-one (C50)

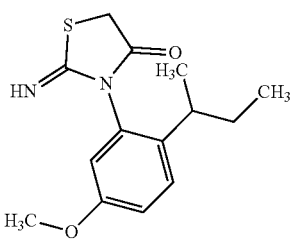 [SMILES: CCC(C)c1ccc(OC)cc1N1C(=N)SCC1=O]

The title compound was prepared from compound C40 and isolated as an off-white solid (0.5 g, 15%): mp 115-117° C.; $^1$H NMR (400 MHz, DMSO-d$_6$) δ 9.20 (d, J=5.2 Hz, 1H), 7.27 (d, J=8.4 Hz, 1H), 6.99 (dd, J=2.8, 8.8 Hz, 1H), 6.68 (d, J=2.0 Hz, 1H), 4.29-4.09 (m, 2H), 3.73 (s, 3H), 2.38-2.31 (m, 1H), 1.58-1.39 (m, 2H), 1.05 (dd, J=6.8, 10.8 Hz, 3H), 0.75-0.63 (m, 3H); ESIMS m z 279 ([M+H]$^+$).

3-(5-Chloro-2-(trifluoromethoxy)phenyl)-2-iminothiazolidin-4-one (C51)

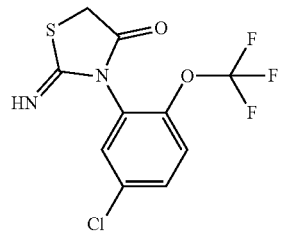 [SMILES: N=C1SCC(=O)N1c1cc(Cl)ccc1OC(F)(F)F]

The title compound was prepared from compound C41 and isolated as a light pink solid (2.49 g, 52%): mp 109-111° C.; $^1$H NMR (400 MHz, CDCl$_3$) δ 7.94 (s, 1H), 7.51-7.45 (m, 1H), 7.36 (q, J=3.4 Hz, 2H), 4.19-4.02 (m, 2H); $^{19}$F NMR (376 MHz, CDCl$_3$) δ −57.42; ESIMS m z 311 ([M+H]$^+$).

3-(5-Chloro-2-(2,2,2-trifluoroethoxy)phenyl)-2-iminothiazolidin-4-one (C52)

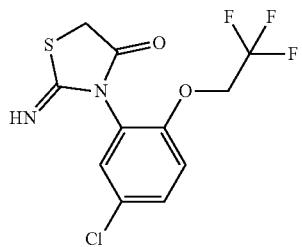 [SMILES: N=C1SCC(=O)N1c1cc(Cl)ccc1OCC(F)(F)F]

The title compound was prepared from compound C42 and isolated as a yellow solid (3.12 g, 92%): mp 114-116° C.; $^1$H NMR (400 MHz, CDCl$_3$) δ 7.84 (s, 1H), 7.43 (dd, J=9.0, 2.5 Hz, 1H), 7.29 (d, J=2.6 Hz, 1H), 7.00 (d, J=8.9 Hz, 1H), 4.39-0.310 (m, 2H), 4.07 (d, J=6.0 Hz, 2H); $^{19}$F NMR (376 MHz, CDCl$_3$) δ −74.16; ESIMS m/z 325 ([M+H]$^+$).

2-Imino-3-(5,6,7,8-tetrahydronaphthalen-1-yl)thiazolidin-4-one (C53)

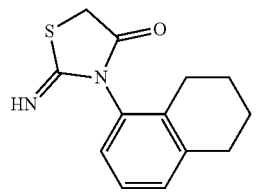 [SMILES: N=C1SCC(=O)N1c1cccc2c1CCCC2]

The title compound was prepared from compound C43 and isolated as a tan solid (1.91 g, 82%): mp 102-106° C.; $^1$H NMR (400 MHz, CDCl$_3$) δ 9.19 (s, 1H), 7.25-7.07 (m, 2H), 6.92 (dd, J=7.3, 1.7 Hz, 1H), 4.28-4.09 (m, 2H), 2.77 (d, J=5.5 Hz, 2H), 2.39 (q, J=5.5, 3.9 Hz, 2H), 1.69 (d, J=7.0 Hz, 4H); $^{13}$C NMR (101 MHz, CDCl$_3$) δ 131.14, 126.63, 125.92, 29.50, 24.21, 22.46, 22.36; ESIMS m/z 247 ([M+H]$^+$).

TABLE 2

Analytical Data for Compounds in Table 1

| Cmpd. No. | Melting Point (° C.) | MASS SPEC | NMR |
| --- | --- | --- | --- |
| A1 | | ESIMS m/z 624 ([M + H]$^+$) | $^1$H NMR (400 MHz, CDCl$_3$) δ 8.55 (s, 1H), 8.12-8.05 (m, 2H), 7.83-7.78 (m, 2H), 7.39 (dd, J = 8.8, 1.2 Hz, 2H), 7.31 (dd, J = 17.6, 8.1 Hz, 4H), 6.86 (s, 1H), 4.46-4.30 (m, 2H), 3.99 (d, J = 1.0 Hz, 2H), 3.02 (t, J = 7.3 Hz, 2H), 2.58 (p, J = 6.8 Hz, 1H), 2.34 (t, J = 0.7 Hz, 3H), 1.17 (dd, J = 13.5, 6.9 Hz, 6H); $^{19}$F NMR (376 MHz, CDCl$_3$) δ −58.03 |
| A2 | 154-155.5 | ESIMS m/z 610 ([M + H]$^+$) | $^1$H NMR (400 MHz, CDCl$_3$) δ 8.55 (s, 1H), 8.12-8.06 (m, 2H), 7.84-7.77 (m, 2H), 7.49-7.43 (m, 2H), 7.39 (dq, J = 8.9, 0.9 Hz, 2H), 7.34-7.27 (m, 3H), 7.06 (dt, J = 7.8, 1.0 Hz, 1H), 4.37 (ddt, J = 28.4, 10.8, 7.3 Hz, 2H), 4.00 (d, J = 1.0 Hz, 2H), 3.01 (t, J = 7.3 Hz, 2H), 2.68-2.60 (m, 1H), 1.19 (dd, J = 10.0, 6.9 Hz, 6H); $^{19}$F NMR (376 MHz, CDCl$_3$) δ −58.03 |
| A3 | | ESIMS m/z 596 ([M + H]$^+$) | $^1$H NMR (400 MHz, CDCl$_3$) δ 8.55 (s, 1H), 8.22-8.13 (m, 2H), 7.84-7.74 (m, 2H), 7.43-7.33 (m, 3H), 7.29-7.22 (m, 3H), 6.95-6.87 (m, 1H), 4.04 (t, J = 1.2 Hz, 2H), 2.64 (p, J = 6.9 Hz, 1H), 2.36 (s, 3H), 1.22 (dd, J = 26.5, 6.8 Hz, 6H); $^{19}$F NMR (376 MHz, CDCl$_3$) δ −58.03 |
| A4 | | ESIMS m/z 660 ([M + H]$^+$) | $^1$H NMR (400 MHz, CDCl$_3$) δ 8.59 (s, 1H), 8.22 (d, J = 8.1 Hz, 2H), 7.85-7.76 (m, 2H), 7.58 (d, J = 8.2 Hz, 2H), 7.41 (dd, J = 9.0, 1.0 Hz, 2H), 7.33 (d, J = 8.1 Hz, 1H), 7.28 (d, J = 1.9 Hz, 1H), 6.89-6.82 (m, 1H), 4.68 (q, J = 12.9 Hz, 1H), 4.55-4.44 (m, 1H), 3.98 (d, J = 0.6 Hz, 2H), 2.55 (p, J = 6.9 Hz, 1H), 2.34 (d, J = 0.7 Hz, 3H), 1.15 (dd, J = 11.2, 6.9 Hz, 6H); $^{19}$F NMR (376 MHz, CDCl$_3$) δ −58.02, −104.24, −104.31 |
| A5 | | ESIMS m/z 612 ([M + H]$^+$) | $^1$H NMR (400 MHz, CDCl$_3$) δ 8.57 (s, 1H), 8.04-7.97 (m, 2H), 7.85-7.76 (m, 2H), 7.43-7.33 (m, 3H), 7.10 (dd, J = 7.8, 1.7 Hz, 1H), 7.05-6.89 (m, 4H), 4.43 (t, J = 6.4 Hz, 2H), 4.00-3.74 (m, 4H), 2.88 (t, J = 6.3 Hz, 2H), 1.20 (t, J = 7.0 Hz, 3H); $^{19}$F NMR (376 MHz, CDCl$_3$) δ −58.02 |
| A6 | 183-185 | ESIMS m/z 624 ([M + H]$^+$) | $^1$H NMR (500 MHz, CDCl$_3$) δ 8.55 (d, J = 1.3 Hz, 1H), 8.10 (d, J = 7.7 Hz, 2H), 7.84-7.74 (m, 2H), 7.46-7.35 (m, 4H), 7.35-7.27 (m, 3H), 7.09 (d, J = 7.9 Hz, 1H), 4.38 (q, J = 7.0 Hz, 2H), 3.99 (s, 2H), 3.02 (t, J = 7.5 Hz, 2H), 2.41 (t, J = 8.0 Hz, 2H), 1.31 (q, J = 7.4 Hz, 4H), 0.87 (t, J = 7.3 Hz, 3H); $^{19}$F NMR (471 MHz, CDCl$_3$) δ −58.03 |
| A7 | 172-175 | ESIMS m/z 636 ([M + H]$^+$) | $^1$H NMR (500 MHz, CDCl$_3$) δ 8.55 (s, 1H), 8.10 (d, J = 7.8 Hz, 2H), 7.82-7.75 (m, 2H), 7.48-7.27 (m, 7H), 7.09 (d, J = 7.7 Hz, 1H), 4.38 (q, J = 7.6 Hz, 2H), 4.00 (d, J = 2.0 Hz, 2H), 3.02 (t, J = 7.5 Hz, 2H), 2.52 (t, J = 7.9 Hz, 2H), 1.45 (q, J = 7.5 Hz, 2H), 0.74-0.60 (m, 1H), 0.39 (d, J = 7.8 Hz, 2H), −0.03 (d, J = 4.9 Hz, 2H); $^{19}$F NMR (471 MHz, CDCl$_3$) δ −58.03 |
| A8 | 177-183 | ESIMS m/z 664 ([M + H]$^+$) | $^1$H NMR (500 MHz, CDCl$_3$) δ 8.55 (d, J = 1.4 Hz, 1H), 8.14-8.06 (m, 2H), 7.85-7.74 (m, 2H), 7.46 (t, J = 7.6 Hz, 1H), 7.43-7.34 (m, |

TABLE 2-continued

Analytical Data for Compounds in Table 1

| Cmpd. No. | Melting Point (° C.) | MASS SPEC | NMR |
|---|---|---|---|
| | | | 4H), 7.30 (d, J = 7.9 Hz, 2H), 7.14 (d, J = 7.8 Hz, 1H), 4.39 (dtd, J = 18.3, 10.9, 7.6 Hz, 2H), 4.01 (d, J = 1.6 Hz, 2H), 3.03 (t, J = 7.5 Hz, 2H), 2.66 (t, J = 8.5 Hz, 2H), 2.46-2.31 (m, 2H); $^{19}$F NMR (471 MHz, CDCl$_3$) δ −58.03, −67.06 |
| A9 | 218-221 | ESIMS m/z 662 ([M + H]$^+$) | $^1$H NMR (500 MHz, CDCl$_3$) δ 8.55 (s, 1H), 8.14-8.06 (m, 2H), 7.85-7.76 (m, 2H), 7.71-7.60 (m, 1H), 7.53 (td, J = 9.3, 7.8, 4.8 Hz, 2H), 7.39 (d, J = 8.5 Hz, 2H), 7.30 (d, J = 7.9 Hz, 2H), 7.22 (d, J = 7.4 Hz, 1H), 6.91 (d, J = 16.0 Hz, 1H), 6.25-6.15 (m, 1H), 4.45-4.31 (m, 2H), 4.07-3.97 (m, 2H), 3.03 (t, J = 7.5 Hz, 2H); $^{19}$F NMR (471 MHz, CDCl$_3$) δ −58.03, −63.83 |
| A10 | 116-120, 148-151 | ESIMS m/z 612 ([M + H]$^+$) | $^1$H NMR (400 MHz, CDCl$_3$) δ 8.55 (s, 1H), 8.13-8.05 (m, 2H), 7.83-7.72 (m, 2H), 7.42-7.34 (m, 2H), 7.30 (d, J = 8.2 Hz, 2H), 7.04-6.98 (m, 1H), 6.85 (s, 2H), 4.39 (t, J = 7.5 Hz, 2H), 3.97 (d, J = 0.8 Hz, 2H), 3.81 (s, 3H), 3.04 (t, J = 7.5 Hz, 2H), 2.12 (s, 3H); $^{19}$F NMR (376 MHz, CDCl$_3$) δ −58.03 |
| A11 | 199-200.5 | ESIMS m/z 600 ([M + H]$^+$) | $^1$H NMR (500 MHz, CDCl$_3$) δ 8.55 (d, J = 1.4 Hz, 1H), 8.11 (dd, J = 8.1, 1.5 Hz, 2H), 7.80 (dd, J = 8.8, 1.6 Hz, 2H), 7.39 (d, J = 8.5 Hz, 2H), 7.31 (d, J = 7.8 Hz, 2H), 7.23 (d, J = 5.6 Hz, 1H), 7.12 (t, J = 9.0 Hz, 1H), 7.05 (d, J = 6.8 Hz, 1H), 4.40 (t, J = 7.5 Hz, 2H), 4.08-3.91 (m, 2H), 3.05 (t, J = 7.5 Hz, 2H), 2.36 (s, 3H); $^{19}$F NMR (471 MHz, CDCl$_3$) δ −58.03, −124.88 |
| A12 | 222-228 | ESIMS m/z 617 ([M + H]$^+$) | $^1$H NMR (500 MHz, CDCl$_3$) δ 8.55 (d, J = 1.4 Hz, 1H), 8.14-8.05 (m, 2H), 7.83-7.75 (m, 2H), 7.40 (dd, J = 16.9, 8.4 Hz, 3H), 7.30 (d, J = 7.9 Hz, 2H), 7.23 (d, J = 8.3 Hz, 1H), 7.08 (s, 1H), 4.40 (t, J = 7.5 Hz, 2H), 4.00 (q, J = 18.1 Hz, 2H), 3.05 (t, J = 7.5 Hz, 2H), 2.37 (s, 3H); $^{19}$F NMR (471 MHz, CDCl$_3$) δ −58.03 |
| A13 | 98-105 | ESIMS m/z 612 ([M + H]$^+$) | $^1$H NMR (500 MHz, CDCl$_3$) δ 8.55 (d, J = 1.2 Hz, 1H), 8.15-8.05 (m, 2H), 7.84-7.77 (m, 2H), 7.39 (d, J = 8.5 Hz, 2H), 7.30 (d, J = 7.8 Hz, 2H), 7.21 (d, J = 8.5 Hz, 1H), 6.96 (s, 1H), 6.92 (d, J = 8.4 Hz, 1H), 4.38 (t, J = 7.5 Hz, 2H), 4.03-3.89 (m, 2H), 3.76 (d, J = 1.3 Hz, 3H), 3.04 (t, J = 7.6 Hz, 2H), 2.31 (s, 3H); $^{19}$F NMR (471 MHz, CDCl$_3$) δ −58.03 |
| A14 | 243-249 | ESIMS m/z 650 ([M + H]$^+$) | $^1$H NMR (500 MHz, CDCl$_3$) δ 8.55 (s, 1H), 8.10 (d, J = 7.8 Hz, 2H), 7.82-7.77 (m, 2H), 7.69 (d, J = 8.1 Hz, 1H), 7.40 (t, J = 8.9 Hz, 3H), 7.29 (d, J = 7.8 Hz, 2H), 7.10 (s, 1H), 4.39 (q, J = 7.2, 6.7 Hz, 2H), 4.06-3.90 (m, 2H), 3.04 (t, J = 7.5 Hz, 2H), 2.46 (s, 3H); $^{19}$F NMR (471 MHz, CDCl$_3$) δ −58.03, −61.12 |
| A15 | 193-199 | ESIMS m/z 624 ([M + H]$^+$) | $^1$H NMR (500 MHz, CDCl$_3$) δ 8.55 (s, 1H), 8.10 (d, J = 7.8 Hz, 2H), 7.79 (d, J = 8.5 Hz, 2H), 7.39 (d, J = 8.5 Hz, 2H), 7.29 (d, J = 7.9 Hz, 2H), 7.25-7.16 (m, 2H), 6.89 (s, 1H), 4.38 (q, J = 7.9 Hz, 2H), 3.98 (d, J = 2.6 Hz, 2H), 3.03 (t, J = 7.5 Hz, 2H), 2.35-2.32 (m, 5H), 1.61-1.55 (m, 2H), 0.90 (t, J = 7.4 Hz, 3H); $^{19}$F NMR (471 MHz, CDCl$_3$) δ −58.03 |
| A16 | 195-197 | ESIMS m/z 626 ([M + H]$^+$) | $^1$H NMR (500 MHz, CDCl$_3$) δ 8.55 (s, 1H), 8.09 (d, J = 7.8 Hz, 2H), 7.84-7.75 (m, 2H), 7.38 (d, J = 8.5 Hz, 2H), 7.30 (d, J = 7.9 Hz, 2H), 7.18 (d, J = 8.5 Hz, 1H), 6.97 (s, 1H), 6.90 (d, J = 8.4 Hz, 1H), 4.39 (td, J = 7.7, 3.3 Hz, 2H), 4.01 (qd, J = 7.8, 7.3, 3.0 Hz, 2H), 3.95 (d, J = 7.7 Hz, 2H), 3.04 (t, J = 7.5 Hz, 2H), 2.31 (s, 3H), 1.25 (t, J = 7.0 Hz, 3H); $^{19}$F NMR (471 MHz, CDCl$_3$) δ −58.03 |

TABLE 2-continued

Analytical Data for Compounds in Table 1

| Cmpd. No. | Melting Point (° C.) | MASS SPEC | NMR |
|---|---|---|---|
| A17 | | ESIMS m/z 642 ([M + H]+) | $^1$H NMR (400 MHz, CDCl$_3$) δ 8.56 (s, 1H), 8.09 (d, J = 8.2 Hz, 2H), 7.82-7.76 (m, 2H), 7.39 (d, J = 8.4 Hz, 2H), 7.29 (d, J = 8.2 Hz, 2H), 7.06 (d, J = 10.7 Hz, 1H), 6.89 (d, J = 7.1 Hz, 1H), 4.39 (ddt, J = 30.3, 10.8, 7.3 Hz, 2H), 3.98 (d, J = 1.1 Hz, 2H), 3.03 (t, J = 7.3 Hz, 2H), 2.63-2.46 (m, 1H), 2.27-2.19 (m, 3H), 1.21-1.11 (m, 6H); $^{19}$F NMR (376 MHz, CDCl$_3$) δ −58.03, −114.48 |
| A18 | 194-198 | ESIMS m/z 631 ([M + H]+) | $^1$H NMR (500 MHz, CDCl$_3$) δ 8.54 (s, 1H), 8.14-8.07 (m, 2H), 7.83-7.75 (m, 2H), 7.39 (d, J = 8.5 Hz, 2H), 7.33-7.28 (m, 3H), 7.02 (s, 1H), 4.40 (t, J = 7.6 Hz, 2H), 3.99 (q, J = 18.1 Hz, 2H), 3.04 (t, J = 7.6 Hz, 2H), 2.26 (s, 3H), 2.25 (s, 3H); $^{19}$F NMR (471 MHz, CDCl$_3$) δ −58.03 |
| A19 | 206-210 | ESIMS m/z 638 ([M + H]+) | $^1$H NMR (300 MHz, CDCl$_3$) δ 8.56 (d, J = 0.5 Hz, 1H), 8.07 (t, J = 8.5 Hz, 2H), 7.83-7.76 (m, 2H), 7.39 (d, J = 8.5 Hz, 2H), 7.33-7.24 (m, 4H), 6.87 (d, J = 9.5 Hz, 1H), 5.17-5.00 (m, 1H), 4.00-3.89 (m, 2H), 3.06 (ddd, J = 29.0, 13.6, 6.7 Hz, 1H), 2.86-2.70 (m, 1H), 2.64-2.50 (m, 1H), 2.35 (d, J = 6.8 Hz, 3H), 1.30-1.11 (m, 9H); $^{13}$C NMR (126 MHz, CDCl$_3$) δ 172.57, 163.43, 143.01, 142.91, 141.46, 139.37, 139.29, 136.88, 135.58, 131.89, 131.41, 131.37, 129.80, 129.75, 128.63, 128.58, 128.25, 126.84, 126.61, 126.56, 122.40, 121.18, 121.16, 74.25, 42.06, 33.01, 28.44, 23.84, 23.56, 23.52, 20.84; $^{19}$F NMR (471 MHz, CDCl$_3$) δ −58.03 |
| A20 | | HRMS-ESI (m/z) [M + H]+ calcd for C$_{31}$H$_{28}$F$_4$N$_5$O$_4$S, 641.172; found, 642.1805 | $^1$H NMR (400 MHz, CDCl$_3$) δ 8.57 (s, 1H), 8.20 (d, J = 8.0 Hz, 2H), 7.86-7.74 (m, 2H), 7.50-7.37 (m, 4H), 7.37-7.27 (m, 2H), 6.90-6.82 (m, 1H), 5.86-5.67 (m, 1H), 4.61-4.29 (m, 2H), 4.06-3.93 (m, 2H), 2.59 (m, 1H), 2.34 (d, J = 1.8 Hz, 3H), 1.18 (m, 6H); $^{19}$F NMR (376 MHz, CDCl$_3$) δ −58.02, −185.29 |
| A21 | | HRMS-ESI (m/z) [M + H]+ calcd for C$_{30}$H$_{23}$F$_7$N$_5$O$_5$S, 697.123; found, 698.1315 | $^1$H NMR (400 MHz, CDCl$_3$) δ 8.57 (s, 1H), 8.21 (d, J = 8.1 Hz, 2H), 7.86-7.76 (m, 2H), 7.52-7.35 (m, 3H), 7.06 (d, J = 2.0 Hz, 1H), 6.95 (dd, J = 8.5, 1.4 Hz, 1H), 5.89-5.64 (m, 1H), 4.55-4.39 (m, 2H), 4.34 (qd, J = 8.1, 6.3 Hz, 2H), 4.13-4.04 (m, 1H), 4.04-3.90 (m, 2H), 2.42-2.29 (m, 4H); $^{19}$F NMR (376 MHz, CDCl$_3$) δ −58.03, −74.30, −185.34 |
| A22 | | HRMS-ESI (m/z) [M + H]+ calcd for C$_{29}$H$_{20}$ClF$_7$N$_5$O$_5$S, 717.0684; found, 718.0757 | $^1$H NMR (400 MHz, CDCl$_3$) δ 8.57 (s, 1H), 8.22 (d, J = 8.1 Hz, 2H), 7.88-7.74 (m, 2H), 7.52-7.37 (m, 4H), 7.28 (d, J = 2.5 Hz, 1H), 7.00 (dd, J = 8.9, 1.0 Hz, 1H), 5.76 (ddd, J = 48.7, 7.9, 4.4 Hz, 1H), 4.59-4.43 (m, 2H), 4.43-4.26 (m, 3H), 4.07-3.89 (m, 2H); $^{19}$F NMR (376 MHz, CDCl$_3$) δ −58.02, −74.18, −185.30 |
| A23 | | HRMS-ESI (m/z) [M + H]+ calcd for C$_{30}$H$_{25}$ClF$_4$N$_5$O$_4$S, 661.1174; found, 662.1251 | $^1$H NMR (400 MHz, CDCl$_3$) δ 8.57 (s, 1H), 8.21 (d, J = 8.0 Hz, 2H), 7.87-7.76 (m, 2H), 7.50-7.35 (m, 5H), 7.09 (d, J = 2.1 Hz, 1H), 5.86-5.65 (m, 1H), 4.63-4.29 (m, 3H), 4.02 (t, J = 0.9 Hz, 2H), 2.61 (dtd, J = 9.6, 6.9, 3.5 Hz, 1H), 1.18 (ddd, J = 13.9, 6.9, 2.2 Hz, 6H); $^{19}$F NMR (376 MHz, CDCl$_3$) δ −58.02, −185.31 |
| A24 | | ESIMS m/z 678 ([M + H]+) | $^1$H NMR (400 MHz, CDCl$_3$) δ 8.58 (s, 1H), 8.20 (d, J = 8.0 Hz, 2H), 7.84-7.78 (m, 2H), 7.48-7.38 (m, 6H), 7.32 (ddt, J = 5.8, 4.7, 3.1 Hz, 1H), 7.07 (dd, J = 7.7, 1.0 Hz, 1H), 5.74 (ddd, J = 48.6, 8.1, 2.9 Hz, 1H), 4.58-4.25 (m, 2H), 4.02 (t, J = 1.1 Hz, 2H), 2.70-2.58 (m, 1H), 1.25-1.17 (m, 6H); $^{19}$F NMR (376 MHz, CDCl$_3$) δ −85.89, −87.85, −185.35, −185.61 |

TABLE 2-continued

Analytical Data for Compounds in Table 1

| Cmpd. No. | Melting Point (° C.) | MASS SPEC | NMR |
|---|---|---|---|
| A25 | | ESIMS m/z 712 ([M]⁺) | ¹H NMR (400 MHz, CDCl₃) δ 8.58 (s, 1H), 8.21 (d, J = 8.0 Hz, 2H), 7.85-7.77 (m, 2H), 7.48-7.36 (m, 6H), 7.09 (d, J = 2.2 Hz, 1H), 5.89-5.64 (m, 1H), 4.62-4.29 (m, 2H), 4.02 (d, J = 1.0 Hz, 2H), 2.68-2.53 (m, 1H), 1.18 (ddd, J = 13.9, 6.8, 2.2 Hz, 6H); ¹⁹F NMR (376 MHz, CDCl₃) δ −85.89, −87.85, −185.32, −185.54 |
| A26 | | ESIMS m/z 692 ([M + H]⁺) | ¹H NMR (400 MHz, CDCl₃) δ 8.58 (s, 1H), 8.21 (d, J = 7.9 Hz, 2H), 7.81 (d, J = 9.0 Hz, 2H), 7.43 (dd, J = 17.5, 8.5 Hz, 4H), 7.34 (d, J = 8.0 Hz, 1H), 7.28-7.26 (m, 1H), 6.87 (s, 1H), 5.82-5.67 (m, 1H), 4.47 (m, 2H), 4.01 (s, 2H), 2.60 (m, 1H), 2.35 (s, 3H), 1.18 (ddd, J = 15.0, 6.8, 2.2 Hz, 6H); ¹⁹F NMR (376 MHz, CDCl₃) δ −85.89, −87.84 |
| A27 | | ESIMS m/z 612 ([M + H]⁺) | ¹H NMR (400 MHz, CDCl₃) δ 8.57 (s, 1H), 8.01 (d, J = 8.3 Hz, 2H), 7.81 (dd, J = 9.3, 2.6 Hz, 2H), 7.47-7.37 (m, 5H), 7.08 (d, J = 7.6 Hz, 1H), 6.96 (d, J = 8.2 Hz, 2H), 4.50-4.31 (m, 2H), 4.30-4.09 (m, 2H), 3.86 (d, J = 1.0 Hz, 2H), 3.19 (s, 3H), 2.86 (t, J = 6.5 Hz, 2H); ¹⁹F NMR (376 MHz, CDCl₃) δ −58.03 |
| A28 | | ESIMS m/z 654 ([M + H]⁺) | ¹H NMR (400 MHz, CDCl₃) δ 8.55 (d, J = 0.7 Hz, 1H), 8.09 (d, J = 8.1 Hz, 2H), 7.80 (d, J = 8.9 Hz, 2H), 7.39 (d, J = 8.6 Hz, 2H), 7.31-7.27 (m, 3H), 7.01 (dd, J = 8.7, 2.7 Hz, 1H), 6.58 (dd, J = 4.5, 2.7 Hz, 1H), 4.49-4.28 (m, 2H), 4.01-3.95 (m, 2H), 3.78 (s, 3H), 3.02 (td, J = 7.3, 2.9 Hz, 2H), 2.25 (p, J = 7.1 Hz, 1H), 1.54 (m, 2H), 1.13 (dd, J = 17.1, 6.8 Hz, 3H), 0.72 (dt, J = 9.0, 7.4 Hz, 3H); ¹⁹F NMR (376 MHz, CDCl₃) δ −58.03 |
| A29 | 221-223 | ESIMS m/z 686 ([M + H]⁺) | ¹H NMR (400 MHz, CDCl₃) δ 8.55 (s, 1H), 8.11 (d, J = 8.2 Hz, 2H), 7.82-7.77 (m, 2H), 7.50 (dd, J = 8.9, 2.5 Hz, 1H), 7.39 (dd, J = 8.7, 1.2 Hz, 3H), 7.36-7.28 (m, 3H), 4.41 (t, J = 7.4 Hz, 2H), 4.07-3.89 (m, 2H), 3.05 (t, J = 7.4 Hz, 2H); ¹⁹F NMR (376 MHz, CDCl₃) δ −57.30, −58.03 |
| A30 | 195-197 | ESIMS m/z 700 ([M + H]⁺) | ¹H NMR (400 MHz, CDCl₃) δ 8.55 (s, 1H), 8.14-8.03 (m, 2H), 7.84-7.73 (m, 2H), 7.48-7.35 (m, 4H), 7.35-7.28 (m, 2H), 6.98 (d, J = 8.9 Hz, 1H), 4.41 (td, J = 7.2, 2.9 Hz, 2H), 4.36-4.29 (m, 2H), 3.97 (d, J = 3.8 Hz, 2H), 3.05 (t, J = 7.4 Hz, 2H); ¹⁹F NMR (376 MHz, CDCl₃) δ −58.03, −74.15 |
| A31 | | ESIMS m/z 680 ([M + H]⁺) | ¹H NMR (400 MHz, CDCl₃) δ 8.55 (s, 1H), 8.13-8.02 (m, 2H), 7.84-7.75 (m, 2H), 7.42-7.35 (m, 2H), 7.30 (d, J = 8.2 Hz, 2H), 7.24-7.19 (m, 1H), 7.06-7.01 (m, 1H), 6.94 (d, J = 8.5 Hz, 1H), 4.35 (dq, J = 33.5, 7.7 Hz, 4H), 4.03-3.85 (m, 2H), 3.04 (t, J = 7.5 Hz, 2H), 2.34 (s, 3H); ¹⁹F NMR (376 MHz, CDCl₃) δ −58.03, −74.26 |
| A32 | | ESIMS m/z 610 ([M + H]⁺) | ¹H NMR (400 MHz, CDCl₃) δ 8.55 (s, 1H), 8.12-8.07 (m, 2H), 7.82-7.75 (m, 2H), 7.41-7.36 (m, 2H), 7.30 (m, 3H), 7.23-7.13 (m, 2H), 4.40-4.32 (m, 2H), 4.00 (s, 2H), 3.02 (t, J = 7.5 Hz, 2H), 2.42 (q, J = 7.5 Hz, 2H), 2.12 (s, 3H), 1.17 (t, J = 7.6 Hz, 3H); ¹⁹F NMR (376 MHz, CDCl₃) δ −58.03 |
| A33 | 203-210 | ESIMS m/z 622 ([M + H]⁺) | ¹H NMR (400 MHz, CDCl₃) δ 8.55 (s, 1H), 8.13-8.06 (m, 2H), 7.84-7.76 (m, 2H), 7.39 (d, J = 8.6 Hz, 2H), 7.30 (d, J = 8.2 Hz, 2H), 7.25-7.14 (m, 2H), 6.97-6.85 (m, 1H), 4.38 (t, J = 7.5 Hz, 2H), 4.00-3.93 (m, 2H), 3.04 (t, J = 7.5 Hz, 2H), 2.82 (s, 2H), 2.50-2.36 (m, 2H), 1.81-1.72 (m, 4H); ¹⁹F NMR (376 MHz, CDCl₃) δ −58.03 |
| A34 | | ESIMS m/z 628 ([M + H]⁺) | ¹H NMR (400 MHz, CDCl₃) δ 8.57 (s, 1H), 8.20 (d, J = 8.1 Hz, 2H), 7.82-7.78 (m, 2H), |

TABLE 2-continued

Analytical Data for Compounds in Table 1

| Cmpd. No. | Melting Point (° C.) | MASS SPEC | NMR |
|---|---|---|---|
| | | | 7.49-7.38 (m, 7H), 7.07 (d, J = 7.9 Hz, 1H), 5.73 (dd, J = 48.3, 8.5 Hz, 1H), 4.62-4.24 (m, 2H), 4.02 (t, J = 1.1 Hz, 2H), 2.65 (td, J = 6.9, 2.9 Hz, 1H), 1.27-1.15 (m, 6H); $^{19}$F NMR (376 MHz, CDCl$_3$) δ −58.03, −185.35, −185.60 |
| A35 | 132-136 | ESIMS m/z 654 ([M + H]$^+$) | $^1$H NMR (400 MHz, CDCl$_3$) δ 8.55 (s, 1H), 8.11-8.06 (m, 2H), 7.82-7.76 (m, 2H), 7.39 (d, J = 8.6 Hz, 2H), 7.30 (d, J = 8.1 Hz, 2H), 7.20-7.15 (m, 1H), 6.97 (d, J = 2.2 Hz, 1H), 6.89 (d, J = 8.3 Hz, 1H), 4.45-4.25 (m, 3H), 3.94 (d, J = 2.2 Hz, 2H), 3.07-2.99 (m, 2H), 2.30 (s, 3H), 1.67-1.55 (m, 2H), 1.18 (dd, J = 25.1, 6.1 Hz, 3H), 0.86 (dt, J = 11.1, 7.4 Hz, 3H); $^{19}$F NMR (376 MHz, CDCl$_3$) δ −58.03 |
| A36 | | ESIMS m/z 704 ([M + H]$^+$) | $^1$H NMR (400 MHz, CDCl$_3$) δ 8.57 (s, 1H), 8.22 (d, J = 8.0 Hz, 2H), 7.84-7.76 (m, 2H), 7.51 (dd, J = 8.9, 2.6 Hz, 1H), 7.47 (d, J = 8.2 Hz, 2H), 7.42-7.37 (m, 3H), 7.37-7.34 (m, 1H), 5.78 (ddd, J = 48.7, 8.3, 2.7 Hz, 1H), 4.62-4.31 (m, 2H), 4.09-3.92 (m, 2H); $^{19}$F NMR (376 MHz, CDCl$_3$) δ −57.31, −58.03, −185.16, −185.28 |
| A37 | | ESIMS m/z 630 ([M + H]$^+$) | $^1$H NMR (400 MHz, CDCl$_3$) δ 8.57 (s, 1H), 8.21 (d, J = 8.1 Hz, 2H), 7.80 (d, J = 9.1 Hz, 2H), 7.46 (d, J = 8.1 Hz, 2H), 7.40 (d, J = 8.6 Hz, 2H), 7.04 (d, J = 8.1 Hz, 1H), 6.86 (s, 2H), 5.77 (dd, J = 48.2, 8.9 Hz, 1H), 4.58-4.30 (m, 2H), 4.00 (s, 2H), 3.83 (s, 3H), 2.14 (s, 3H); $^{19}$F NMR (376 MHz, CDCl$_3$) δ −58.02, −185.15, −185.24 |
| A38 | 167-172 | ESIMS m/z 648 ([M + H]$^+$) | $^1$H NMR (400 MHz, CDCl$_3$) δ 8.57 (s, 1H), 8.21 (d, J = 8.0 Hz, 2H), 7.82-7.77 (m, 2H), 7.47 (d, J = 8.0 Hz, 2H), 7.40 (d, J = 8.6 Hz, 2H), 7.32 (s, 1H), 7.04 (s, 1H), 5.88-5.68 (m, 1H), 4.60-4.30 (m, 2H), 4.08-3.92 (m, 2H), 2.28 (s, 3H), 2.27 (s, 3H); $^{19}$F NMR (376 MHz, CDCl$_3$) δ −58.02, −185.09, −185.20 |
| A39 | | ESIMS m/z 640 ([M + H]$^+$) | $^1$H NMR (400 MHz, CDCl$_3$) δ 8.57 (s, 1H), 8.21 (d, J = 8.1 Hz, 2H), 7.83-7.78 (m, 2H), 7.46 (d, J = 7.9 Hz, 2H), 7.43-7.37 (m, 2H), 7.25-7.17 (m, 2H), 6.94 (d, J = 7.2 Hz, 1H), 5.77 (dd, J = 48.7, 8.4 Hz, 1H), 4.56-4.29 (m, 2H), 4.07-3.79 (m, 2H), 2.83 (s, 2H), 2.63-2.36 (m, 2H), 1.79 (s, 4H); $^{19}$F NMR (376 MHz, CDCl$_3$) δ −58.03, −185.15, −185.19 |
| A40 | | ESIMS m/z 630 ([M + H]$^+$) | $^1$H NMR (400 MHz, CDCl$_3$) δ 8.58 (s, 1H), 8.13 (d, J = 8.1 Hz, 2H), 7.83-7.77 (m, 2H), 7.40 (d, J = 8.3 Hz, 3H), 7.25-7.19 (m, 2H), 7.14 (dd, J = 23.5, 7.7 Hz, 1H), 7.06-6.88 (m, 2H), 5.60 (d, J = 47.5 Hz, 1H), 4.51 (dt, J = 21.5, 11.7 Hz, 2H), 4.43-3.88 (m, 4H), 1.27 (dt, J = 29.3, 7.0 Hz, 3H); $^{19}$F NMR (376 MHz, CDCl$_3$) δ −58.02, −186.52, −186.79 |
| A41 | | ESIMS m/z 672 ([M + H]$^+$) | $^1$H NMR (400 MHz, CDCl$_3$) δ 8.57 (s, 1H), 8.21 (d, J = 8.0 Hz, 2H), 7.83-7.75 (m, 2H), 7.48-7.42 (m, 2H), 7.39 (dq, J = 7.9, 1.1 Hz, 2H), 7.22-7.12 (m, 1H), 6.98 (d, J = 2.2 Hz, 1H), 6.94-6.86 (m, 1H), 5.86-5.61 (m, 1H), 4.58-4.22 (m, 3H), 3.96 (d, J = 2.1 Hz, 2H), 2.34-2.24 (m, 3H), 1.72-1.48 (m, 2H), 1.29-1.10 (m, 3H), 0.96-0.81 (m, 3H); $^{19}$F NMR (376 MHz, CDCl$_3$) δ −58.02, −185.33, −185.50 |
| A42 | 213-215 | ESIMS m/z 628 ([M + H]$^+$) | $^1$H NMR (400 MHz, CDCl$_3$) δ 8.57 (s, 1H), 8.21 (d, J = 8.0 Hz, 2H), 7.83-7.77 (m, 2H), 7.44 (d, J = 8.2 Hz, 2H), 7.40 (d, J = 8.5 Hz, 2H), 7.34 (t, J = 7.6 Hz, 1H), 7.24-7.16 (m, |

TABLE 2-continued

Analytical Data for Compounds in Table 1

| Cmpd. No. | Melting Point (° C.) | MASS SPEC | NMR |
|---|---|---|---|
| | | | 2H), 5.75 (dd, J = 47.2, 7.3 Hz, 1H), 4.61-4.28 (m, 2H), 4.02 (s, 2H), 3.51 (s, 3H), 2.42 (t, J = 7.6 Hz, 2H), 2.13 (s, 3H), 1.18 (td, J = 7.6, 2.0 Hz, 3H); $^{19}$F NMR (376 MHz, CDCl$_3$) δ −58.03, −185.25, −185.28 |
| A43 | | ESIMS m/z 695 ([M + H]$^+$) | $^1$H NMR (400 MHz, CDCl$_3$) δ 8.56 (s, 1H), 8.10 (d, J = 8.2 Hz, 2H), 7.81 (d, J = 9.0 Hz, 2H), 7.43-7.36 (m, 4H), 7.30 (d, J = 8.2 Hz, 2H), 7.08 (d, J = 2.1 Hz, 1H), 4.48-4.30 (m, 2H), 3.99 (s, 2H), 3.03 (t, J = 7.2 Hz, 2H), 2.67-2.52 (m, 1H), 1.17 (dd, J = 11.2, 6.8 Hz, 6H); $^{19}$F NMR (376 MHz, CDCl$_3$) δ −85.89, −87.84 |
| A44 | | ESIMS m/z 674 ([M + H]$^+$) | $^1$H NMR (400 MHz, CDCl$_3$) δ 8.56 (s, 1H), 8.09 (d, J = 8.2 Hz, 2H), 7.83-7.75 (m, 2H), 7.40 (d, J = 8.8 Hz, 2H), 7.35-7.27 (m, 4H), 6.86 (s, 1H), 4.48-4.27 (m, 2H), 3.99 (d, J = 1.0 Hz, 2H), 3.02 (t, J = 7.3 Hz, 2H), 2.58 (p, J = 6.8 Hz, 1H), 2.34 (s, 3H), 1.17 (dd, J = 13.5, 6.9 Hz, 6H); $^{19}$F NMR (376 MHz, CDCl$_3$) δ −85.89, −87.84 |
| A45 | | ESIMS m/z 660 ([M + H]$^+$) | $^1$H NMR (400 MHz, CDCl$_3$) δ 8.56 (s, 1H), 8.11-8.06 (m, 2H), 7.83-7.78 (m, 2H), 7.46 (dd, J = 4.1, 1.1 Hz, 2H), 7.39 (d, J = 8.9 Hz, 2H), 7.34-7.27 (m, 3H), 7.06 (d, J = 7.8 Hz, 1H), 4.47-4.27 (m, 2H), 4.00 (d, J = 1.0 Hz, 2H), 3.01 (t, J = 7.3 Hz, 2H), 2.64 (p, J = 6.8 Hz, 1H), 1.19 (dd, J = 10.0, 6.9 Hz, 6H); $^{19}$F NMR (376 MHz, CDCl$_3$) δ −85.89, −87.84 |
| A46 | | ESIMS m/z 659 ([M + H]$^+$) | $^1$H NMR (400 MHz, CDCl$_3$) δ 8.56 (d, J = 1.5 Hz, 1H), 8.19-8.12 (m, 2H), 7.82-7.75 (m, 2H), 7.48 (dd, J = 8.5, 2.3 Hz, 2H), 7.39 (d, J = 8.5 Hz, 2H), 7.31 (d, J = 8.0 Hz, 1H), 7.24 (s, 1H), 6.85 (s, 1H), 5.15 (t, J = 6.7 Hz, 1H), 4.70-4.38 (m, 2H), 4.05-3.91 (m, 2H), 2.55 (tt, J = 13.5, 6.8 Hz, 1H), 2.32 (d, J = 1.6 Hz, 3H), 1.21-1.06 (m, 6H); $^{19}$F NMR (376 MHz, CDCl$_3$) δ −58.02 |
| A47 | | ESIMS m/z 644 ([M + H]$^+$) | $^1$H NMR (400 MHz, CDCl$_3$) δ 8.57 (d, J = 1.4 Hz, 1H), 8.19-8.13 (m, 2H), 7.83-7.77 (m, 2H), 7.51-7.42 (m, 5H), 7.40 (d, J = 8.6 Hz, 2H), 7.04 (dd, J = 7.7, 3.4 Hz, 1H), 5.15 (t, J = 7.0 Hz, 1H), 4.69-4.40 (m, 2H), 4.05-3.96 (m, 2H), 2.60 (dt, J = 10.6, 6.8 Hz, 1H), 1.17 (ddd, J = 8.9, 6.8, 3.1 Hz, 6H); $^{19}$F NMR (376 MHz, CDCl$_3$) δ −58.02 |
| A48 | | ESIMS m/z 678 ([M + H]$^+$) | $^1$H NMR (400 MHz, CDCl$_3$) δ 8.57 (s, 1H), 8.17 (d, J = 8.1 Hz, 2H), 7.80 (d, J = 8.9 Hz, 2H), 7.52-7.46 (m, 2H), 7.38 (dd, J = 13.8, 8.6 Hz, 4H), 7.07 (t, J = 2.1 Hz, 1H), 5.16 (t, J = 6.9 Hz, 1H), 4.75-4.40 (m, 2H), 4.00 (d, J = 2.7 Hz, 2H), 2.56 (dt, J = 12.7, 6.5 Hz, 1H), 1.23-1.02 (m, 6H); $^{19}$F NMR (376 MHz, CDCl$_3$) δ −58.03 |
| A49 | | ESIMS m/z 668 ([M + H]$^+$) | $^1$H NMR (400 MHz, CDCl$_3$) δ 8.56 (s, 1H), 8.08 (td, J = 6.0, 2.9 Hz, 2H), 7.85-7.75 (m, 2H), 7.39 (d, J = 8.6 Hz, 2H), 7.31-7.27 (m, 2H), 7.18 (d, J = 8.6 Hz, 1H), 6.97 (d, J = 7.2 Hz, 1H), 6.89 (dd, J = 8.5, 4.1 Hz, 1H), 5.20-5.02 (m, 1H), 4.29 (q, J = 5.4 Hz, 1H), 3.92 (d, J = 2.1 Hz, 2H), 3.10 (tt, J = 13.7, 6.6 Hz, 1H), 2.76 (dq, J = 13.6, 6.7 Hz, 1H), 2.31 (d, J = 6.3 Hz, 3H), 1.55 (m, 2H), 1.30-1.09 (m, 6H), 0.95-0.76 (m, 3H); $^{19}$F NMR (376 MHz, CDCl$_3$) δ −58.03 |
| A50 | | ESIMS m/z 624 ([M + H]$^+$) | $^1$H NMR (400 MHz, CDCl$_3$) δ 8.55 (d, J = 1.9 Hz, 1H), 8.07 (t, J = 8.7 Hz, 2H), 7.84-7.74 (m, 2H), 7.46 (d, J = 4.2 Hz, 2H), 7.39 (d, J = 8.6 Hz, 2H), 7.36-7.25 (m, 3H), 7.06 (dd, J = 10.4, 7.9 Hz, 1H), 5.08 (qd, J = 6.2, 3.1 Hz, 1H), 4.06-3.91 (m, 2H), 3.05 (ddd, J = 33.0, 13.5, 6.5 Hz, 1H), 2.85-2.72 (m, 1H), 2.63 |

TABLE 2-continued

Analytical Data for Compounds in Table 1

| Cmpd. No. | Melting Point (° C.) | MASS SPEC | NMR |
|---|---|---|---|
| | | | (dp, J = 13.5, 6.8 Hz, 1H), 1.33-1.07 (m, 9H); $^{19}$F NMR (376 MHz, CDCl$_3$) δ −58.02 |
| A51 | | ESIMS m/z 626 ([M + H]$^+$) | $^1$H NMR (400 MHz, CDCl$_3$) δ 8.57 (s, 1H), 8.00 (t, J = 7.1 Hz, 2H), 7.83-7.77 (m, 2H), 7.40 (d, J = 8.5 Hz, 3H), 7.18-6.87 (m, 5H), 5.16 (q, J = 6.2 Hz, 1H), 3.99 (dt, J = 33.0, 7.9 Hz, 2H), 3.83 (d, J = 5.8 Hz, 2H), 2.85-2.66 (m, 2H), 1.32-1.13 (m, 6H); $^{19}$F NMR (376 MHz, CDCl$_3$) δ −58.03 |
| A52 | | ESIMS m/z 624 ([M + H]$^+$) | $^1$H NMR (400 MHz, CDCl$_3$) δ 8.56 (s, 1H), 8.07 (dd, J = 8.1, 3.2 Hz, 2H), 7.84-7.75 (m, 2H), 7.39 (d, J = 8.7 Hz, 2H), 7.33 (td, J = 7.6, 1.6 Hz, 1H), 7.28-7.24 (m, 2H), 7.24-7.13 (m, 2H), 5.09 (ddd, J = 11.6, 7.1, 3.8 Hz, 1H), 3.97 (d, J = 1.7 Hz, 2H), 3.06 (ddd, J = 13.6, 9.6, 6.6 Hz, 1H), 2.78 (ddd, J = 13.3, 7.0, 4.0 Hz, 1H), 2.41 (p, J = 7.4 Hz, 2H), 2.12 (d, J = 2.0 Hz, 3H), 1.27 (t, J = 5.9 Hz, 3H), 1.17 (t, J = 7.6 Hz, 3H); $^{19}$F NMR (376 MHz, CDCl$_3$) δ −58.03 |
| A53 | | ESIMS m/z 608 ([M + H]$^+$) | $^1$H NMR (400 MHz, CDCl$_3$) δ 8.55 (s, 1H), 8.10-8.04 (m, 2H), 7.83-7.75 (m, 2H), 7.40-7.35 (m, 2H), 7.34-7.24 (m, 4H), 6.98 (s, 1H), 6.85 (d, J = 4.8 Hz, 1H), 6.68 (d, J = 4.8 Hz, 1H), 4.35 (ddt, J = 38.0, 10.8, 7.6 Hz, 2H), 3.03 (t, J = 7.5 Hz, 2H), 2.58 (p, J = 6.9 Hz, 1H), 2.34 (s, 3H), 1.21 (d, J = 6.8 Hz, 3H), 1.10 (d, J = 6.9 Hz, 3H); $^{19}$F NMR (376 MHz, CDCl$_3$) δ −58.03 |
| A54 | | ESIMS m/z 626 ([M + H]$^+$) | $^1$H NMR (400 MHz, CDCl$_3$) δ 8.57 (s, 1H), 8.21-8.15 (m, 2H), 7.82-7.76 (m, 2H), 7.46-7.37 (m, 4H), 7.34 (dd, J = 8.0, 3.2 Hz, 1H), 7.28 (s, 1H), 6.99 (d, J = 1.8 Hz, 1H), 6.88 (dd, J = 4.7, 0.9 Hz, 1H), 6.71 (dd, J = 4.7, 1.7 Hz, 1H), 5.78 (ddd, J = 48.9, 7.9, 3.5 Hz, 1H), 4.56-4.27 (m, 2H), 2.58 (td, J = 6.9, 3.3 Hz, 1H), 2.35 (d, J = 3.5 Hz, 3H), 1.21 (dd, J = 6.8, 2.3 Hz, 3H), 1.11 (dd, J = 6.9, 2.2 Hz, 3H); $^{19}$F NMR (376 MHz, CDCl$_3$) δ −58.02, −185.63, −186.28 |
| A55 | | ESIMS m/z 622 ([M + H]$^+$) | $^1$H NMR (400 MHz, CDCl$_3$) δ 8.55 (d, J = 3.1 Hz, 1H), 8.09-8.01 (m, 2H), 7.83-7.76 (m, 2H), 7.38 (d, J = 8.5 Hz, 2H), 7.33 (dd, J = 8.0, 5.1 Hz, 1H), 7.30-7.23 (m, 3H), 7.05-6.95 (m, 1H), 6.83 (dd, J = 4.8, 2.2 Hz, 1H), 6.66 (t, J = 5.1 Hz, 1H), 5.09 (q, J = 6.5 Hz, 1H), 3.12 (ddd, J = 40.5, 13.4, 6.0 Hz, 1H), 2.80-2.67 (m, 1H), 2.57 (dp, J = 13.8, 6.9 Hz, 1H), 2.34 (d, J = 7.5 Hz, 3H), 1.30-1.16 (m, 6H), 1.09 (dd, J = 15.1, 6.9 Hz, 3H); $^{19}$F NMR (376 MHz, CDCl$_3$) δ −58.03 |

Example: Bioassays

Insecticidal Test for Beet Armyworm (*Spodoptera exigua*, LAPHEG) ("BAW")

Bioassays on beet armyworm (BAW; *Spodoptera exigua*: Lepidoptera) are conducted using a 128-well diet tray assay. One to five second instar BAW larvae are placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays are covered with a clear self-adhesive cover, vented to allow gas exchange, and held at 25° C., 14:10 light-dark for five to seven days. Percent mortality is recorded for the larvae in each well; activity in the eight wells is then averaged. In the reporting of the results, the "BAW & CL Rating Table" was used.

Insecticidal Test for Cabbage Looper (*Trichloplusia ni*, TRIPNI) ("CL")

Bioassays on cabbage looper (CL; *Trichloplusia ni*: Lepidoptera) are conducted using a 128-well diet tray assay. One to five second instar CL larvae are placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays are covered with a clear self-adhesive cover, vented to allow gas exchange, and held at 25° C., 14:10 light-dark for five to seven days. Percent mortality is recorded for the larvae in each well; activity in the eight wells is then averaged. In the reporting of the results, the "BAW & CL Rating Table" was used.

Insecticidal Test for Yellow Fever Mosquito (*Aedes aegypti*, AEDSAE) ("YFM")

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water/acetone mixture is added to each well. A robot (Biomek® NXP Laboratory Automation Workstation) is programmed to dispense 15 µL aspirations from the master plate into an empty 96-well shallow plate ("daughter" plate). There are 6 reps ("daughter" plates) created per master. The created "daughter" plates are then immediately infested with YFM larvae.

The day before plates are to be treated, mosquito eggs are placed in Millipore water containing liver powder to begin hatching (4 g. into 400 mL). After the "daughter" plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. In the reporting of the results, the "YFM Rating Table" was used.

BAW & CL Rating Table

| % Control (or Mortality) | Rating |
|---|---|
| 50-100 | A |
| More than 0-Less than 50 | B |
| Not Tested | C |
| No activity noticed in this bioassay | D |

YFM Rating Table

| % Control (or Mortality) | Rating |
|---|---|
| 80-100 | A |
| More than 0-Less than 80 | B |
| Not Tested | C |
| No activity noticed in this bioassay | D |

| Cmpd No | BAW | CL | YFM |
|---|---|---|---|
| A1 | A | A | C |
| A2 | A | A | A |
| A3 | D | D | C |
| A4 | A | A | C |
| A5 | B | A | A |
| A6 | A | A | A |
| A7 | B | A | A |
| A8 | A | A | A |
| A9 | A | A | A |
| A10 | D | A | A |
| A11 | B | A | A |
| A12 | A | A | A |
| A13 | A | A | A |
| A14 | A | A | A |
| A15 | A | A | A |
| A16 | A | A | A |
| A17 | A | A | A |
| A18 | D | D | D |

-continued

| Cmpd No | BAW | CL | YFM |
|---|---|---|---|
| A19 | A | A | B |
| A20 | A | A | C |
| A21 | A | A | C |
| A22 | A | A | C |
| A23 | A | A | C |
| A24 | A | A | C |
| A25 | A | B | C |
| A26 | A* | B* | C |
| A27 | A | A | C |
| A28 | A | A | C |
| A29 | A | A | C |
| A30 | A | A | C |
| A31 | A | A | C |
| A32 | D | A | C |
| A33 | D | A | C |
| A34 | A | A | C |
| A35 | A | A | C |
| A36 | A | A | C |
| A37 | D | A | C |
| A38 | D | A | C |
| A39 | A | A | C |
| A40 | A | A | C |
| A41 | A | A | C |
| A42 | B | A | C |
| A43 | A | D | C |
| A44 | A | A | C |
| A45 | A | A | C |
| A46 | A | A | C |
| A47 | A | A | C |
| A48 | A | A | C |
| A49 | A | A | C |
| A50 | A | A | C |
| A51 | A | A | C |
| A52 | A | A | C |
| A53 | A | A | C |
| A54 | A | A | C |
| A55 | A | A | C |

*tested at 5 µg/cm²

We claim:

1. A molecule having the structure of Formula A:

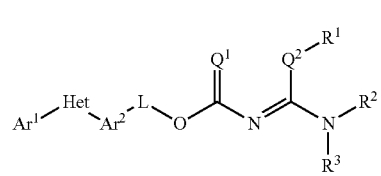

Formula A wherein:

(A) $Ar^1$ is phenyl or substituted phenyl wherein said substituted phenyl has one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n$($C_3$-$C_8$ cycloalkyl), $SS(=O)_n$($C_3$-$C_8$ halocycloalkyl), $S(=O)_n$ ($C_1$-$C_8$ alkyl), $S(=O)_n$($C_1$-$C_8$ haloalkyl), $OSO_2$($C_1$-$C_8$ alkyl), $OSO_2$($C_1$-$C_8$ haloalkyl), $C(=O)NR^xR^y$, ($C_1$-$C_8$ alkyl)$NR^xR^y$, $C(=O)C(=O)$($C_1$-$C_8$ alkyl), $C(=O)O$ ($C_1$-$C_8$ alkyl), $C(=O)$($C_1$-$C_8$ haloalkyl), $C(=O)O$($C_1$-$C_8$ haloalkyl), $C(=O)$($C_3$-$C_8$ cycloalkyl), $C(=O)O$ ($C_3$-$C_8$ cycloalkyl), $C(=O)$($C_2$-$C_8$ alkenyl), $C(=O)O$ ($C_2$-$C_8$ alkenyl), ($C_1$-$C_8$ alkyl)$O$($C_1$-$C_8$ alkyl), ($C_1$-$C_8$ alkyl)$S(=O)_n$($C_1$-$C_8$ alkyl), ($C_1$-$C_8$ alkyl)$OC(=O)$ ($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, or S(=O)$_n$NR$^x$R$^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O$C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(B) Het is triazolyl;

(C) Ar$^2$ is phenyl or substituted phenyl wherein said substituted phenyl has one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O$C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(D) L is linker selected from
(1) a bond,
(2) —CR$^4$R$^5$—CR$^6$R$^7$—, or
(3) —CR$^4$=CR$^6$—, wherein each of R$^4$, R$^5$, R$^6$, and R$^7$ is selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_1$-$C_8$ alkoxy, $C_1$-$C_8$ haloalkoxy, $C_2$-$C_8$ alkenyl, $C_2$-$C_8$ haloalkenyl, $C_2$-$C_8$ alkynyl, $C_2$-$C_8$ haloalkynyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_3$-$C_8$ cycloalkenyl, $C_3$-$C_8$ halocycloalkenyl, C(=O)($C_1$-$C_6$ alkyl), C(=O)O($C_1$-$C_6$ alkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S(=O)$_n$($C_1$-$C_6$ alkyl), C(=O)($C_1$-$C_6$ alkyl)C(=O)O($C_1$-$C_6$ alkyl), S(=O)$_n$($C_1$-$C_8$ alkyl), S(=O)$_n$($C_3$-$C_8$ cycloalkyl), S(=O)$_n$($C_1$-$C_8$ haloalkyl), S(=O)$_n$($C_3$-$C_8$ halocycloalkyl), phenyl, or phenoxy;

(E) R$^4$ and R$^6$ together can optionally form a 3- to 7-membered saturated or unsaturated ring which may contain C=O, C=S, N, S or O, and is optionally substituted with H, OH, F, Cl, Br, I, CN, NO$_2$, NR$_x$R$_y$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $C_3$-$C_6$ cycloalkynyl, S(=O)$_n$($C_1$-$C_6$ alkyl), S(=O)$_n$($C_1$-$C_6$ haloalkyl), OSO$_2$($C_1$-$C_6$ alkyl), OSO$_2$($C_1$-$C_6$ haloalkyl), C(=O)H, C(=O)OH, C(=O)NR$_x$R$_y$, ($C_1$-$C_6$ alkyl)NR$_x$R$_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S(=O)$_n$($C_1$-$C_6$ alkyl), C(=O)($C_1$-$C_6$ alkyl)C(=O)O($C_1$-$C_6$ alkyl), phenyl, phenoxy, and Het-1;

(F) Q$^1$ is selected from O or S;
(G) Q$^2$ is selected from O or S;
(H) R$^1$ is selected from (J), H, $C_1$-$C_8$ alkyl, $C_3$-$C_8$ cycloalkyl, $C_2$-$C_8$ alkenyl, $C_2$-$C_8$ alkynyl, C(=O)($C_1$-$C_8$ alkyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(=O)NR$^x$R$^y$, ($C_1$-$C_8$ alkyl)-C(=O)N(R$^x$)($C_1$-$C_8$ alkyl)-(Het-1), ($C_1$-$C_8$ alkyl)-C(=O)(Het-1), ($C_1$-$C_8$ alkyl)-C(=O)N(R$^x$)($C_1$-$C_8$ alkyl)N(R$^y$)C(=O)OH, (C$_1$-C$_8$ alkyl)-C(=O)N(R$^x$)(C$_1$-C$_8$ alkyl)N(R$^x$)(R$^y$), (C$_1$-C$_8$ alkyl)-C(=O)N(R$^x$)(C$_1$-C$_8$ alkyl)N(R$^y$)C(=O)O—(C$_1$-C$_8$ alkyl), (C$_1$-C$_8$ alkyl)-C(=O)N(R$^x$)(C$_1$-C$_8$ alkyl)N(R$^y$)C(=O)O—(C$_1$-C$_8$ alkyl)C(=O)OH, (C$_1$-C$_8$ alkyl)-C(=O)(Het-1)C(=O)O—(C$_1$-C$_8$ alkyl), (C$_1$-C$_8$ alkyl)-OC(=O)O—(C$_1$-C$_8$ alkyl), (C$_1$-C$_8$ alkyl)-OC(=O)—(C$_1$-C$_8$ alkyl), (C$_1$-C$_8$ alkyl)-OC(=O)—(C$_3$-C$_8$ cycloalkyl), (C$_1$-C$_8$ alkyl)-OC(=O)-(Het-1), (C$_1$-C$_8$ alkyl)-OC(=O)—(C$_1$-C$_8$ alkyl)N(R$^x$)C(=O)O—(C$_1$-C$_8$ alkyl), (C$_1$-C$_8$ alkyl)-NR$^x$R$^y$, (C$_1$-C$_8$ alkyl)-S-(Het-1), (C$_1$-C$_8$ alkyl)S(=O)$_n$(Het-1), or (C$_1$-C$_8$ alkyl)-O-(Het-1), wherein each alkyl, cycloalkyl, phenyl, and (Het-1) are optionally substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)H, C(=O)OH, C(=O)NR$^x$R$^y$, (C$_1$-C$_8$ alkyl)NR$^x$R$^y$, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, phenoxy, Si(C$_1$-C$_8$ alkyl)$_3$, S(=O)$_n$NR$^x$R$^y$, or (Het-1);

(I) R$^2$ is selected from (J), H, OH, SH, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)H, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, (C$_1$-C$_8$ alkyl)phenyl, (C$_1$-C$_8$ alkyl)-O-phenyl, C(=O)(Het-1), (Het-1), (C$_1$-C$_8$ alkyl)-(Het-1), (C$_1$-C$_8$ alkyl)-C(=O)—(C$_1$-C$_8$ alkyl), (C$_1$-C$_8$ alkyl)-OC(=O)—(C$_1$-C$_8$ alkyl), (C$_1$-C$_8$ alkyl)-O—C(=O)O—(C$_1$-C$_8$ alkyl), (C$_1$-C$_8$ alkyl)-O—C(=O)NR$^x$R$^y$, (C$_1$-C$_8$ alkyl)-C(=O)N(R$^x$)(C$_1$-C$_8$ alkyl)-(Het-1), (C$_1$-C$_8$ alkyl)-C(=O)(Het-1), (C$_1$-C$_8$ alkyl)-C(=O)N(R$^x$)(C$_1$-C$_8$ alkyl)N(R$^y$)C(=O)OH, (C$_1$-C$_8$ alkyl)-C(=O)N(R$^x$)(C$_1$-C$_8$ alkyl)N(R$^x$)(R$^y$), (C$_1$-C$_8$ alkyl)-C(=O)N(R$^x$)(C$_1$-C$_8$ alkyl)N(R$^y$)C(=O)O—(C$_1$-C$_8$ alkyl), (C$_1$-C$_8$ alkyl)-C(=O)N(R$^x$)(C$_1$-C$_8$ alkyl)N(R$^y$)C(=O)O—(C$_1$-C$_8$ alkyl)C(=O)OH, (C$_1$-C$_8$ alkyl)C(=O)(Het-1)C(=O)O—(C$_1$-C$_8$ alkyl), (C$_1$-C$_8$ alkyl)-OC(=O)O—

(C$_1$-C$_8$ alkyl), (C$_1$-C$_8$ alkyl)-OC(=O)—(C$_1$-C$_8$ alkyl), (C$_1$-C$_8$ alkyl)-OC(=O)—(C$_3$-C$_8$ cycloalkyl), (C$_1$-C$_8$ alkyl)-OC(=O)-(Het-1), (C$_1$-C$_8$ alkyl)-OC(=O)—(C$_1$-C$_8$ alkyl)N(R$^x$)C(=O)O—(C$_1$-C$_8$ alkyl), (C$_1$-C$_8$ alkyl)-NR$^x$R$^y$, (C$_1$-C$_8$ alkyl)-S-(Het-1), (C$_1$-C$_8$ alkyl)S(=O)$_n$(Het-1), or (C$_1$-C$_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, NO$_2$, oxo, thioxo, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)H, C(=O)OH, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, halophenyl, phenoxy, and (Het-1);

(J) R$^1$ and R$^2$ may be a 1- to 4-membered saturated or unsaturated, hydrocarbyl link, which may contain one or more heteroatoms selected from nitrogen, sulfur, and oxygen, and together with (Q$^2$)(C)(N) forms a 4- to 7-membered cyclic structure, wherein said hydrocarbyl link may optionally be substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)H, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, substituted phenyl, phenoxy, or (Het-1);

(K) R$^3$ is selected from C$_3$-C$_8$ cycloalkyl, phenyl, (C$_1$-C$_8$ alkyl)phenyl, (C$_1$-C$_8$ alkyl)-O-phenyl, (C$_2$-C$_8$ alkenyl)-O-phenyl, (Het-1), (C$_1$-C$_8$ alkyl)-(Het-1), (C$_1$-C$_8$ alkyl)-O-(Het-1), wherein the C$_3$-C$_8$ cycloalkyl, phenyl, (C$_1$-C$_8$ alkyl) phenyl, (C$_1$-C$_8$ alkyl)-O-phenyl, (C$_2$-C$_8$ alkenyl)-O-phenyl, (Het-1), (C$_1$-C$_8$ alkyl)-(Het-1), or (C$_1$-C$_8$ alkyl)-O-(Het-1) may be optionally substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)O(C$_1$-C$_8$ haloalkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, phenoxy, Si(C$_1$-C$_8$ alkyl)$_3$, S(=O)$_n$NR$^x$R$^y$, or (Het-1) or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, NO$_2$, NR$^x$R$^y$, C$_1$-C$_6$ alkyl, C$_1$-C$_6$ haloalkyl, C$_1$-C$_6$ alkoxy, C$_1$-C$_6$ haloalkoxy, S(=O)$_n$(C$_1$-C$_6$ alkyl), S(=O)$_n$(C$_1$-C$_6$ haloalkyl), phenyl, and oxo;

(L) R$^x$ and R$^y$ are independently selected from H, OH, SH, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)H, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, (C$_1$-C$_8$ alkyl)phenyl, (C$_1$-C$_8$ alkyl)-O-phenyl, C(=O)(Het-1), (Het-1), (C$_1$-C$_8$ alkyl)-(Het-1), (C$_1$-C$_8$ alkyl)-C(=O)—(C$_1$-C$_8$ alkyl), (C$_1$-C$_8$ alkyl)-OC(=O)—(C$_1$-C$_8$ alkyl), (C$_1$-C$_8$ alkyl)-O—C(=O)O—(C$_1$-C$_8$ alkyl), (C$_1$-C$_8$ alkyl)-C(=O)(Het-1), (C$_1$-C$_8$ alkyl)-C(=O)(Het-1)C(=O)O—(C$_1$-C$_8$ alkyl), (C$_1$-C$_8$ alkyl)-OC(=O)O—(C$_1$-C$_8$ alkyl), (C$_1$-C$_8$ alkyl)-OC(=O)—(C$_1$-C$_8$ alkyl), (C$_1$-C$_8$ alkyl)-OC(=O)—(C$_3$-C$_8$ cycloalkyl), (C$_1$-C$_8$ alkyl)-OC(=O)-(Het-1), (C$_1$-C$_8$ alkyl)-S-(Het-1), (C$_1$-C$_8$ alkyl)S(=O)$_n$(Het-1), or (C$_1$-C$_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, NO$_2$, oxo, thioxo, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)H, C(=O)OH, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, halophenyl, phenoxy, and (Het-1), or R$^x$ and R$^y$ together can optionally form a 5- to 7-membered saturated or unsaturated cyclic group which may contain one or more heteroatoms selected from nitrogen, sulfur, and oxygen, and where said cyclic group may be substituted with H, F, Cl, Br, I, CN, OH, SH, NO$_2$, oxo, thioxo, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, substituted phenyl, phenoxy, and (Het-1);

(M) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$(C$_3$-C$_8$ cycloalkyl), S(=O)$_n$(C$_3$-C$_8$ halocycloalkyl), S(=O)$_n$(C$_1$-C$_8$ alkyl), S(=O)$_n$(C$_1$-C$_8$ haloalkyl), OSO$_2$(C$_1$-C$_8$ alkyl), OSO$_2$(C$_1$-C$_8$ haloalkyl), C(=O)NR$^x$R$^y$, (C$_1$-C$_8$ alkyl)NR$^x$R$^y$, C(=O)(C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)O(C$_1$-C$_8$ haloalkyl), (C$_1$-C$_8$ alkyl)S(=O)$_n$(C$_1$-C$_8$ alkyl), (C$_1$-C$_8$ alkyl)OC(=O)(C$_1$-C$_8$ alkyl), (C$_1$-C$_8$ alkyl)OC(=O)O(C$_1$-C$_8$ alkyl), C(=O)(C$_1$-C$_8$ alkyl)C(=O)O(C$_1$-C$_8$ alkyl), (C$_1$-C$_8$ alkyl)C(=O)O(C$_1$-C$_8$ alkyl), (C$_1$-C$_8$ alkyl)C(=O)(C$_1$-C$_8$ alkyl), (C$_1$-C$_8$ alkyl)phenyl, (C$_1$-C$_8$ alkyl)-O-phenyl, phenyl, and phenoxy, wherein each alkyl, cycloalkyl, alkoxy, alkenyl, alkynyl, phenyl, and phenoxy may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)$H, $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $C_1$-$C_8$ alkyl)phenyl, $(C_1$-$C_8$ alkyl)-O-phenyl, phenyl, and phenoxy; and (N) n is each individually 0, 1, or 2.

2. The molecule of claim 1, having the structure of Formula One, Formula Two, or Formula Three:

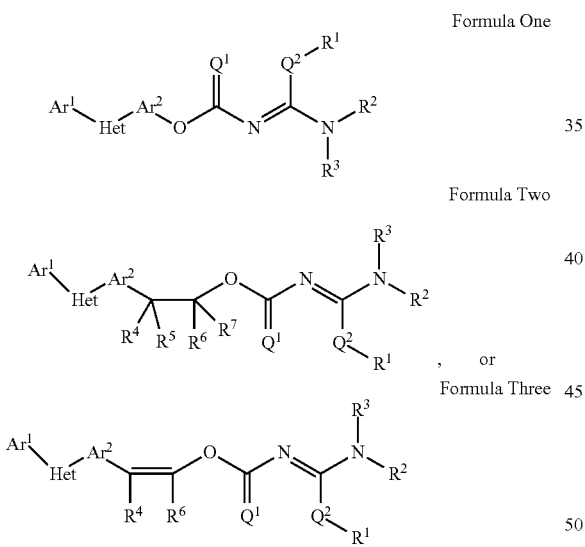

Formula One

Formula Two

, or

Formula Three wherein:
(A) $Ar^1$ is a phenyl or substituted phenyl having one or more substituents independently selected from $C_1$-$C_6$ alkyl, $C_1$-$C_6$ haloalkyl, $C_1$-$C_6$ alkoxy and $C_1$-$C_6$ haloalkoxy;
(B) Het is triazolyl;
(C) $Ar^2$ is a phenyl or a substituted phenyl having one or more substituents independently selected from F, Cl, Br, I, CN, $NO_2$, $NR^xR^y$, $C_1$-$C_6$ alkyl, $C_1$-$C_6$ alkoxy, and $C_1$-$C_6$ haloalkyl;
(D) Each $R^4$, $R^5$, $R^6$, and $R^7$ is selected from a H, F, Cl, Br, I, CN, oxo, $C_1$-$C_6$ alkyl, $C_2$-$C_6$ alkenyl, $C_2$-$C_6$ haloalkenyl, $C_2$-$C_6$ alkynyl, $C_1$-$C_6$ haloalkyl, $C_3$-$C_6$ cycloalkyl, $C_3$-$C_6$ cycloalkenyl, $C_3$-$C_6$ halocycloalkyl, and phenyl;

(E) $R^1$ is selected from (J), H, $C_1$-$C_6$ alkyl or $C_2$-$C_6$ alkenyl, wherein said alkyl or alkenyl is optionally substituted with a $C_3$-$C_6$ cycloalkyl or $C_1$-$C_6$ alkoxy;
(F) $R^2$ is selected from (J), H, OH, SH, $C_1$-$C_6$ alkyl or $C_2$-$C_6$ alkenyl, wherein said alkyl or alkenyl is optionally substituted with a $C_3$-$C_6$ cycloalkyl or $C_1$-$C_6$ alkoxy;
(G) $R^3$ is phenyl or (Het-1), wherein the phenyl or (Het-1) may be optionally substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $(C_1$-$C_6$ alkyl)$O(C_1$-$C_6$ alkyl), $(C_1$-$C_8$ alkyl)$O(C_1$-$C_8$ haloalkyl), $(C_1$-$C_6$ alkyl)$S(=O)_n(C_1$-$C_6$ alkyl), $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), and $S(=O)_n(C_1$-$C_6$ haloalkyl);
(H) $R^x$ and $R^y$ are independently selected from H, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, and phenyl;
(I) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo; and
(J) $R^1$ and $R^2$ may be a 1- to 4-membered saturated or unsaturated, hydrocarbyl link, which may contain one or more heteroatoms selected from nitrogen, sulfur, and oxygen, and together with $(Q^2)(C)(N)$ forms a 4- to 7-membered cyclic structure, wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo.

3. The molecule of claim 1, wherein $Ar^1$ is a substituted phenyl having one or more substituents independently selected from $OCF_3$, $OCF_2CF_3$, and $CF_3$.

4. The molecule of claim 1, wherein Het is 1,2,4-triazolyl.

5. The molecule of claim 1, wherein $Ar^2$ is a phenyl.

6. The molecule of claim 1, wherein $Ar^2$ is a substituted phenyl having one or more substituents independently selected from H, F, Cl, Br, I, CN, $C_1$-$C_6$ alkyl, and $C_1$-$C_6$ alkoxy.

7. The molecule of claim 1, wherein $R^1$ and $R^2$ together form a 5-membered ring containing one or two C=O, and such ring is optionally substituted with H, OH, F, Cl, Br, I, CN, $C_1$-$C_6$ alkyl, $C_1$-$C_6$ haloalkyl, $C_1$-$C_6$ alkoxy, $C_1$-$C_6$ haloalkoxy, phenyl or phenoxy.

8. The molecule of claim 1, wherein each of $R^4$, $R^5$, $R^6$, and $R^7$ is independently H, F, Cl, or a $C_1$-$C_6$ alkyl.

9. The molecule of claim 1, wherein $R^3$ is a substituted phenyl with one or more H, F, Cl, Br, I, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $(C_1$-$C_6$ alkyl)$O(C_1$-$C_6$ alkyl), $C_1$-$C_6$ alkoxy, $C_1$-$C_6$ haloalkoxy, or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), and $S(=O)_n(C_1$-$C_6$ haloalkyl).

10. A molecule that is a pesticidally acceptable acid addition salt, a salt derivative, a solvate, or an ester derivative, of a molecule according to claim 1.

11. A molecule according to claim 1 wherein at least one H is $^2$H or at least one C is $^{14}$C.

12. A composition comprising a molecule according to claim 1 and at least one other compound having insecticidal, herbicidal, acaricidal, nematicidal, or fungicidal activity.

13. A composition comprising a molecule according to claim 1 and a seed.

14. The molecule of claim 1 having a structure selected from compounds listed in Table 1

TABLE 1

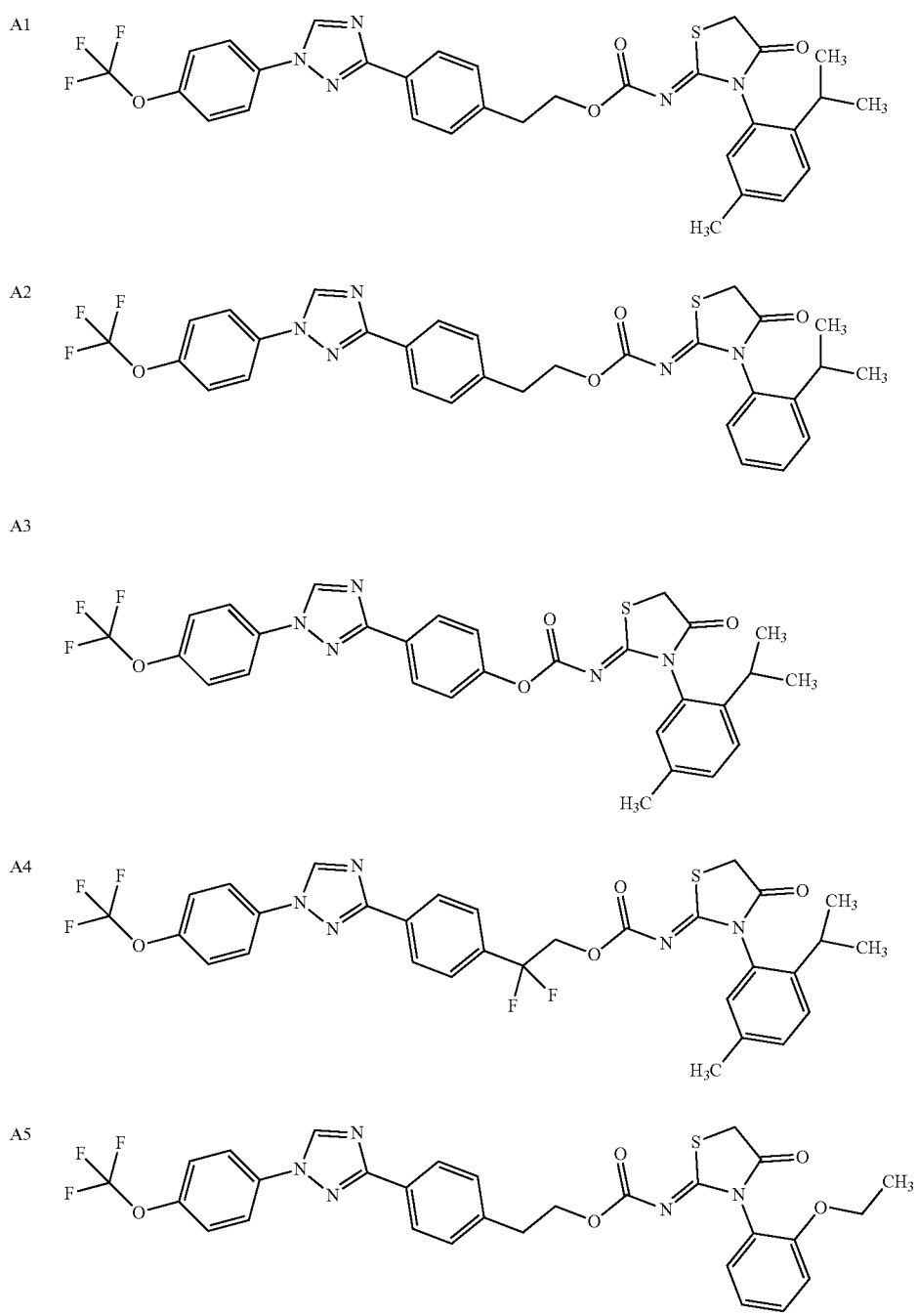

TABLE 1-continued
Structures for Compounds
A6 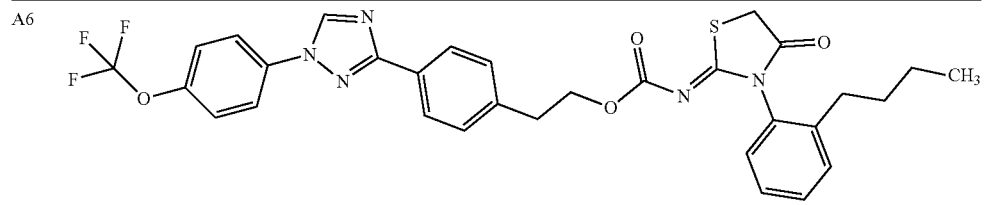
A7 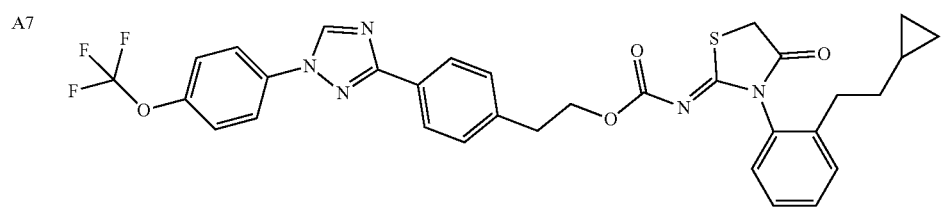
A8 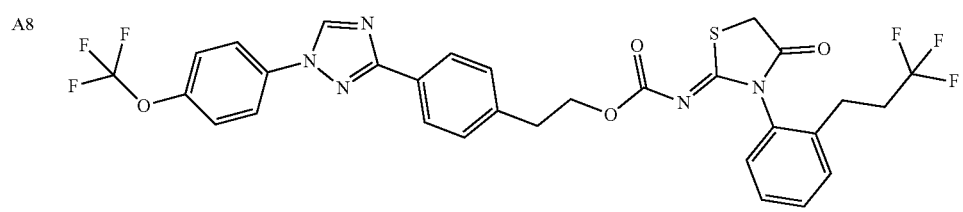
A9 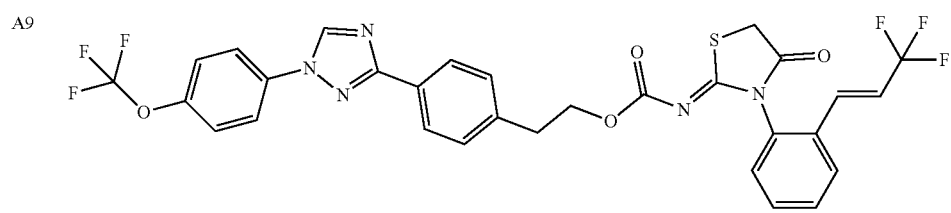
A10 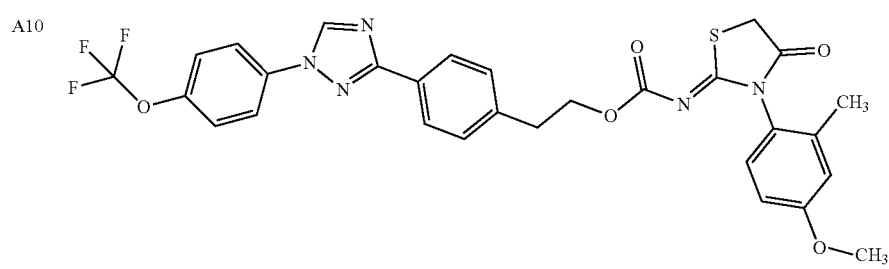
A11 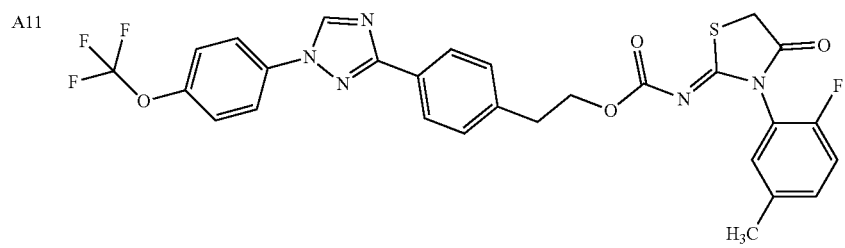
A12 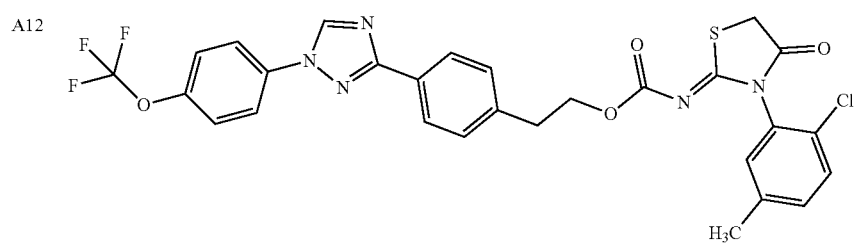

TABLE 1-continued
Structures for Compounds
A13
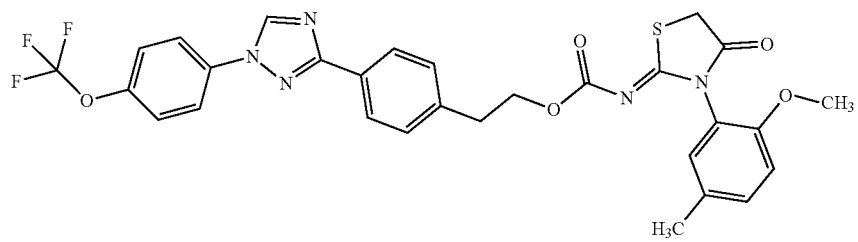 [SMILES: COc1ccc(C)cc1N1C(=O)CS/C1=N\C(=O)OCCc1ccc(-c2ncn(-c3ccc(OC(F)(F)F)cc3)n2)cc1]
A14
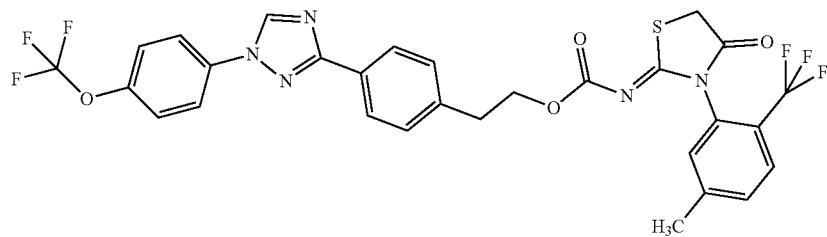 [SMILES: Cc1ccc(C(F)(F)F)c(N2C(=O)CS/C2=N\C(=O)OCCc2ccc(-c3ncn(-c4ccc(OC(F)(F)F)cc4)n3)cc2)c1]
A15
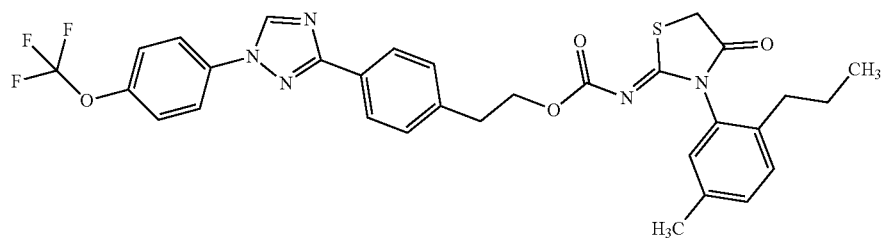
A16
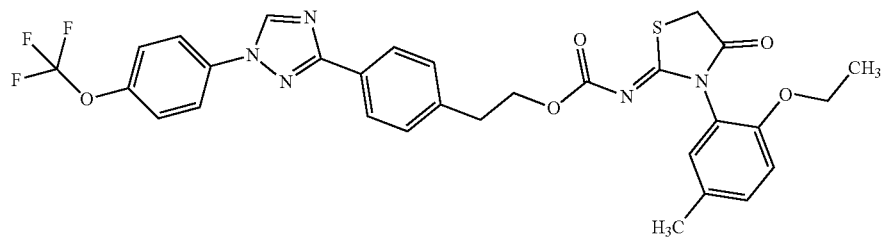 [SMILES: CCCc1ccc(C)cc1N1C(=O)CS/C1=N\C(=O)OCCc1ccc(-c2ncn(-c3ccc(OC(F)(F)F)cc3)n2)cc1]
A17
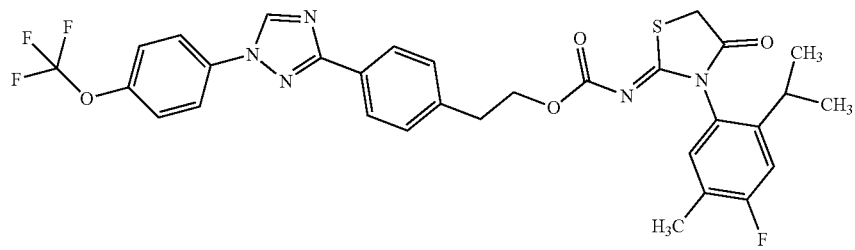 [SMILES: Cc1cc(N2C(=O)CS/C2=N\C(=O)OCCc2ccc(-c3ncn(-c4ccc(OC(F)(F)F)cc4)n3)cc2)c(C(C)C)cc1F]
A18
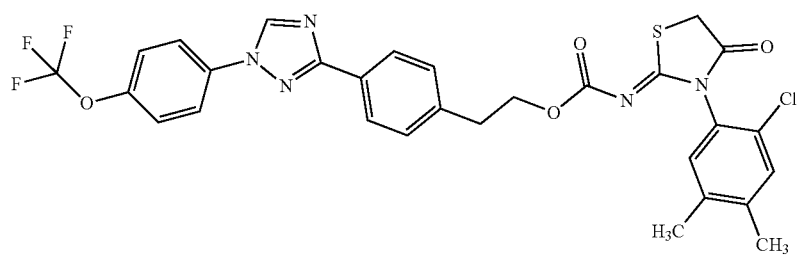

TABLE 1-continued
Structures for Compounds
A19
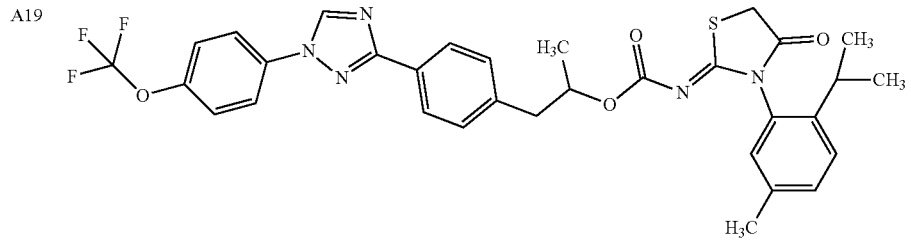
A20
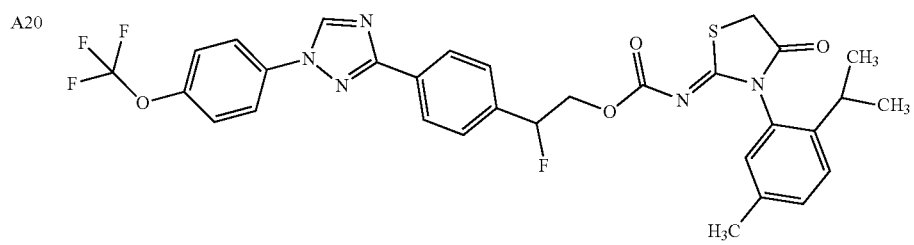
A21
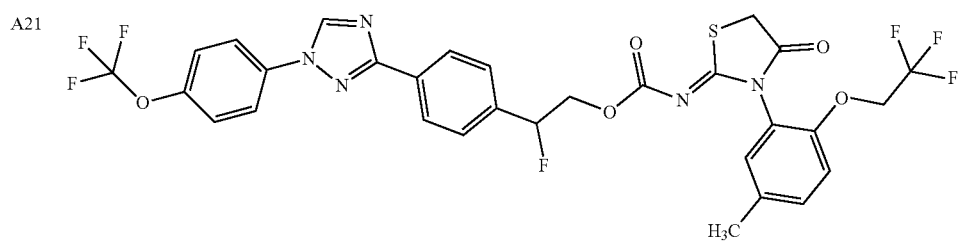
A22
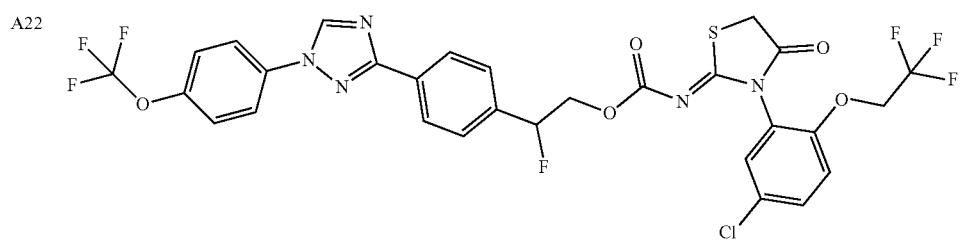
A23
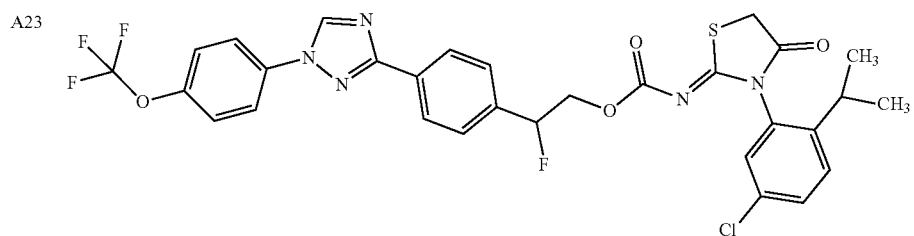
A24
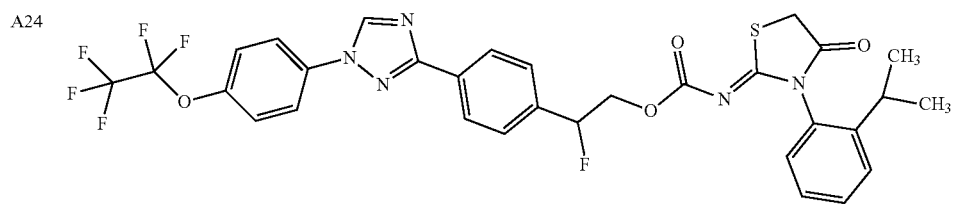

151 152
TABLE 1-continued
Structures for Compounds
A25
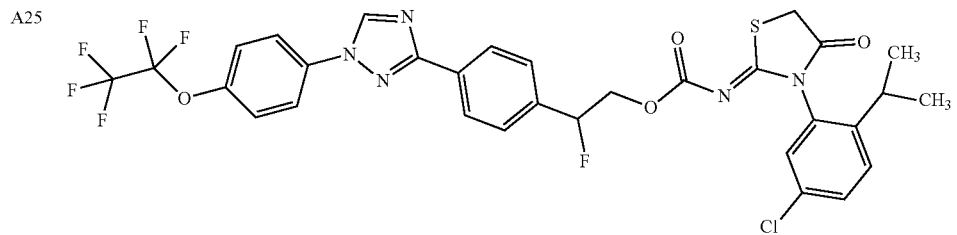
A26
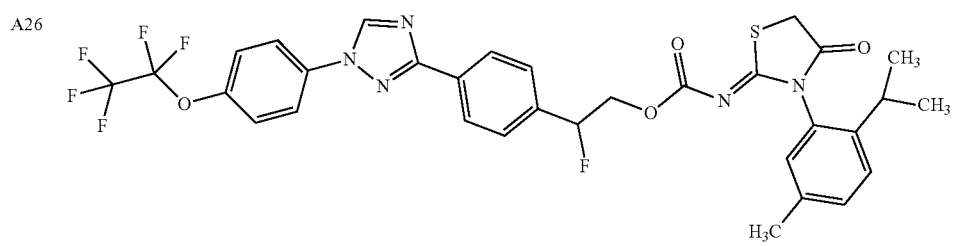
A27
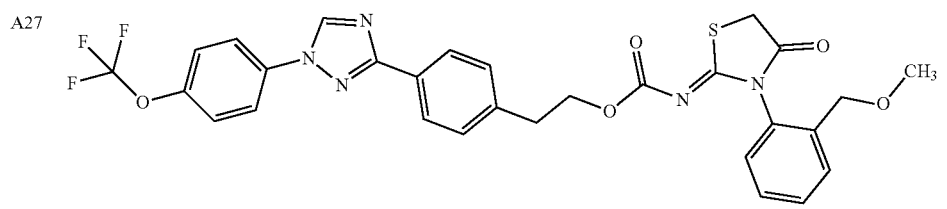
A28
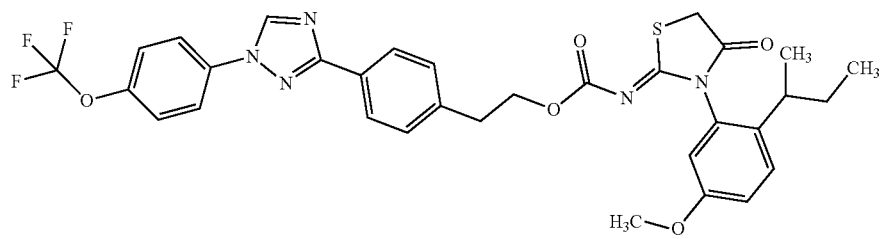 [SMILES: CCC(C)c1ccc(OC)cc1N1C(=O)CS/C1=N\C(=O)OCCc1ccc(-c2ncn(-c3ccc(OC(F)(F)F)cc3)n2)cc1]
A29
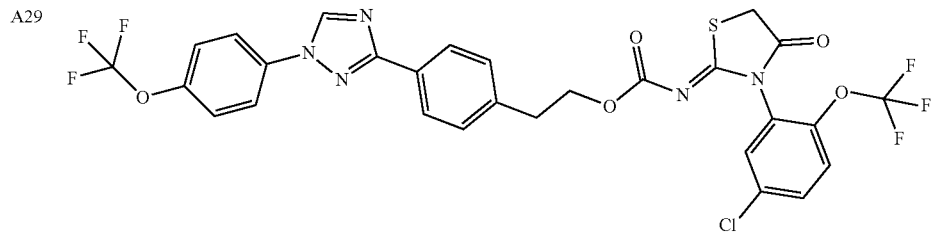
A30
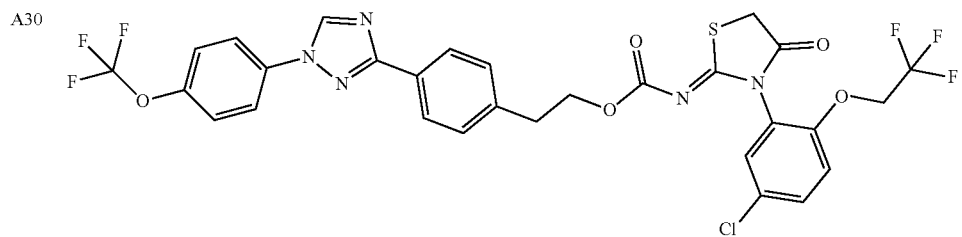

TABLE 1-continued
Structures for Compounds
A31
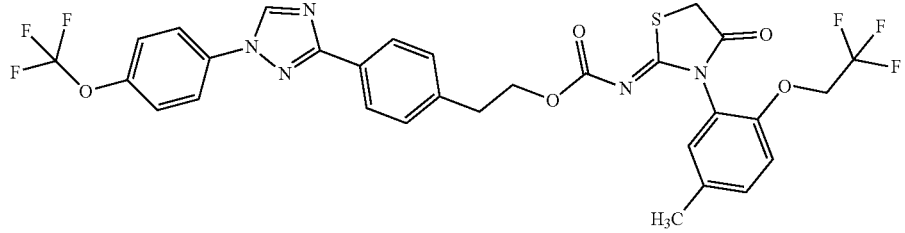 [SMILES: Cc1ccc(OCC(F)(F)F)c(N2C(=O)CS/C2=N\C(=O)OCCc2ccc(-c3ncn(-c4ccc(OC(F)(F)F)cc4)n3)cc2)c1]
A32
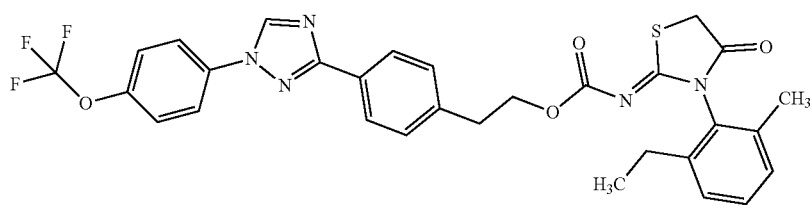 [SMILES: CCc1cccc(C)c1N1C(=O)CS/C1=N\C(=O)OCCc1ccc(-c2ncn(-c3ccc(OC(F)(F)F)cc3)n2)cc1]
A33
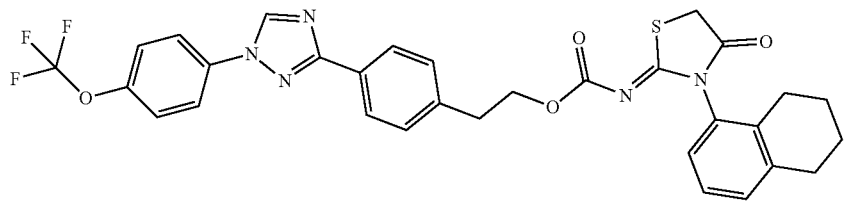 [SMILES: O=C(/N=C1\SCC(=O)N1c1cccc2c1CCCC2)OCCc1ccc(-c2ncn(-c3ccc(OC(F)(F)F)cc3)n2)cc1]
A34
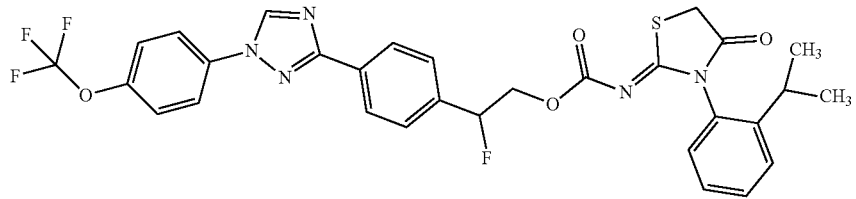 [SMILES: CC(C)c1ccccc1N1C(=O)CS/C1=N\C(=O)OCC(F)c1ccc(-c2ncn(-c3ccc(OC(F)(F)F)cc3)n2)cc1]
A35
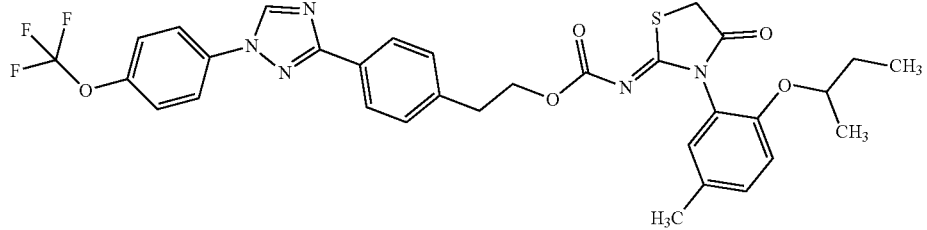 [SMILES: CCC(C)Oc1ccc(C)cc1N1C(=O)CS/C1=N\C(=O)OCCc1ccc(-c2ncn(-c3ccc(OC(F)(F)F)cc3)n2)cc1]
A36
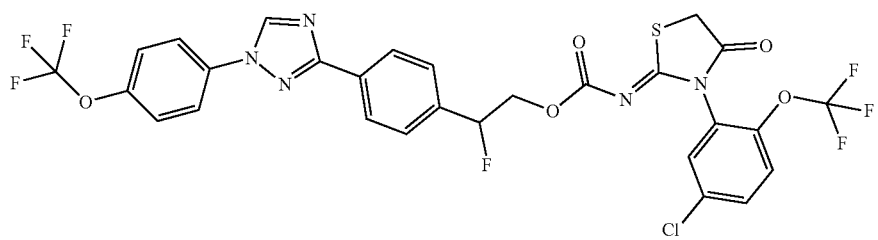 [SMILES: O=C(/N=C1\SCC(=O)N1c1cc(Cl)ccc1OC(F)(F)F)OCC(F)c1ccc(-c2ncn(-c3ccc(OC(F)(F)F)cc3)n2)cc1]

TABLE 1-continued
Structures for Compounds
A37 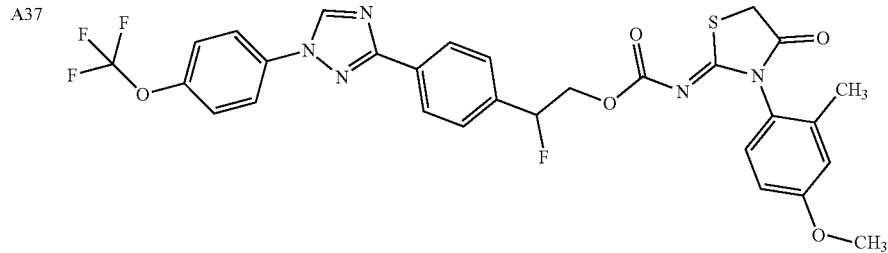
A38 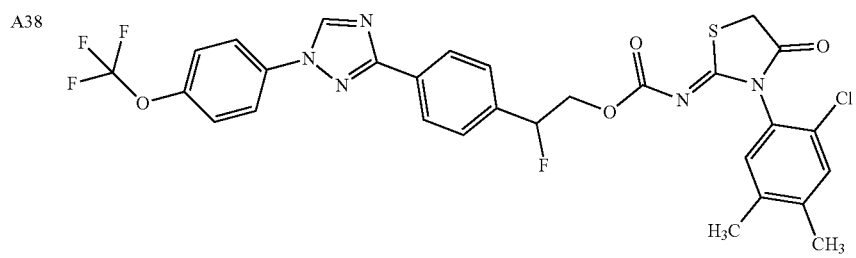
A39 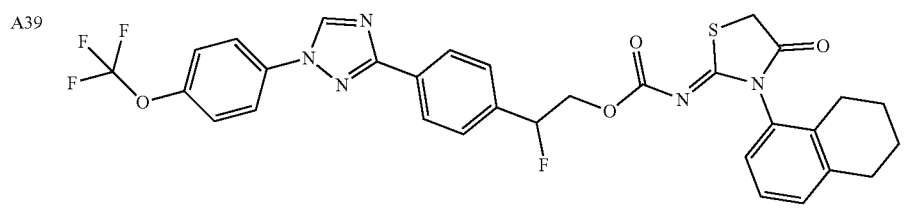
A40 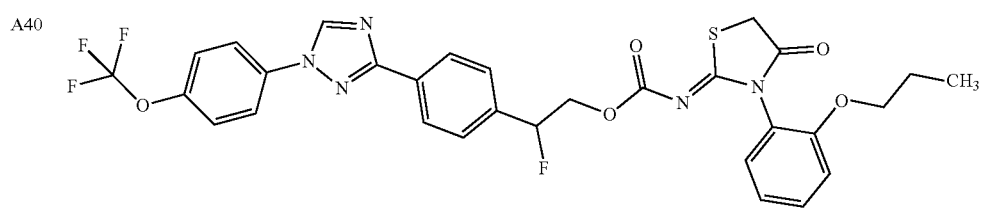
A41 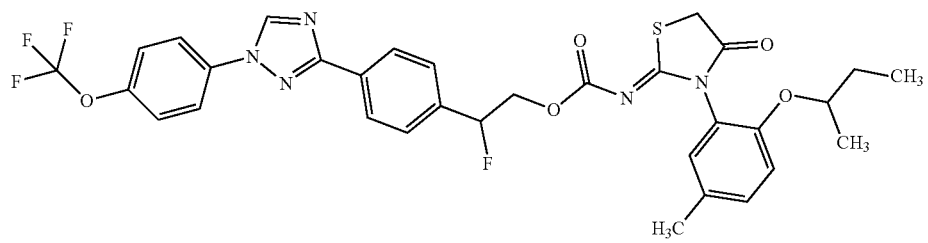
A42 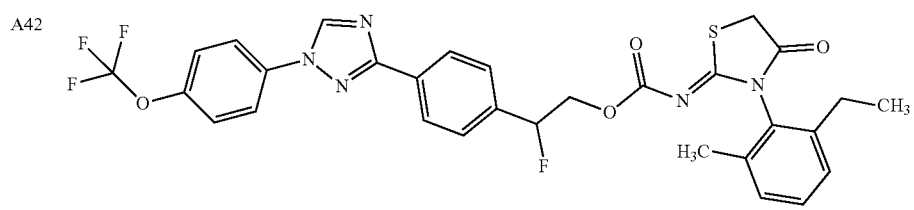

TABLE 1-continued
Structures for Compounds
A43 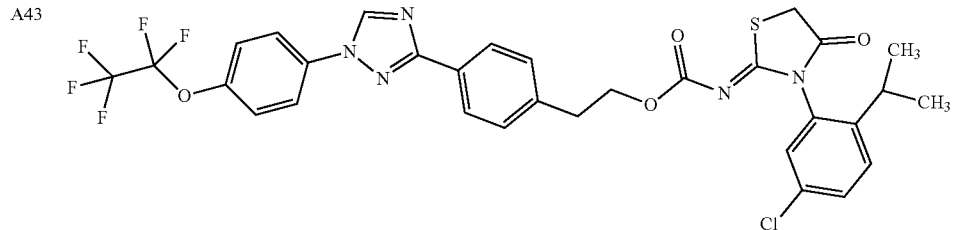
A44 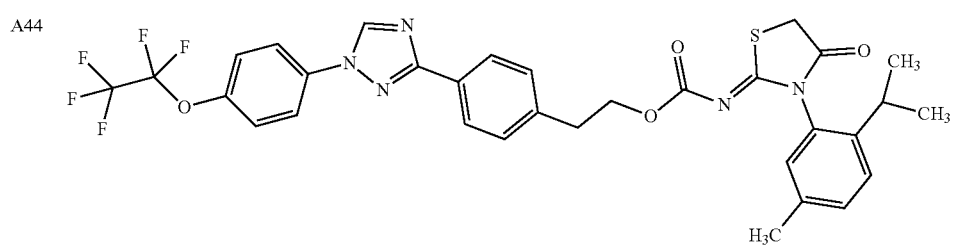
A45 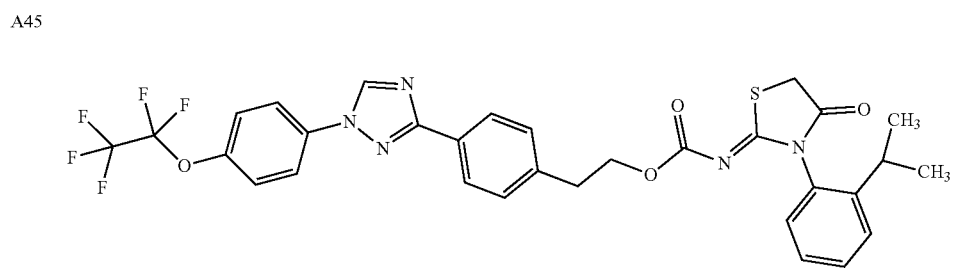
A46 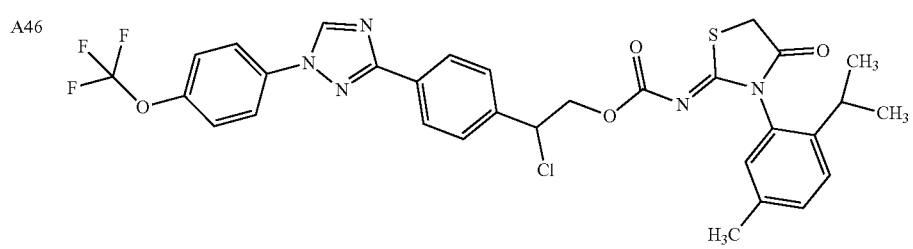
A47 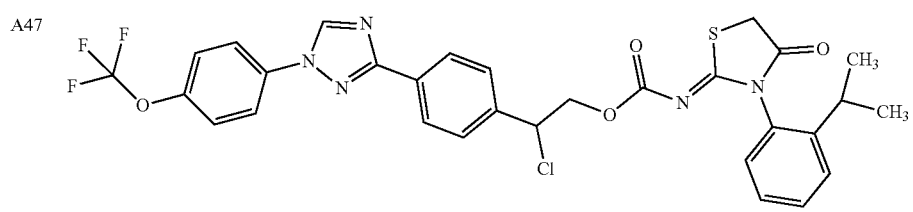
A48 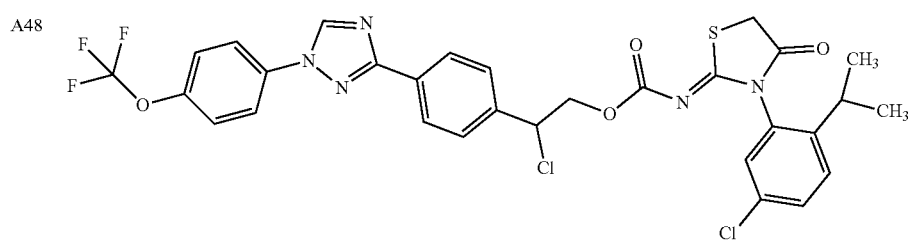

TABLE 1-continued
Structures for Compounds
A49 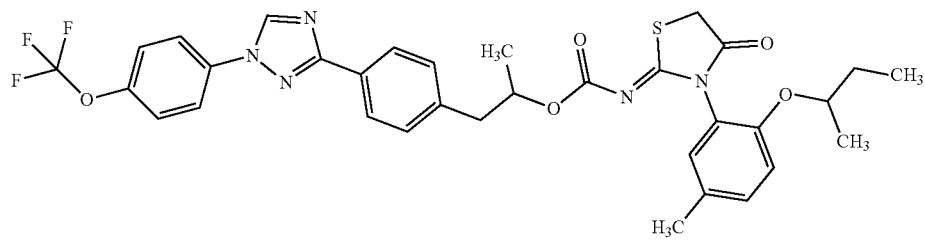 [SMILES: CCC(C)Oc1ccc(C)cc1N1C(=O)CS/C1=N\C(=O)OC(C)Cc1ccc(-c2ncn(-c3ccc(OC(F)(F)F)cc3)n2)cc1]
A50 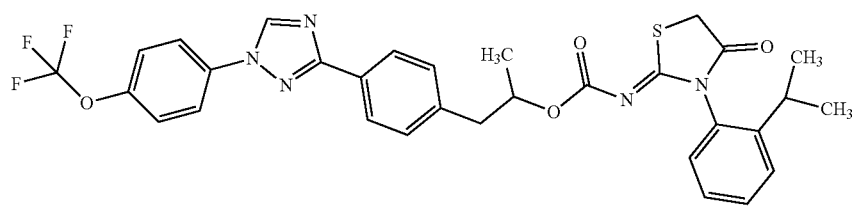 [SMILES: CC(Cc1ccc(-c2ncn(-c3ccc(OC(F)(F)F)cc3)n2)cc1)OC(=O)/N=C1\SCC(=O)N1c1ccccc1C(C)C]
A51 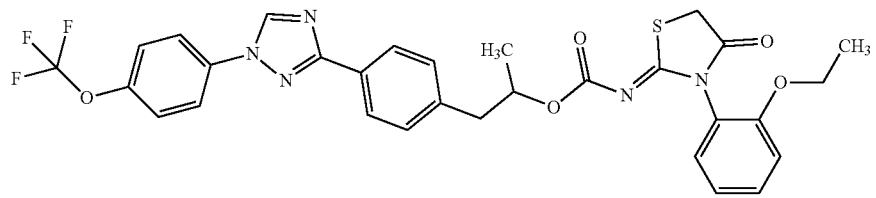 [SMILES: CCOc1ccccc1N1C(=O)CS/C1=N\C(=O)OC(C)Cc1ccc(-c2ncn(-c3ccc(OC(F)(F)F)cc3)n2)cc1]
A52 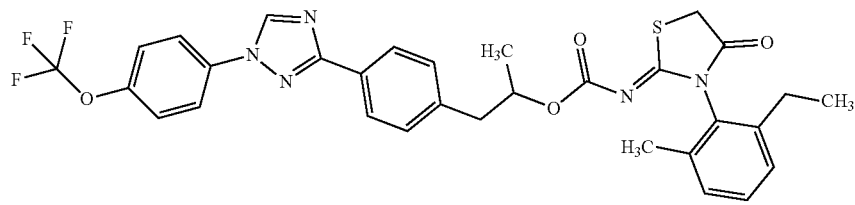 [SMILES: CCc1cccc(C)c1N1C(=O)CS/C1=N\C(=O)OC(C)Cc1ccc(-c2ncn(-c3ccc(OC(F)(F)F)cc3)n2)cc1]
A53 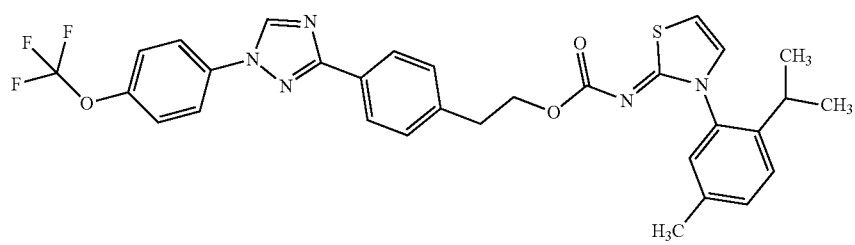
A54 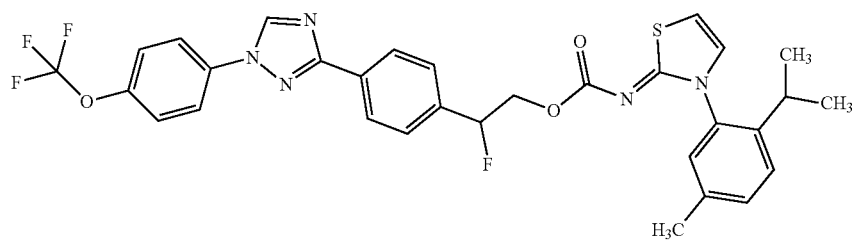

TABLE 1-continued

Structures for Compounds

A55
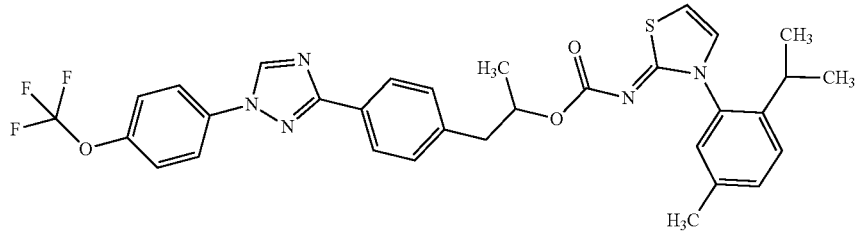 [SMILES: Cc1ccc(C(C)C)c(-n2ccs/c2=N\C(=O)OC(C)Cc2ccc(-c3ncn(-c4ccc(OC(F)(F)F)cc4)n3)cc2)c1]

15. A process to apply a molecule according to claim 1 comprising, applying a molecule according to claim 1, to an area to control a pest, in an amount sufficient to control such pest.

16. A process according to claim 15, wherein said pest is beet armyworm (BAW), cabbage looper (CL), or yellow fever mosquito (YFM).

17. A process comprising applying a molecule according to claim 1 to a genetically modified plant, or genetically-modified seed, which has been genetically modified to express one or more specialized traits.

18. A process comprising: orally administering; or topically applying; a molecule according to claim 1, to a non-human animal, to control endoparasites, ectoparasites, or both.

* * * * *